United States Patent
Dana et al.

(10) Patent No.: US 9,309,313 B2
(45) Date of Patent: Apr. 12, 2016

(54) THERAPEUTIC COMPOSITIONS FOR TREATMENT OF OCULAR INFLAMMATORY DISORDERS

(75) Inventors: Reza Dana, Cambridge, MA (US); Sunil Chauhan, Somerville, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 308 days.

(21) Appl. No.: 12/812,084

(22) PCT Filed: Jan. 9, 2009

(86) PCT No.: PCT/US2009/000114
§ 371 (c)(1),
(2), (4) Date: Jan. 3, 2011

(87) PCT Pub. No.: WO2009/089036
PCT Pub. Date: Jul. 16, 2009

(65) Prior Publication Data
US 2011/0104236 A1    May 5, 2011

(51) Int. Cl.
| | | |
|---|---|---|
| *A61K 39/395* | (2006.01) | |
| *A61K 9/00* | (2006.01) | |
| *A61K 39/00* | (2006.01) | |
| *C07K 16/22* | (2006.01) | |
| *C07K 16/24* | (2006.01) | |
| *A61K 31/724* | (2006.01) | |
| *A61K 31/728* | (2006.01) | |
| *A61K 38/17* | (2006.01) | |
| *A61K 38/20* | (2006.01) | |

(Continued)

(52) U.S. Cl.
CPC .............. *C07K 16/244* (2013.01); *A61K 9/0048* (2013.01); *A61K 9/0051* (2013.01); *A61K 31/724* (2013.01); *A61K 31/728* (2013.01); *A61K 38/1793* (2013.01); *A61K 38/20* (2013.01); *A61K 45/06* (2013.01); *C07K 14/54* (2013.01); *A61K 2039/505* (2013.01); *C07K 2317/75* (2013.01); *C07K 2317/76* (2013.01)

(58) Field of Classification Search
CPC ........... A61K 38/179; A61K 2039/505; A61K 9/0048; C07K 16/22
See application file for complete search history.

(56) References Cited

U.S. PATENT DOCUMENTS

| | | |
|---|---|---|
| 2006/0110429 A1 | 5/2006 | Reiff et al. |
| 2007/0048315 A1* | 3/2007 | Presta .................. 424/145.1 |

(Continued)

FOREIGN PATENT DOCUMENTS

| | | |
|---|---|---|
| WO | WO-9822130 A1 | 5/1998 |
| WO | WO-03070918 A2 | 8/2003 |

(Continued)

OTHER PUBLICATIONS

Ohno et al., (J Rheumatol. 2004;31(7):1362-1368).*

(Continued)

*Primary Examiner* — Cherie M Stanfield
(74) *Attorney, Agent, or Firm* — Mintz Levin Cohn Ferris Glovsky and Popeo, P.C.; Ingrid A. Beattie; Linyu L. Mitra

(57) ABSTRACT

The invention comprises a composition with means to inhibit the function of the inflammatory cytokine IL-17 and methods for using this composition to treat IL-17-mediated ocular inflammatory disorders. The invention also discloses devices for delivering this composition to the eye.

10 Claims, 17 Drawing Sheets

(51) Int. Cl.
*A61K 45/06* (2006.01)
*C07K 14/54* (2006.01)

(56) References Cited

U.S. PATENT DOCUMENTS

2007/0265341 A1  11/2007  Dana et al.
2008/0199460 A1* 8/2008  Cua et al. ............... 424/133.1

FOREIGN PATENT DOCUMENTS

| WO | WO-2004042024 A2 | 5/2004 |
| WO | WO-2005123778 A2 | 12/2005 |
| WO | WO 2006013107 A1 * | 2/2006 |
| WO | WO-2007064752 A2 | 6/2007 |
| WO | WO 2007145618 A1 * | 12/2007 |

OTHER PUBLICATIONS

Iwakura et al., (J Clin Invest. May 2006; 116(5):1218-1222).*
Mentlein, et al. "New Functions of Angiogenic Peptides in Osteoarthritic Cartilage." Current Rheumatology Reviews. 1:337-43 (2005).
Schnyder-Candrian et al. "Interleukin-17 Is a Negative Regulator of Established Allergic Asthma." J.Exp.Med. 203(12):2715-2725 (2006).

* cited by examiner

DRAINING LYMPH NODES

CONJUNCTIVA

| PANEL | | GRADE | CRITERIA |
|---|---|---|---|
| A | | 0 | EQUAL TO OR LESS THAN PANEL A |
| B | | I | EQUAL TO OR LESS THAN PANEL B, GREATER THAN A |
| C | | II | EQUAL TO OR LESS THAN PANEL C, GREATER THAN B |
| D | | III | EQUAL TO OR LESS THAN PANEL D, GREATER THAN C |
| E | | IV | EQUAL TO OR LESS THAN PANEL E, GREATER THAN D |
| >E | | V | GREATER THAN PANEL E |

Fig. 5

Ocular Surface Disease Index (OSDI)
Circle the number in the box that best represents each answer.

Have you experienced any of the following during the last week:

|  | All of the time | Most of the time | Half of the time | Some of the time | None of the time |
|---|---|---|---|---|---|
| 1. Eyes that are sensitive to light? | 4 | 3 | 2 | 1 | 0 |
| 2. Eyes that feel gritty? | 4 | 3 | 2 | 1 | 0 |
| 3. Painful or sore eyes? | 4 | 3 | 2 | 1 | 0 |
| 4. Blurred vision? | 4 | 3 | 2 | 1 | 0 |
| 5. Poor vision? | 4 | 3 | 2 | 1 | 0 |

Have problems with your eyes limited you in performing any of the following during the last week:

|  | All of the time | Most of the time | Half of the time | Some of the time | None of the time |  |
|---|---|---|---|---|---|---|
| 6. Reading? | 4 | 3 | 2 | 1 | 0 | N/A |
| 7. Driving at night? | 4 | 3 | 2 | 1 | 0 | N/A |
| 8. Working with a computer or bank machine (ATM)? | 4 | 3 | 2 | 1 | 0 | N/A |
| 9. Watching TV? | 4 | 3 | 2 | 1 | 0 | N/A |

Have your eyes felt uncomfortable in any of the following situations during the last week:

|  | All of the time | Most of the time | Half of the time | Some of the time | None of the time |  |
|---|---|---|---|---|---|---|
| 10. Windy conditions? | 4 | 3 | 2 | 1 | 0 | N/A |
| 11. Places or areas with low humidity (very dry)? | 4 | 3 | 2 | 1 | 0 | N/A |
| 12. Areas that are air conditioned? | 4 | 3 | 2 | 1 | 0 | N/A |

Total score for answers 1 to 12 _____

Total number of questions answered _____
(Do not include questions answered N/A)

OSDI = (sum of scores)/(# of questions answered) _____

Fig. 6

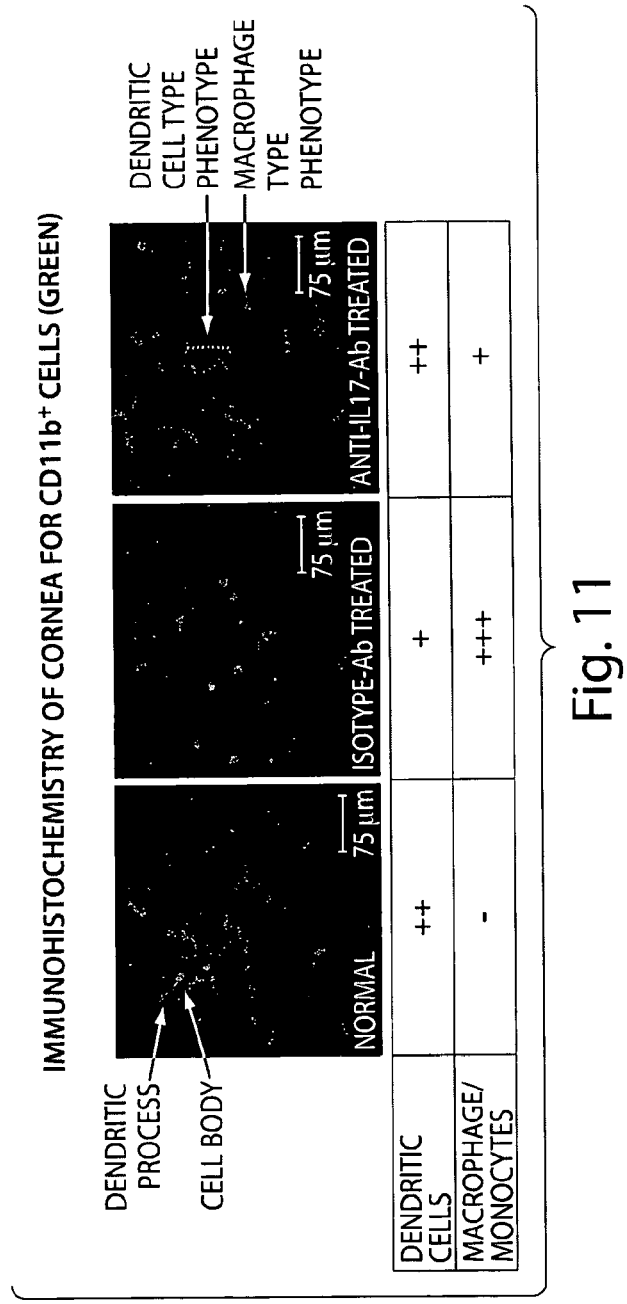

THERAPEUTIC COMPOSITIONS FOR TREATMENT OF OCULAR INFLAMMATORY DISORDERS

RELATED APPLICATIONS

This application is a national stage application, filed under 35 U.S.C. §371, of International Application No. PCT/US2009/000114, filed Jan. 9, 2009, which claims the benefit of provisional application U.S. Ser. No. 61/010,566, filed Jan. 9, 2008, the contents of which are incorporated by reference in their entireties.

FIELD OF THE INVENTION

This invention relates generally to the field of ophthalmology.

BACKGROUND OF THE INVENTION

Ocular surface inflammatory disorders are one of the major causes of visual impairments. Dry Eye Syndrome (DES), which is also known as keratoconjunctivitis sicca, is a predominant ocular surface inflammatory disorder. Current knowledge of the etiology and pathogenesis of ocular surface inflammatory disorders remains inadequate and current treatments provide only temporary and incomplete symptomatic relief.

SUMMARY OF THE INVENTION

The invention comprises a method for inhibiting or reducing the severity of an IL-17-mediated ocular surface inflammatory disorder by locally administering to an eye of a subject a composition that inhibits an activity of an inflammatory interleukin-17 cytokine such as binding of an inflammatory IL-17 cytokine to an IL-17 receptor or other elements of proinflammatory signaling pathways. The claimed compositions and methods fulfill a need for a treatment of an IL-17-mediated ocular surface inflammatory disorders that not only completely addresses the symptoms of this condition, but also affects the underlying biological mechanism. The ability of the methods described herein to target molecular signaling pathways that lead to ocular surface inflammatory disorders provides a long-term solution for treating these common, yet, complex conditions.

In a preferred embodiment, the composition of the claimed invention inhibits the activity of IL-17A or IL-17F. Alternatively, the composition of the claimed invention inhibits the activity of IL-17A and IL-17F. In another preferred embodiment the composition of the claimed invention inhibits the activity of IL-17RA or IL-17RC. Alternatively, the composition of the claimed invention inhibits the activity of IL-17RA a IL-17-mediated ocular surface inflammatory disorders of the invention comprise penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, autoimmune conditions, Pemphigoid syndrome, Stevens-Johnson syndrome, allergy, severe allergic (atopic) eye disease, conjunctivitis, and microbial keratitis. IL-17-mediated ocular surface inflammatory disorders comprise severe allergic (atopic) eye disease. Preferably, IL-17-mediated ocular surface inflammatory disorders do not comprise uveitis, intraocular conditions, or inflammation of interior tissues of the eye.

In one preferred embodiment of the invention, the IL-17-mediated ocular surface inflammatory disorder is Dry Eye Syndrome (DES). Synonyms and related disorders of DES include, but are not limited to, keratoconjunctivitis sicca (KCS), Sjögren syndrome (SS), Sjögren syndrome associated keratoconjunctivitis sicca, non-Sjögren syndrome associated keratoconjunctivitis sicca, keratitis sicca, sicca syndrome, xerophthalmia, tear film disorder, decreased tear production, aqueous tear deficiency (ATD), meibomian gland dysfunction (MGD), and evaporative loss. The subject is identified as suffering from DES or a related disorder by detecting a sign or symptom selected from the group consisting of dry, scratchy, stingy, itchy, burning or pressured sensations, irritation, pain, redness, inflammation, discharge, and excessive eye watering. Alternatively, a subject is identified as suffering from DES or a related disorder if their tear composition is insufficient for proper eye tissue lubrication. The method of therapy inhibits or reduces the severity of at least one of these signs or symptoms.

Dry eye is a multifactorial disorder of the tears and ocular surface that results in symptoms of discomfort, visual disturbance, and tear film instability, with potential damage to the ocular surface. It is accompanied by increased osmolarity of the tear film and inflammation of the ocular surface (emp MA. Report of the National Eye Institute/Industry Workshop on clinical trials in dry eyes. *CLAO J* 1995; 21:221-2). For a more detailed definition, see The definition and classification of dry eye disease: report of the Definition and Classification Subcommittee of the International Dry Eye WorkShop. Ocular Surface. 2007 April; 5(2):75-92, herein incorporated by reference. The method of therapy inhibits or reduces the severity of at least one of these signs or symptoms.

The method comprises administration of a compound that inhibits binding of an inflammatory IL-17 cytokine to the IL-17 receptor complex. Preferred formulations are in the form of a solid, a paste, an ointment, a gel, a liquid, an aerosol, a mist, a polymer, a contact lens, a film, an emulsion, or a suspension. The formulations are administered topically, e.g., the composition is delivered and directly contacts the eye. The composition is present at a concentration of 0.01-50% (weight/volume). For example, the inhibitory composition is present at concentrations of 1% (weight/volume), 10% (weight/volume), 20% (weight/volume), 25% (weight/volume), 30% (weight/volume), 40% (weight/volume), 50% (weight/volume), or any percentage point in between. The method does not involve systemic administration or planned substantial dissemination of the composition to non-ocular tissue.

Optionally, the composition further contains a pharmaceutically-acceptable carrier. Exemplary pharmaceutical carriers include, but are not limited to, compounds selected from the group consisting of a physiological acceptable salt, poloxamer analogs with carbopol, carbopol/hydroxypropyl methyl cellulose (HPMC), carbopol-methyl cellulose, a mucolytic agent, carboxymethylcellulose (CMC), hyaluronic acid, cyclodextrin, and petroleum. In one embodiment, the mucolytic agent is N-acetyl cysteine.

All polynucleotides and polypeptides of the invention are purified and/or isolated. As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

A method for inhibiting or reducing the severity of Dry Eye Syndrome is also carried out by locally administering to an eye of a subject a composition comprising a polynucleotide, a polypeptide, an antibody, a compound, or a small molecule that inhibits or modifies the transcription, transcript stability, translation, modification, localization, secretion, or function of a polynucleotide or polypeptide encoding an inflammatory interleukin-17 cytokine or any component of the IL-17 receptor complex.

The composition may comprise a neutralizing or function-blocking antibody against IL-17 and/or a receptor complex. The neutralizing or function-blocking antibody against IL-17 may be a reformulated or humanized derivative of or bind to the epitope of human IL-17 affinity purified polyclonal antibody (Catalog #AF-317-NA, R&D Systems), human IL-17 allophycocyanin monoclonal antibody (clone 41802) (Catalog #IC3171A, R&D Systems), human IL-17 biotinylated affinity purified polyclonal antibody (Catalog #BAF317, R&D Systems), human IL-17 monoclonal antibody (clone 41802) (Catalog #MAB3171, R&D Systems), human IL-17 monoclonal antibody (clone 41809) (Catalog #MAB317, R&D Systems), human IL-17 phycoerythrin monoclonal antibody (clone 41802) (Catalog #IC3171P, R&D Systems), mouse IL-17 affinity purified polyclonal antibody (Catalog #AF-421-NA, R&D Systems), mouse IL-17 biotinylated affinity purified polyclonal antibody (Catalog #BAF421, R&D Systems), mouse IL-17 monoclonal antibody (clone 50101) (Catalog #MAB721, R&D Systems), or mouse IL-17 monoclonal antibody (clone 50104) (Catalog #MAB421, R&D Systems). Preferably, the neutralizing or function-blocking antibody against IL-17 may be a reformulated or humanized derivative of or bind to the epitope of monoclonal anti-human IL-17 antibody, (Clone: 41809, Catalog #MAB317, R&D Systems), anti-human IL-17 antibody, polyclonal raised in Goat, (Catalog #AF-317-NA, R&D Systems), or recombinant human IL-17 R/Fc chimera (Catalog #177-IR, R&D Systems).

The neutralizing or function-blocking antibody against an IL-17 receptor (IL-17R) may be a reformulated or humanized derivative of or bind to the epitope of human IL-17R affinity purified polyclonal antibody (Catalog #AF177, R&D Systems), human IL-17R allophycocyanin monoclonal antibody (clone 133617) (Catalog #FAB177A, R&D Systems), human IL-17R biotinylated affinity purified polyclonal antibody (Catalog #BAF177, R&D Systems), human IL-17R fluorescein monoclonal antibody (clone 133617) (Catalog #FAB177F, R&D Systems), human IL-17R monoclonal antibody (clone 133617) (Catalog #MAB177, R&D Systems), human IL-17R monoclonal antibody (clone 133621) (Catalog #MAB1771, R&D Systems), human IL-17R phycoerythrin monoclonal antibody (clone 133617) (Catalog #FAB177P, R&D Systems), mouse IL-17R affinity purified polyclonal antibody (Catalog #AF448A, R&D Systems), mouse IL-17R biotinylated affinity purified polyclonal antibody (Catalog #BAF448, R&D Systems), or mouse IL-17R monoclonal antibody (clone 105828) (Catalog #MAB448, R&D Systems).

The neutralizing or function-blocking antibody against an IL-17 may be a reformulated or humanized derivative of, or bind to the epitope of, one or more formats of mouse anti-IL-17A (SKU #s including but not limited to, 7172, 7173, 7175, 7177, 8171, 7371, 7971, and 7370, eBioscience) or mouse anti-IL-17F (SKU #s including, but not limited to, 7471 and 8471, eBioscience). The neutralizing or function-blocking antibody against an IL-17 may be a reformulated or humanized derivative of one or more formats of human anti-IL-17A (SKU #s including, but not limited to, 7178, 7179, 8179, 7176, 7976, and 7876 or human anti-IL-17F SKU #s including, but not limited to, 8479, eBioscience). Preferably, the neutralizing or function-blocking antibody against an IL-17 may be a reformulated or humanized derivative of, or bind to the epitope of functional grade purified anti-human IL-17A antibody (Clone: eBio64CAP17, Catalog #16-7178. eBioscience).

Alternatively, the composition may comprise an intrabody that binds to the IL-17 receptor complex or any synthetic intermediate of IL-17 or the IL-17 receptor complex. The composition may alternatively, or in addition, comprise a soluble fragment of the IL-17 receptor complex which binds IL-17.

Exemplary polypeptides include, but are not limited to, fusion and/or chimeric proteins capable of disrupting IL-17 function. Moreover, the composition comprises morpholino antisense oligonucleotides, microRNAs (miRNAs), short hairpin RNA (shRNA), or short interfering RNA (siRNA) to silence gene expression.

Contemplated function-blocking antibodies targeted against an IL-17 cytokine or an IL-17 receptor are monoclonal or polyclonal. The contemplated antibody binds to one or more sequences within an IL-17 or IL-17 receptor polypeptide. The antibody is alternatively an intrabody. In some embodiments, the antibody comprises a single chain, a humanized, a recombinant, or a chimeric antibody. One or more compounds are directly or indirectly conjugated onto this antibody.

Antagonists of IL-17 and/or its receptor complex are administered either simultaneously or sequentially with a secondary composition comprising one or more of the following: an antibiotic, an immunosuppressive composition, an anti-inflammatory composition, a growth factor, a steroid, a chemokine, or a chemokine receptor.

The composition comprises microRNA molecules adapted for topical administration to ocular or adnexal tissues in order to silence gene expression. Exemplary miRNAs that bind to human IL-17R include, but are not limited to, miR-24 (SEQ ID NO:33), miR-378 (SEQ ID NO:34), and let-7g (SEQ ID NO:35).

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme. Typically small molecules are less than one kilodalton.

In one embodiment of the invention, the composition comprises one or more antibiotic compositions to be used in combination with an antagonist of IL-17 function. The antibiotic and IL-17 antagonist compositions are administered simultaneously or sequentially. Exemplary antibiotic compositions used for combination-therapy with antagonists of IL-17 function include but are not limited to, amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, tetracycline, trimethoprim, cotrimoxazole, demeclocycline, soxycycline, minocycline, doxycycline, oxytetracycline, or tetracycline.

The composition comprises an antagonist of an IL-17 cytokine or an IL-17 receptor complex, administered simultaneously or sequentially with a second immunosuppressive composition. The composition comprising an IL-17 or IL-17R antagonist is administered topically. The second immunosuppressive composition is administered topically or systemically.

The immunosuppressive compound comprises cyclosporin A or analogs thereof a concentration of 0.05-4.0% (mg/ml). Alternatively, or in addition, the immunosuppressive composition comprises a glucocorticoid, a cytostatic agent, an alkylating agent (nitrogen mustards/cyclophosphamide, nitrosoureas, platinum compounds), an antimetabolic agent (methotrexate, any folic acid analog, azathioprine, mercaptopurine, any purine analog, any pyrimidine analog, any inhibitor of protein synthesis), a cytotoxic antibiotic (dactinomycin, an anthracycline, mitomycin C, bleomycin, mithramycin), a polyclonal antibody (Atgam®, Thympglobuline®, any antibody against the antilymphocyte or antithymocyte antigens), a monoclonal antibody (OKT3®, any antibody against the T-cell receptor, any antibody against IL-2, basiliximab/Simulect®, declizumab/Zenapax®), Tacrolimus/Prograf™/FK506, Sirolimus/Rapamune™/Rapamycin, interferon beta, interferon gamma, an opioid, a TNFα binding protein, mycophenolate, or FTY720.

The composition comprises a polynucleotide, a polypeptide, an antibody, or a small molecule that binds or modifies the function of IL-17 or IL-17R administered topically with a pharmaceutically appropriate carrier. Delivery methods for polynucleotide compositions include, but are not limited to, liposomes, receptor-mediated delivery systems, naked DNA, and engineered viral vectors such as herpes viruses, retroviruses, adenoviruses and adeno-associated viruses, among others. Polynucleotide compositions are administered topically with a pharmaceutically acceptable liquid carrier, e.g., a liquid carrier, which is aqueous or partly aqueous. Alternatively, polynucleotide sequences within the composition are associated with a liposome (e.g., a cationic or anionic liposome).

A number of methods have been developed for delivering short DNA or RNA sequences into cells; e.g., polynucleotide molecules can be contacted directly onto the tissue site, or modified polynucleotide molecules, designed to specifically target desired cell types (e.g., sequences linked to peptides or antibodies that specifically bind receptors or antigens expressed on the target cell surface).

A preferred approach uses a recombinant DNA construct in which the short polynucleotide sequence is placed under the control of a strong polymerase III or polymerase II promoter. The use of such a construct will result in the transcription of sufficient amounts of polynucleotide that will form complementary base pairs with the endogenous transcripts of nucleic acids of the invention and thereby prevent translation of endogenous mRNA transcripts. The invention encompasses the construction of a short polynucleotide using the complementary strand as a template. For example, a vector can be introduced in vivo such that it is taken up by a cell and directs the transcription of an interfering RNA or precursor to a double stranded RNA molecule. Alternatively, the template for the short polynucleotide transcript is placed under the transcriptional control of a cell-type specific promoter or other regulatory element. Thus, diffusion or absorption of a topically administered composition beyond the intended ocular target tissue does not cause deleterious or systemic side effects. The vector remains episomal or becomes chromosomally integrated, as long as it can be transcribed to produce the desired polynucleotide.

Vectors are constructed by recombinant DNA technology methods standard in the art. Vectors can be plasmid, viral, or others known in the art, used for replication and expression in mammalian cells. Expression of the sequence encoding the short polynucleotide can be placed under the control of any promoter known in the art to act in mammalian, preferably human cells. Promoters are inducible or constitutive. Exemplary promoters include, but are not limited to: the SV40 early promoter region (Bernoist et al., Nature 290:304, 1981); the promoter contained in the 3' long terminal repeat of Rous sarcoma virus (Yamamoto et al., Cell, 22:787-797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988).

Polypeptide compositions are associated with liposomes alone or in combination with receptor-mediated delivery systems, to enable transport across the plasma membrane. Polypeptide compositions are soluble or membrane-bound. An exemplary receptor-mediated delivery system involves fusion of a low-density or very-low-density lipoprotein containing particle or vesicle to the low-density lipoprotein (LDL) receptor (LDLR) as observed with Hepatitis C Virus (HCV) infection and HCV-mediated drug delivery methods.

Compositions comprise one or more extracellular or intracellular antibodies, also called intrabodies, raised against IL-17 or an IL-17 receptor complex. Extracellular antibodies are topically administered with a pharmacologically appropriate aqueous or non-aqueous carrier. Sequences encoding intracellular antibodies are subcloned into a viral or mammalian expression vector, packed in a lipophilic device to facilitate transport across the plasma membrane, and topically administered to eye tissue with a pharmacologically appropriate aqueous or non-aqueous carrier. Once inside the plasma membrane, host cell machinery transcribes, translates, and processes the intrabody code to generate an intracellular function-blocking antibody targeted against IL-17 or an IL-17 receptor complex. In the case of secreted molecules, intracellular antibodies prevent post-translational modification or secretion of the target protein. In the case of membrane-bound molecules, intracellular antibodies prevent intracellular signaling events upon receptor engagement by IL-17 cytokines.

The composition comprises an antagonist of IL-17 and/or an IL-17 receptor complex function in combination with other inhibitory elements. Antagonists of IL-17 and/or an IL-17 receptor complex and other inhibitory elements are administered simultaneously or sequentially. In one embodiment, the composition comprises an antagonist of IL-17 and/or IL-17 receptor function and an antagonist of tumor necrosis factor alpha (TNFα). Exemplary functional blockers of TNFα include, but are not limited to, recombinant and/or soluble TNFα receptors, monoclonal antibodies, and small molecule antagonists and/or inverse agonists. One or more commercially-available TNF-α blocking agents are reformulated for topical administration in this embodiment. Exemplary commercial TNF-α blocking agents used for reformulation include, but are not limited to, etanerept/Embrel, infliximab/Remicade, and adalimumab/Humira. Alternatively, the composition comprises an antagonist of IL-17 and/or IL-17 receptor function and antagonist(s) of one or more interleukin cytokines. Exemplary cytokines include, but are not limited to, IL-1, IL-2, IL-4, IL-5, IL-6, IL-8, IL-12, IL-18, and IL-23. In another embodiment, the composition comprises an antagonist of IL-17 and/or IL-17 receptor function and antagonist(s) of one or more member(s) of the vascular epithelial growth factor (VEGF) family composed of growth factors and receptors (VEGFR). Exemplary members include, but are not limited to, VEGF-A, VEGF-C, VEGFR-2, and VEGFR-3. In another embodiment, the composition comprises an antagonist of IL-17 and/or IL-17 receptor function and an antagonist of interferon-gamma. In another embodiment, the composition comprises an antagonist of IL-17 and/or IL-17 receptor function and antagonist(s) of one or more chemokines and their receptors. Exemplary chemokines and receptors comprised by the composition of this embodiment include, but are not limited to, chemokine (C-C motif) receptor 1 (CCR1), chemokine (C-C motif) receptor 2 (CCR2), chemokine (C-C motif) receptor 5 (CCR5), chemokine (C-C motif) receptor 7 (CCR7), and chemokine (C-X-C motif) receptor 3 (CXCR3).

In embodiments wherein the composition comprises an antagonist of IL-17 and/or IL-17 receptor function and a second composition, the respective doses of the IL-17 antagonist to the second composition is a ratio between 1:10 and 10:1 (mass/weight). Alternatively, the ratio is 1:9, 1:8, 1:7, 1:6, 1:5, 1:4, 1:3, 1:2, 1:1, 2:1, 3:1, 4:1, 5:1, 6:1, 7:1, 8:1, or 9:1.

The invention also comprises a contact lens device consisting of a composition that inhibits an activity of an inflammatory interleukin-17 cytokine and a pharmaceutically compatible polymer. This composition also comprises a combination of antagonists of IL-17 or IL-17 receptor function as well as secondary compositions. For example, the composition is incorporated into or coated onto said lens. The composition is either chemically bound or physically entrapped by the contact lens polymer. The contact lens is either hydrophobic or hydrophilic.

The invention comprises a drug-delivery device consisting of a composition that inhibits an activity of an inflammatory interleukin-1 cytokine and a pharmaceutically compatible polymer. This composition also comprises a combination of antagonists of IL-17 or IL-17 receptor function as well as secondary compositions. For example, the composition is incorporated into or coated onto said polymer. The composition is either chemically bound or physically entrapped by the polymer. The polymer is either hydrophobic or hydrophilic. The polymer device comprises multiple physical arrangements. Exemplary physical forms of the polymer device include, but are not limited to, a film, a scaffold, a chamber, a sphere, a microsphere, a stent, or other structure. The polymer device has internal and external surfaces. The device has one or more internal chambers. These chambers contain one or more compositions. The device contains polymers of one or more chemically-differentiable monomers. The subunits or monomers of the device polymerize in vitro or in vivo.

The invention comprises a device comprising a polymer and a bioactive composition incorporated into or onto said polymer, wherein said bioactive composition inhibits an activity of an inflammatory interleukin-17 cytokine, and wherein said device is implanted or injected into an ocular surface tissue, an adnexal tissue in contact with an ocular surface tissue, a fluid-filled ocular or adnexal cavity, or an ocular or adnexal cavity.

Exemplary mucoadhesive polyanionic natural or semi-synthetic polymers from which the device is formed include, but are not limited to, polygalacturonic acid, hyaluronic acid, carboxymethylamylose, carboxymethylchitin, chondroitin sulfate, heparin sulfate, and mesoglycan. In one embodiment, the device comprises a biocompatible polymer matrix that may optionally be biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-.epsilon.-caprolactone, polyanhydrides; polyphosphazines, poly(vinyl alcohols), poly (alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In another embodiment, the scaffolds may be fabricated from a variety of synthetic polymers and naturally-occurring polymers such as, but not limited to, collagen, fibrin, hyaluronic acid, agarose, and laminin-rich gels.

One preferred material for the hydrogel is alginate or modified alginate material. Alginate molecules are comprised of (1-4)-linked β-D-mannuronic acid (M units) and α L-guluronic acid (G units) monomers which vary in proportion and sequential distribution along the polymer chain. Alginate polysaccharides are polyelectrolyte systems which have a strong affinity for divalent cations (e.g. $Ca^{+2}, Mg^{+2}, Ba^{+2}$) and form stable hydrogels when exposed to these molecules. See Martinsen A., et al., Biotech. & Bioeng., 33 (1989) 79-89.

An embodiment of the invention utilizes an alginate or other polysaccharide of a lower molecular weight, preferably of size which, after dissolution, is at the renal threshold for clearance by humans. Polymeric devices are located topically or subcutaneously, though very superficially, wherein either a composition chemically bound or physically entrapped by the polymeric device or the device itself, degrades and must be cleared from the body. For a biodegradable polymeric device, it is preferred that the alginate or polysaccharide is reduced to a molecular weight of 1000 to 80,000 daltons, more preferably 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer.

Internal and external surfaces optionally contain pores. Pores are either created prior to administration into a subject or result from the inclusion of pore-forming agents within the device that perforate surfaces upon administration to a subject. Exemplary pore forming agents include, but are not limited to, water soluble compounds such as inorganic salts and sugars. Pore forming agents are added as particulates and comprise between one and thirty percent (weight/weight of polymer). Pore size is sufficient for diffusion of proteins but not large enough cell migration into or out of the device.

The device is administered topically, subconjunctively, or in the episcleral space, subcutaneously, or intraductally. Specifically, the device is placed on or just below the surface if an ocular tissue. Alternatively, the device is placed inside a tear duct or gland. The composition incorporated into or onto the polymer is released or diffuses from the device.

The invention comprises a composition with variable physical and chemical forms; however, the composition is topically administered and contacts an eye directly. The composition is administered as a solid, a paste, an ointment, a gel, a liquid, an aerosol, a mist, a polymer, a film, an emulsion, or a suspension. Furthermore, the composition is incorporated into or coated onto a contact lens or drug delivery device, from which one or more molecules diffuse away from the lens or device or are released in a temporally-controlled manner. In this embodiment, the contact lens composition either remains on the ocular surface, e.g. if the lens is required for vision correction, or the contact lens dissolves as a function of time simultaneously releasing the composition into closely juxtaposed tissues. Similarly, the drug delivery device is optionally biodegradable or permanent in various embodiments.

In one preferred embodiment, the invention comprises a composition with means to inhibit the transcription, transcript stability, translation, modification, localization, secretion, or receptor binding of IL-17. In one preferred embodiment, the composition is capable of binding to one or more regions of an IL-17 mRNA transcript or the IL-17 polypeptide. Alternatively, the composition is capable of binding to one or more regions of an IL-17 mRNA transcript or an IL-17 polypeptide selected from the group consisting of IL-17A, IL-17B, IL-17C, IL-17D, IL-17E, and IL-17F. In another preferred embodiment, the composition is capable of binding to one or more regions of an IL-17A mRNA transcript or the IL-17F polypeptide.

The composition comprises an antagonist or inverse agonist of a receptor for IL-17. IL-17 receptors comprise IL-17RA, IL-17RB, IL-17RC, IL-17RD, and IL-17RE. Preferably IL-17RA and IL-17RC are targeted by an antagonist or inverse agonist. In this embodiment an antagonist is defined as a binding partner, or ligand, of an IL-17R that inhibits the function of an agonist, IL-17, or inverse agonist by blocking its binding to the receptor. An inverse agonist is defined as a molecule which binds to the same IL-17R binding-site as an agonist, for instance, IL-17, but exerts the opposite pharmacological effect. The composition contains a polynucleotide, a polypeptide, an antibody, a compound, or a small molecule that binds to a region of an IL-17R mRNA or polypeptide.

In another preferred embodiment, the composition comprises a human recombinant IL-17R antagonist either in pure form, or as a component of a mixture. The human recombinant IL-17R antagonist is combined with balanced saline, carboxymethylcellulose (CMC), or hyaluronic acid (HA), or other vehicles prior to the composition contacting the ocular surface. Within these mixtures, the human recombinant IL-17R antagonist comprises at least 0.1%, 2.0%, 2.5%, 5%, 10% or at most 50% of the total volume administered. Purified is defined as the antagonist in the absence of unrelated polynucleotides, polypeptides, cellular organelles, or lipids. Purified defines a degree of sterility that is safe for administration to a human subject, e.g. lacking infectious or toxic agents.

The invention provides a method of restoring or augmenting regulatory T-cell-mediated immune suppression in a subject with an IL-17-mediated ocular disease including administering to the subject a composition that inhibits an activity of an inflammatory interleukin-17 cytokine, restoring or augmenting regulatory T-cell-mediated immune suppression. Alternatively, or in addition, the invention also provides a method of restoring or augmenting regulatory T-cell-mediated immune suppression in a subject with dry eye including administering to the subject a composition that inhibits an activity of an inflammatory interleukin-17 cytokine, thereby restoring or augmenting regulatory T-cell-mediated immune suppression. Alternatively, the subject has an ocular disorder.

Furthermore, the invention provides a method of reducing Th17 cell abundance in an ocular, adnexal, or lymph tissue of a subject in need thereof including administering to the subject a composition that inhibits an activity of an inflammatory interleukin-17 cytokine. For example, a method of decreasing or inhibiting secretion of lymphangiogenesis-specific growth factors in an ocular or adnexal tissue of a subject with dry eye is carried out by administering to the subject a composition that inhibits an activity of an inflammatory interleukin-17 cytokine, thereby inhibiting lymphangiogenesis. In certain embodiments of the invention, the lymphangiogenesis-specific growth factors are VEGF-C, VEGF-D, a VEGF receptor, or a combination thereof. Moreover, the invention provides a method of decreasing or inhibiting secretion of lymphangiogenesis-specific growth factors in an ocular or adnexal tissue of a subject with an IL-17-mediated ocular disease including administering to the subject a composition that inhibits an activity of an inflammatory interleukin-17 cytokine, thereby inhibiting lymphangiogenesis.

Furthermore, the invention provides a method of reducing macrophage and monocyte cell abundance or concentration in an ocular, adnexal, or lymph tissue of a subject in need thereof including administering to the subject a composition that inhibits an activity of an inflammatory interleukin-17 cytokine.

A method of reducing pathogenic immune cell abundance in an ocular, adnexal, or lymph tissue of a subject in need thereof includes administering to the subject a composition that inhibits an activity of an inflammatory interleukin-17 cytokine. As used herein, the term "pathogenic immune cell" is meant to describe any immune cell that exacerbates, induces, reduces the time to onset, or prolongs the appearance a sign or symptom of an ocular disease. Pathogenic immune cells in this context antagonize or decrease an IL-17 inhibiting activity of compositions of the invention.

Pathogenic lymphatic vessel growth in an ocular, or adnexal tissue of a subject is inhibited or reduced by administering to the subject a composition that inhibits an activity of an inflammatory interleukin-17 cytokine. Pathogenic lymphatic vessel growth encompasses lymphatic vessel growth that exacerbates, induces, reduces the time to onset, or prolongs the appearance a sign or symptom of an ocular disease. Moreover, pathogenic lymphatic vessel growth antagonizes or decreases an IL-17 inhibiting activity of compositions of the invention. Alternatively, or in addition, pathogenic lymphatic vessel growth occurs prior to, simultaneously with, or following the presentation of an IL-17-mediated ocular disease. Pathogenic lymphatic vessel growth includes the ability of lymphatic vessels to expand within or to invade corneal tissue or describes the potential and/or actual growth, expansion, elaboration, splitting, or remodeling of lymphatic vessels either within a corneal tissue or from a non-corneal tissue (such as the adjacent limbus) into corneal tissue. Alternatively, or in addition, pathogenic lymphatic vessel growth permits or induces the transport of immune cells, which encompasses the unidirectional or bidirectional movement or deposition of an immune cell between a corneal tissue and a non-corneal tissue, preferably, a lymph node or other sites in the lymphoid compartment. Exemplary immune cells is include, but are not limited to, T cells, B cells, dendritic cells, macrophages, monocytes, and natural killer (NK) cells.

The invention also provides a method for reducing corneal nerve damage in a subject in need thereof, including the steps of: (a) identifying a subject with corneal nerve damage; and (b) locally administering to the cornea of the subject a composition that inhibits an activity of an inflammatory interleukin-17 cytokine, thereby enhancing corneal nerve regeneration, reducing the development of abnormalities in nerve morphology, and reducing corneal nerve damage.

In certain embodiments of the above method, the subject is identified as having corneal nerve damage or loss that results from a congenital defect, disease, trauma, medical or surgical procedure. Alternatively, or in additional, the subject is identified as having corneal nerve damage or loss that results from neurotrophic keratitis, herpes simplex, zoster keratitis, diabetes mellitus, trigeminal nerve damage, orbital or head surgery, head trauma, aneurysm, intracranial neurologic disease, keratorefractive procedures, photorefractive keratectomy (PRK), laser in situ keratomileusis (LASIK), congenital defect, ocular surface disease, dry eye syndrome, a non-ophthalmic disorder, a non-ophthalmic procedure, peripheral neuropathy, or diabetic neuropathy.

The invention provides a method for preventing corneal nerve damage in a subject in need thereof, including the steps of: (a) identifying the subject at risk of exposure to corneal nerve damage; and (b) locally administering to the cornea of the subject a composition that inhibits an activity of an inflammatory interleukin-17 cytokine prior to the exposure, thereby decreasing nerve degeneration, reducing the development of abnormalities in nerve morphology, and preventing damage corneal nerve damage.

For example, the subject is identified as being at risk of exposure to corneal nerve damage or loss that could result from disease, trauma, or a medical procedure. Alternatively, or in addition, the subject is identified as being at risk of exposure to corneal nerve damage or loss that could result from neurotrophic keratitis, herpes simplex, zoster keratitis, diabetes mellitus, trigeminal nerve damage, orbital or head surgery, head trauma, aneurysm, intracranial neurologic disease, keratorefractive procedures, photorefractive keratectomy (PRK), laser in situ keratomileusis (LASIK), ocular surface disease, dry eye syndrome, a non-ophthalmic disorder, a non-ophthalmic procedure, peripheral neuropathy, or diabetic neuropathy.

The above methods further include the step of identifying a subject with a sign or symptom of corneal nerve damage or loss. For example, a sign of corneal nerve damage or loss is a decrease of corneal innervation or sensation, a reduction in the number of nerve fibers or bundles innervating the cornea, death of neurons innervating the cornea, a decrease or loss of neurotransmitter release, a decrease or loss of nerve growth factor release, abnormal tearing reflexes, abnormal blink reflexes, abnormal nerve morphology, appearance of abnormal nerve sprouts, abnormal tortuosity, increased bead-like nerve formations, thinning of nerve fiber bundles, or thickening of nerve fiber bundles. For example, a symptom of corneal nerve damage or loss is abnormal tear production or dryness, abnormal blinking, and difficulty or loss of ability to focus, decreased or lost visual acuity, or decreased or lost corneal sensitivity.

Signs or symptoms of corneal damage or abnormal nerve morphology are detected, analyzed, examined, and evaluated using in vivo confocal microscopy (IVCM) of the central cornea or other imaging or diagnostic devices that allow for detection of corneal nerve damage. Exemplary devices for IVCM include, but are not limited to the Heidelberg Retina Tomograph 3 with the Rostock Cornea Module (HRT3/RCM) (Heidelberg Engineering GMBH) and the Confoscan 4 Confocal Microscope (Nidek, Inc.). In certain embodiments of the above methods, IVCM is used to detect, analyze, examine, and evaluate the form and number of nerve fibers in the various corneal layers, as well as to discriminate between parallel running, bifurcating, branching, and interconnecting nerve fiber bundles. Alternatively or in addition, IVCM is used to detect, analyze, examine, and evaluate changes in the total number of nerves, changes in the length of nerves, nerve density, the presence or absence of abnormal nerve sprouts, the presence or absence of abnormal nerve fiber tortuosity, changes in number or morphology of bead-like nerve formations, and thinning versus thickening of nerve fiber bundles. In one aspect of the methods of the invention, IVCM is used to detect, analyze, examine, and evaluate nerve regeneration. Alternatively, or in addition, IVCM is used to detect, analyze, examine, and evaluate nerve degeneration. For instance, IVCM has been used to show an average of 6-8 corneal nerve bundles per image within the subbasal area of healthy individuals and nerve regeneration in patients who experienced nerve damage as a result of photoreceptive keratectomy.

In certain preferred embodiments, the above methods are performed on a corneal tissue.

Publications, U.S. patents and applications, Genbank/NCBI accession numbers, and all other references cited herein, are hereby incorporated by reference.

BRIEF DESCRIPTION OF THE DRAWINGS

Table 1 is a summary of mRNAs comprised in the invention, their human target genes, amino acid sequences, and their sequence identifier numbers.

FIG. 5 is the Oxford schema for grading corneal and conjunctival staining (see, Example 4).

FIG. 6 is an Ocular Surface Disease Index (OSDI) 12-item questionnaire.

FIG. 11 is a series of micrographs and associated key showing that topical application of anti-IL-17 antibody maintains the normal phenotype of CD11b+ cells in cornea. Representative micrographs showing CD11b staining in corneas of different groups. Corneas of Anti-IL17-antibody treated group show that similar to normal cornea, majority of CD11b+ cells have phenotype of resident dendritic cells. However, corneas of Isotype-antibody treated group show that phenotype of majority of CD11b+ cells are similar to the infiltrating pathogenic macrophages/monocytes.

DETAILED DESCRIPTION

Ocular Surface Inflammatory Disorders

Figure 1:
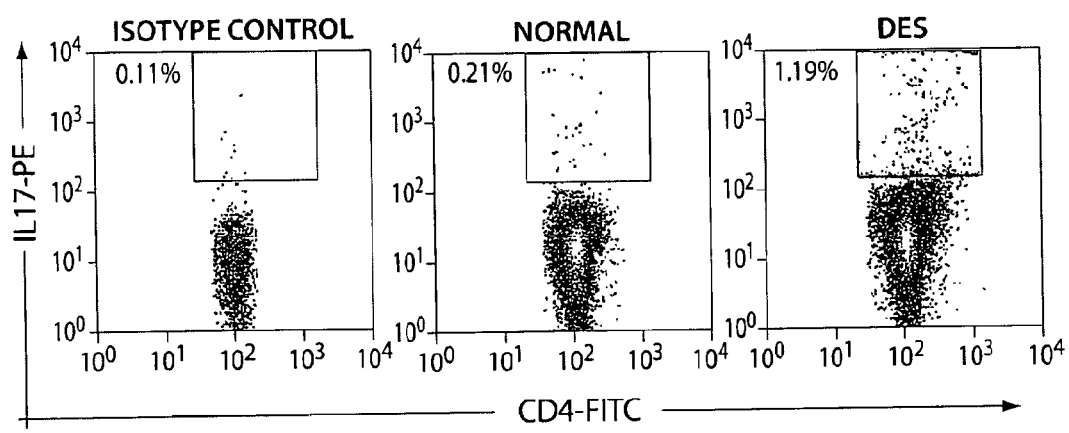
FIG. 1 is a series of graphs depicting flow cytometric dots demonstrating increased frequency of IL-17 producing CD4+ T cells in the draining lymph nodes of mice with DES compared to those of normal mice (p=0.03).

DES is a predominant ocular surface inflammatory disorder, however, other disorders are contemplated. Exemplary contemplated ocular surface inflammatory disorders include, but are not limited to, penetrating keratoplasty (corneal transplantation), corneal neovascularization, allergy, conjunctivitis, and microbial keratitis. Contemplated disorders can be caused by autoimmune mechanisms, bone marrow transplant, surgery (general eye surgery, corneal transplantation, refractive surgery, LASIK), allergy, infection, trauma, injury, drug use, tear film abnormalities, contact lens use, neovascularization, tumor formation or growth, exposure to airborne or liquid irritants, hormonal variation, deprivation of essential fatty acids, and genetic predisposition.

Dry Eye Syndrome (DES):

DES and related diseases can be caused by autoimmune and environmental conditions as well as any activity that decreases the rate of blinking. Alternatively, DES and related diseases are caused by decreased tear production or a change in tear composition that results in inadequate lubrication of the eye. Contact lens use, eye surgery, and eye injury can induce DES. Finally, DES often occurs as a consequence of aging and hormonal changes.

Dry eye is a multifactorial disease of the tears and ocular surface that results in symptoms of discomfort, visual disturbance, and tear film instability, with potential damage to the ocular surface. It is accompanied by increased osmolarity of the tear film and inflammation of the ocular surface (emp MA. Report of the National Eye Institute/Industry Workshop on clinical trials in dry eyes. *CLAO J* 1995; 21:221-2). For a more detailed definition, see The definition and classification of dry eye disease: report of the Definition and Classification Subcommittee of the International Dry Eye WorkShop. Ocular Surface. 2007 April; 5(2):75-92, herein incorporated by reference. The method of therapy inhibits or reduces the severity of at least one of these signs or symptoms.

Synonyms and related diseases of DES include, but are not limited to, keratoconjunctivitis sicca (KCS), Sjögren syndrome (SS), Sjögren syndrome associated keratoconjunctivitis sicca, non-Sjögren syndrome associated keratoconjunctivitis sicca, keratitis sicca, sicca syndrome, xerophthalmia, tear film disorder, decreased tear production, aqueous tear deficiency (ATD), meibomian gland dysfunction, and evaporative loss. The subject is identified as suffering from DES or a related disorder by detecting a sign or symptom selected from the group consisting of dry, scratchy, stingy, itchy, burning or pressured sensations, irritation, pain, redness, inflammation, discharge, and excessive eye watering. Alternatively, a subject is identified as suffering from DES or a related disorder if their tear composition is insufficient for proper eye tissue lubrication. The method of therapy inhibits or reduces the severity of at least one of these signs or symptoms.

Th17 Cells

T lymphocytes are circulating small white blood cells that play a central role in cell-mediated immunity. T helper cells (Th), also known as effector T cells, are one subgroup of T lymphocytes. Th17 cells are a recently-identified population of T helper cells that produce Interleukin-17 (IL-17) and have been shown to contribute to autoimmune conditions. Importantly, these cells have not been previously implicated in DES.

Determination of IL-17-Mediated Ocular Surface Inflammation

Exemplary tests used to determine the occurrence and severity of ocular surface inflammation include, but are not limited to, the following:

The Surface Disease Index (OSDI)

The Ocular Surface Disease Index (OSDI) is a 12-item questionnaire that provides a rapid assessment of the symptoms of ocular irritation consistent with ocular surface inflammatory disorders, including DES, and their impact on vision-related functioning (FIG. 6). The 12 items of the OSDI questionnaire are graded on a scale of 0 to 4, where 0 indicates none of the time; 1, some of the time; 2, half of the time; 3, most of the time; and 4, all of the time. The total OSDI score is then calculated on the basis of the following formula: OSDI=[(sum of scores for all questions answered)×100]/[(total number of questions answered)×4]. Thus, the OSDI is scored on a scale of 0 to 100, with higher scores representing greater disability. A negative change from baseline indicates an improvement in vision-related function and the ocular inflammatory disorders described herein. For the therapeutic method described herein, treatment is considered more effective than control (vehicle) as indicated by a mean change (decrease) from baseline for the OSDI of >10 units compared to control.

Therapeutic treatment is considered more effective than the vehicle as indicated by a mean change from baseline of average score (0-100) for the Ocular Surface Disease Index (OSDI) of >10 units better than vehicle.

Corneal and Conjunctival Staining

Corneal staining is a measure of epithelial disease, or break in the epithelial barrier of the ocular surface, typically seen with ocular surface inflammatory disorders such as DES, among others. Importantly, corneal staining can exist even without clinically evident dry eye, if there is significant lid disease, such as posterior blepharitis. Corneal staining is highly correlated with ocular discomfort in many, though not all patients; in general corneal staining is associated with high scores in the OSDI, as described above. For corneal fluorescein staining, saline-moistened fluorescein strips or 1% sodium fluorescein solution are used to stain the tear film. The entire cornea is then examined using slit-lamp evaluation with a yellow barrier filter (#12 Wratten) and cobalt blue illumination (staining is more intense when it is observed with a yellow filter). Staining is graded according to the Oxford Schema (FIG. 5).

Conjunctival staining is a measure of epithelial disease or break in the epithelial barrier of the ocular surface, typically seen with ocular surface inflammatory disorders such as DES, among others. Importantly, conjunctival staining, similar to corneal staining, can exist even without clinically evident dry eye, if there is significant lid disease, such as posterior blepharitis. Conjunctival staining can also correlate with symptoms of ocular irritation and high OSDI scores as described above. Conjunctival staining is performed under the slit-lamp using lissamine green. Saline-moistened strip or 1% lissamine green solution is used to stain the tear film, and interpalpebral conjunctival staining is evaluated more than 30 seconds, but less than 2 minutes, later. Using white light of moderate intensity, only the interpalpebral region of the nasal and temporal conjunctival staining is graded using the Oxford Schema (FIG. 5). The treatment described herein leads to decreases in ocular staining scores beyond what is observed with the vehicle alone.

Therapeutic treatment is considered more effective than vehicle as indicated by a mean change from baseline in average score (0-5 scale) for corneal and conjunctival staining of >1 unit better than vehicle, e.g. as detected using the Oxford Schema.

Schirmer Test

The Schirmer test is performed in the presence and in the absence of anesthesia by placing a narrow filter-paper strip (5×3 5 mm strip of Whatman #41 filter paper) in the inferior cul-de-sac. This test is conducted in a dimly lit room. The patient gently closes his/her eyes until five minutes have elapsed and the strips are removed. Because the tear front will continue advancing a few millimeters after it has been removed from the eyes, the tear front is marked with a ball-point pen at precisely five minutes. Aqueous tear production is measured by the length in millimeters that the strip wets during 5 minutes. Results of 10 mm or less for the Schirmer test without anesthesia and 5 mm or less for the Schirmer test with anesthesia are considered abnormal. A positive change from baseline indicates improvement of one or more symptoms of an ocular inflammatory disorder described herein.

Conjunctiva Hyperemia

Bulbar conjunctival hyperemia is graded as follows:
None (0): none
Mild (1): slight localized injection
Moderate (2): pink color, confined to palpebral or bulbar conjunctiva
Severe (3): red color of the palpebral and/or bulbar conjunctiva
Very Severe (4): marked dark redness of the palpebral and/or bulbar conjunctiva The presence or absence of tarsal papillary hypertrophy is also noted.

Impression Cytology

Filter paper or other collection devices are used to collect cells and liquid samples from the ocular surface, tear ducts, or meibomian glands to be tested for the presence and/or abundance of an IL-17 cytokine, an IL-17 receptor, and/or a Th17 cell. The presence and/or abundance of RNA, DNA, or protein relating to an IL-17 cytokine or IL-17 receptor is determined by standard methods including, but not limited to, polymerase chain reaction (PCR), reverse transcriptase PCR (RT-PCR), gel electrophoresis, probe hybridization, antibody detection, in situ hybridization, Western blot, Northern Blot, Southern Blot, fluorescent microscopy, flow cytometry, enzyme-linked immunosorbant assay (ELISA), immunoprecipitation, gene chip analysis, protein chip analysis, cell culture methods, and cell sorting (see, Gulati A, Saccheti M, Bonini S, Dana R. Chemokine Receptor CCR5 Expression in Conjunctival Epithelium of Patients with Dry Eye Syndrome. *Arch Ophthalmol* 2006; 124: 710-716; Argueso P, Balaram M, Spurr-Michaud S, Keutmann H T, Dana M R, Gipson I K. Decreased levels of goblet cell mucin MUC5AC in tears of Sjögren's syndrome patients. *Invest Ophthalmol Vis Sci.* 2002; 43: 1004-1011. Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

Corneal Structure

The cornea is the transparent front part of the eye that covers the iris, pupil, and anterior chamber. Together with the lens, the cornea refracts light, and as a result helps the eye to focus, accounting for approximately two-thirds of the eye's total optical power. The cornea has unmyelinated nerve endings sensitive to touch, temperature and chemicals; a touch of the cornea causes an involuntary reflex to close the eyelid. Because transparency is of prime importance the cornea does not have blood vessels; it receives nutrients via diffusion from the tear fluid at the outside and the aqueous humor at the inside and also from neurotrophins supplied by nerve fibers that innervate it. In humans, the cornea has a diameter of about 11.5 mm and a thickness of 0.5-0.6 mm in the center and 0.6-0.8 mm at the periphery.

Transparency, avascularity, the presence of highly immature resident immune cells, and immunologic privilege makes the cornea a unique tissue. Immune privilege is meant to describe certain sites in the body that are able to tolerate the introduction of an antigen without eliciting an inflammatory immune response. The cornea has no blood supply, but rather, the cornea it gets oxygen directly through the air and the tears that bathe it. The human cornea, like that of other primates, has five layers. From the anterior to posterior they are the corneal epithelium, Bowman's layer, the corneal stroma, Descemet's membrane, and the corneal endothelium. The corneal epithelium is a thin epithelial multicellular tissue layer, stratified squamous epithelium, of continuously regenerating cells, kept moist with tears. Irregularity or edema of the corneal epithelium disrupts the smoothness of the air-tear film interface, the most significant component of the total refractive power of the eye, thereby reducing visual acuity. Bowman's layer, also known as the anterior limiting membrane, is a condensed layer of irregularly-arranged collagen, about 8-14 microns thick, that protects the corneal stroma. The corneal stroma, also known as the substantia propria, is a thick and transparent middle layer, consisting of regularly-arranged collagen fibers along with sparsely populated keratocytes. The corneal stroma consists of approximately 200 layers of type I collagen fibrils. Ninety percent of the corneal thickness is composed of the stroma. Descemet's membrane, also known as the posterior limiting membrane, is a thin and acellular layer that serves as the modified basement membrane of the corneal endothelium. The corneal endothelium is a simple squamous or low cuboidal monolayer of mitochondria-rich cells responsible for regulating fluid and solute transport between the aqueous and corneal stromal compartments. The corneal endothelium is bathed by aqueous humor, not by blood or lymph, and has a very different origin, function, and appearance from vascular endothelia. Unlike the corneal epithelium, the cells of the endothelium do not regenerate. Instead, corneal endothelial cells expand or spread to compensate for dead cells which reduces the overall cell density of the endothelium and impacts fluid regulation.

The cornea is one of the most sensitive tissues of the body, it is densely innervated with sensory nerve fibers via the ophthalmic division of the trigeminal nerve by way of 70-80 long and short ciliary nerves. Nerves enter the cornea via three levels, scleral, episcleral and conjunctival. Most of the bundles subdivide and form a network in the stroma, from which fibers supply different regions of the cornea. Three exemplary networks are midstromal, subepithelial/Bowman's layer, and epithelium. Corneal nerves of the subepithelial layer converge and terminate near the apex of the cornea.

Corneal Innervation

The cornea is one of the most densely innervated tissues in the body and is abundantly supplied by different types of nerve fibers. Rabbit studies have revealed that the nerve density of the corneal epithelium is about 300-600 times as much as that of skin and 20-40 times that of the dental pulp. It is estimated that there are approximately 7000 sensory receptors per $mm^2$ in the human corneal epithelium, implying that injuries to individual epithelial cells may be adequate to give a pain perception (Exp Eye Res 2003; 76:521-42).

Most corneal nerve fibers are sensory in origin and are derived from the ophthalmic branch of the trigeminal nerve. Nerve bundles enter the peripheral mid-stromal cornea in a radial fashion parallel to the corneal surface. Soon after entering the cornea, the main stromal bundles branch repeatedly and dichotomously into smaller fascicles that ascended into progressively more superficial layers of the stroma. Eventually the stromal nerve fibers turn abruptly 90°, penetrate Bowman's layer and proceed towards the corneal surface. After penetrating Bowman's layer, bundles divide and run parallel to the corneal surface between Bowman's layer and the basal epithelium, forming the subbasal nerve plexus. The density and number of nerves in the subbasal epithelial nerve plexus are significantly greater than the density and number of nerves in the remaining corneal layers. Subbasal fibers subsequently form branches that turn upward and enter the corneal epithelium between the basal cells to reach the wing cells, where they terminate (Invest Ophthalmol Vis Sci 1996; 37:476-88).

Corneal nerve fibers mediate not only sensation but also exert critical trophic influences on the corneal epithelium and play a vital role to the preservation of a healthy ocular surface. Corneal sensation is a key mechanism in preventing injury through the blink reflex and reflex tearing. Enhanced epithelial cell proliferation is mediated by neurotransmitters and nerve growth factors released from corneal nerve endings (Acta Ophthalmol Suppl 1989; 192:115-34). Dysfunction of corneal innervation produces a degenerative condition known as neurotrophic keratitis, which therefore renders the corneal surface vulnerable to occult injury and delayed healing of established corneal epithelial injuries. Most clinical cases of neurotrophic keratitis are caused by herpes simplex or zoster keratitis, diabetes mellitus, or by trigeminal nerve damage associated with orbital or head surgery, head trauma, aneurysms, or intracranial neurologic disease. Absent or reduced corneal sensation may be congenital in origin. Keratorefractive procedures such as photorefractive keratectomy (PRK) and laser in situ keratomileusis (LASIK) can sever stromal and subbasal corneal nerves plexus and produce a transient mild to severe neurotrophic dry eye.

Intact corneal innervation is also mandatory for tearing reflexes. Under normal physiological conditions, sensory nerves in the cornea transmit an afferent stimulation signal to the brain stem and then, after a series of interneurons, the efferent signal is transmitted to the lacrimal gland through the parasympathetic and sympathetic nerves that innervate the gland and drive tear production and secretion (Ocul Surf 2004; 2:76-91). Damage to this neural circuit interrupts the normal regulation of lacrimal gland secretion and causes dry eye disease. A reduction in neural drive from the cornea favors the occurrence of dry eye-associated ocular surface disease in two ways; first, by decreasing reflex-induced lacrimal secretion and by reducing the blink rate and, consequently, increasing evaporative loss; second, by decreasing the trophic factors to the epithelial layer. Damage to the sensory nerves in the ocular surface, particularly the cornea, as a consequence of refractive surgery and normal aging, prevents the normal reflex arc to the lacrimal gland and can result in decreased tear secretion and dry eye syndromes. Evidence for this mechanism comes from the clinical observation that dry eye syndrome frequently occurs after corneal refractive surgery. Clinical studies confirmed that tear production and secretion are reduced after LASIK surgery (Ophthalmology 2001; 108:1230-5). Hyposecretion of tears in dry eye may lead to pathologic alterations in corneal nerves and a decline in corneal sensitivity which subsequently perpetuate the dry eye state (Cornea 1996; 15:235-9).

Corneal Pathology

Ocular diseases that affect the corneal epithelium such as dry eye, exposure keratopathy, and other ocular surface diseases cause corneal nerve degeneration. On the other hand, normal neural drive is an essential requirement for corneal epithelium to heal and maintain its homeostasis. Therefore, corneal nerve alterations, either as a primary reason (refractive surgery) or just as the outcome of dryness and other corneal epithelial or ocular surface diseases, have crucial effects on the homeostasis of corneal epithelium, thus neatly contributing to the increase of the vicious circle of epithelial disease and nerve damage.

The Relationship Between Corneal Epithelial Disease and Corneal Nerve Damage

Figure 13:
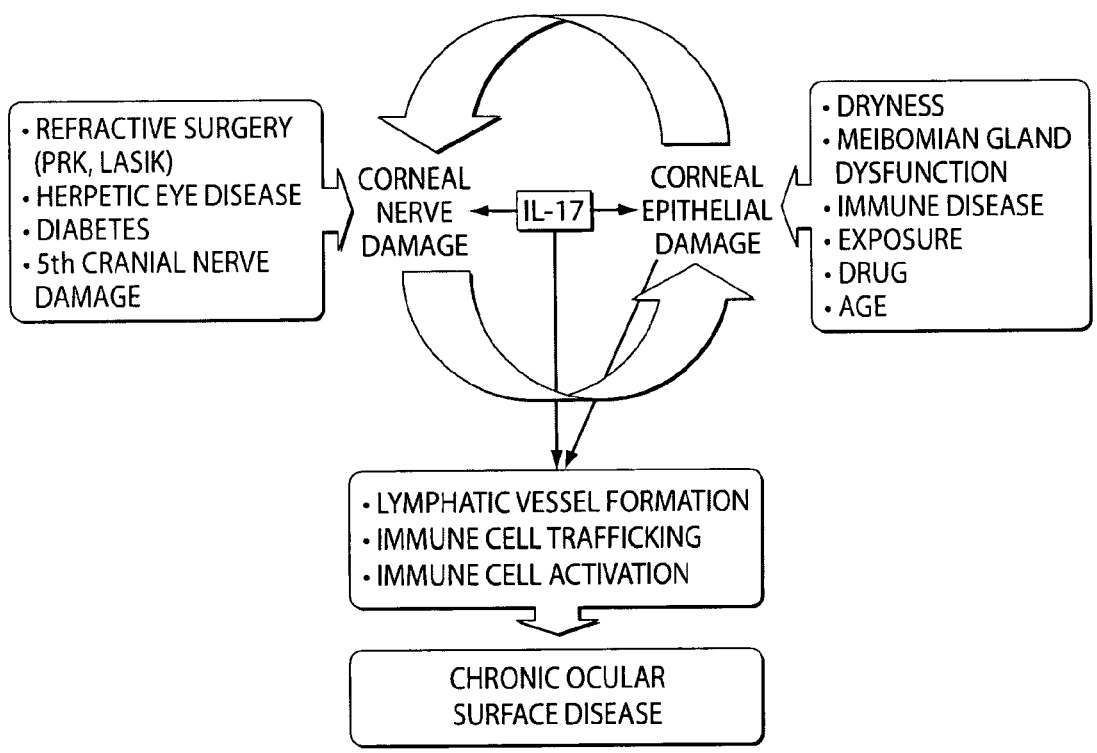
FIG. 13 is a schematic representation of the vicious circle of epithelial disease to nerve damage. IL-17 mediates corneal epithelial cell and nerve damage. Nerve damage can in turn exacerbate epithelial disease by lower provision of trophic factors necessary for epithelial cell health. The resultant increased level of inflammation and IL-17 overexpression also leads to lymphatic vessel invasion or growth into the cornea and the activation of immune cells, allowing the immune cells easier access from the cornea to the lymphoid compartment where autoimmunity is generated and chronic diseases sustained.

Ocular diseases that affect the corneal epithelium such as dry eye, exposure keratopathy, and other ocular surface diseases cause corneal nerve degeneration. On the other hand, normal neural drive and function are essential requirements for corneal epithelial healing and the maintenance of corneal homeostasis. Therefore, corneal nerve damage, either as a primary reason (inflicted by refractory surgery, herpetic eye disease, diabetes, or trigeminal nerve damage, e.g. fifth cranial nerve damage) or as a secondary outcome of dryness and other corneal epithelial or ocular surface diseases, can cause further damage to the corneal epithelium, thus contributing to the increase of the vicious circle of epithelial disease and nerve damage. In addition, IL-1 and corneal epithelial disease induce lymphatic vessel formation in the cornea. These lymphatic vessels are crucial for migration of resident and infiltrating antigen presenting cells and other immune cells, and drainage of corneal antigens, to the lymphoid compartment including draining lymph nodes and induction of adaptive immunity at the ocular surface, which ultimately leads to persistent and chronic ocular surface disease (see FIG. 13).

The Relationship Between Corneal Lymphatics and Inflammation

The normal human cornea has no lymphatic vessels. However in pathological conditions such as corneal epithelial disease, IL-17 induces lymphatic vessel formation in the cornea. These lymphatic vessels are crucial for migration of resident and infiltrating antigen presenting cells and other immune cells, and drainage of corneal antigens, to the lymphoid compartment including draining lymph nodes and induction of adaptive immunity against ocular surface, which ultimately leads to persistent and chronic ocular surface disease (see FIG. 13). In addition, corneal lymphatics play an important role in the induction of alloimmune response to corneal grafts in transplantations. The existence of corneal lymphatic vessels leads to increased rate of transplant rejections. Therapeutic inhibition of corneal lymphatics may thus enhance corneal transplant survival both in the high- and low-risk recipients.

Interleukin-17 (IL-17):

Interleukin-17 (IL-17) is a potent proinflammatory cytokine produced by a new lineage of CD4⁺ T cells (Th17). IL-17 signals through a heteromeric receptor complex composed of IL-17RA and IL-17RC. IL-17 has pleiotropic effects on several immune and non-immune cells, providing an association between T cell activation and the inflammatory response. Furthermore, IL-17 cooperates either additively or synergistically with other proinflammatory cytokines such as TNFα, IL1β or IL6, leading to amplification of inflammatory processes. IL-17, also known as IL-17A, is part of a larger family comprising 6 cytokines, referred to as IL-17A, IL-17B, IL-17C, IL-17D, IL-17E, and IL-17F. All members of this family share a common protein structure. Among these family members, IL-17A and IL-17F are most frequently expressed in immune cells. In alternative embodiments of the invention, one or more of these family members are targeted by antagonists to inhibit or modify their activity.

The invention comprises compositions with means to inhibit or modify the activity of human IL-17, defined as the ability of this protein to bind an IL-17 receptor. Compositions that comprise an inhibitor of human IL-17 function antagonize the activity of an IL-17 receptor. The composition comprises a polynucleotide, a polypeptide, an antibody, a compound, or a small molecule, or a fragment thereof, with means to inhibit or modify the transcription, transcript stability, translation, modification, localization, secretion, or function of a polynucleotide or polypeptide encoding human IL-17. In a preferred embodiment, the inhibitory composition binds to one or more region(s)/fragment(s) of IL-17 comprised by SEQ ID NO: 1 and SEQ ID NO: 2.

A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence, which is intermediate between the extremes defined above.

Human IL-17 is encoded by the following mRNA sequence (NCBI Accession No. NM_002190, alternatively called IL-17A, and SEQ ID NO: 1): (For all mRNA transcripts incorporated into the present application, the initiator methionine, encoded by the codon "atg," is bolded and capitalized to delineate the start of the coding region.)

```
  1 gcaggcacaa actcatccat ccccagttga ttggaagaaa caacgATGac tcctgggaag 61 acctcattgg tgtcactgct actgctgctg agcctggagg ccatagtgaa ggcaggaatc 121 acaatcccac gaaatccagg atgcccaaat tctgaggaca agaacttccc ccggactgtg 181 atggtcaacc tgaacatcca taaccggaat accaatacca atcccaaaag gtcctcagat 241 tactacaacc gatccacctc accttggaat ctccaccgca atgaggaccc tgagagatat 301 ccctctgtga tctgggaggc aaagtgccgc cacttgggct gcatcaacgc tgatgggaac 361 gtggactacc acatgaactc tgtccccatc cagcaagaga tcctggtcct gcgcagggag
```

-continued

```
 421 cctccacact gccccaactc cttccggctg gagaagatac tggtgtccgt gggctgcacc 481 tgtgtcaccc cgattgtcca ccatgtggcc taagagctct ggggagccca cactccccaa 541 agcagttaga ctatggagag ccgacccagc ccctcaggaa ccctcatcct tcaaagacag 601 cctcatttcg gactaaactc attagagttc ttaaggcagt ttgtccaatt aaagcttcag 661 aggtaacact tggccaagat atgagatctg aattaccttt ccctctttcc aagaaggaag 721 gtttgactga gtaccaattt gcttcttgtt tacttttta agggctttaa gttatttatg 781 tatttaatat gccctgagat aactttgggg tataagattc cattttaatg aattacctac 841 tttattttgt ttgtcttttt aaagaagata agattctggg cttgggaatt ttattattta 901 aaaggtaaaa cctgtattta tttgagctat ttaaggatct atttatgttt aagtatttag 961 aaaaaggtga aaaagcacta ttatcagttc tgcctaggta aatgtaagat agaattaaat 1021 ggcagtgcaa aatttctgag tctttacaac atacggatat agtatttcct cctctttgtt 1081 tttaaaagtt ataacatggc tgaaaagaaa gattaaacct actttcatat gtattaattt 1141 aaattttgca atttgttgag gttttacaag agatacagca agtctaactc tctgttccat 1201 taaacccctta aataaaaatc cttctgtaat aataaagttt caaaagaaaa tgtttatttg 1261 ttctcattaa atgtattttta gcaaactcag ctcttcccta ttgggaagag ttatgcaaat 1321 tctcctataa gcaaaacaaa gcatgtcttt gagtaacaat gacctggaaa tacccaaaat 1381 tccaagttct cgatttcaca tgccttcaag actgaacacc gactaaggtt ttcatactat 1441 tagccaatgc tgtagacaga agcattttga taggaataga gcaaataaga taatggccct 1501 gaggaatggc atgtcattat taaagatcat atggggaaaa tgaaaccctc cccaaaatac 1561 aagaagttct ggggaggagac attgtcttca gactacaatg tccagtttct cccctagact 1621 caggcttcct ttggagatta aggcccctca gagatcaaca gaccaacatt tttctcttcc 1681 tcaagcaaca ctcctagggc ctggcttctg tctgatcaag gcaccacaca acccagaaag 1741 gagctgatgg ggcagaacga actttaagta tgagaaaagt tcagcccaag taaaataaaa 1801 actcaatcac attcaattcc agagtagttt caagtttcac atcgtaacca ttttcgccc
```

Human IL-17 is encoded by the following amino acid sequence (NCBI Accession No. NM_002190, alternatively called IL-17A, and SEQ ID NO: 2):

MTPGKTSLVSLLLLLSLEAIVKAGITIPRNPGCPNSEDKNFPRTVMVNL
NIHNRNTNTNPKRSSDYYNRSTSPWNLHRNEDPERYPSVIWEAKCRHLG

-continued

CINADGNVDYHMNSVPIQQEILVLRREPPHCPNSFRLEKILVSVGCTCV
TPIVHHVA.

Human IL-17B is encoded by the following mRNA sequence (NCBI Accession No. NM_014443 and SEQ ID NO: 3):

```
  1 tggggttcca ggcgggcagc agctgcaggc tgaccttgca gcttggcgga ATGgactggc 61 ctcacaacct gctgtttctt cttaccattt ccatcttcct ggggctgggc cagcccagga 121 gccccaaaag caagaggaag gggcaagggc ggcctgggcc cctggcccct ggccctcacc 181 aggtgccact ggacctggtg tcacggatga accgtatgc ccgcatggag gagtatgaga 241 ggaacatcga ggagatggtg gcccagctga ggaacagctc agagctggcc cagagaaagt 301 gtgaggtcaa cttgcagctg tggatgtcca acaagaggag cctgtctccc tggggctaca 361 gcatcaacca cgaccccagc cgtatccccg tggacctgcc ggaggcacgg tgcctgtgtc 421 tgggctgtgt gaacccttc accatgcagg aggaccgcag catggtgagc gtgccggtgt 481 tcagccaggt tcctgtgcgc cgccgcctct gcccgccacc gccccgcaca gggccttgcc 541 gccagcgcgc agtcatggag accatcgctg tgggctgcac ctgcatcttc tgaatcacct
```

```
601 ggcccagaag ccaggccagc agcccgagac catcctcctt gcacctttgt gccaagaaag
661 gcctatgaaa agtaaacact gactttgaa agcaaaaaaa aaaaaaaaa a
```

Human IL-17B is encoded by the following amino acid sequence (NCBI Accession No. NM_014443 and SEQ ID NO: 4):

MDWPHNLLFLLTISIFLGLGQPRSPKSKRKGQGRPGPLAPGPHQVPLD
LVSRMKPYARMEEYERNIEEMVAQLRNSSELAQRKCEVNLQLWMSNKR
SLSPWGYSINHDPSRIPVDLPEARCLCLGCVNPFTMQEDRSMVSVPVF
SQVPVRRRLCPPPPRTGPCRQRAVMETIAVGCTCIF

Human IL-17C is encoded by the following mRNA sequence (NCBI Accession No. NM_013278 and SEQ ID NO: 5):

```
   1 gccaggtgtg caggccgctc aagcccagc ctgccccgct gccgccacca tgacgctcct
  61 ccccggcctc ctgtttctga cctggctgca cacatgcctg gcccaccatg acccctccct
 121 caggggggcac ccccacagtc acggtacccc acactgctac tcggctgagg aactgcccct
 181 cggccaggcc ccccacacc tgctggctcg aggtgccaag tggggggcagg cttttgcctgt
 241 agccctggtg tccagcctgg aggcagcaag ccacagggggg aggcacgaga ggccctcagc
 301 tacgacccag tgcccggtgc tgcggccgga ggaggtgttg gaggcagaca cccaccagcg
 361 ctccatctca ccctggagat accgtgtgga cacggatgag gaccgctatc cacagaagct
 421 ggccttcgcc gagtgcctgt gcagaggctg tatcgatgca cggacgggcc gcgagacagc
 481 tgcgctcaac tccgtgcggc tgctccagag cctgctggtg ctgcgccgcc ggccctgctc
 541 ccgcgacggc tcggggctcc ccacacctgg gccttttgcc ttccacaccg agttcatcca
 601 cgtccccgtc ggctgcacct gcgtgctgcc ccgttcagtg tgaccgccga ggccgtgggg
 661 cccctagact ggacacgtgt gctccccaga gggcaccccc tatttatgtg tatttattgt
 721 tatttatatg cctcccccaa cactacccttt ggggtctggg cattccccgt gtctggagga
 781 cagcccccca ctgttctcct catctccagc ctcagtagtt gggggtagaa ggagctcagc
 841 acctcttcca gcccttaaag ctgcagaaaa ggtgtcacac ggctgcctgt accttggctc
 901 cctgtcctgc tcccggcttc ccttacccta tcactggcct caggccccg caggctgcct
 961 cttcccaacc tccttggaag taccctgtt tcttaaacaa ttatttaagt gtacgtgtat
1021 tattaaactg atgaacacat ccccaaaa
```

Human IL-17C is encoded by the following amino acid sequence (NCBI Accession No. NM_013278 and SEQ ID NO: 6):

MTLLPGLLFLTWLHTCLAHHDPSLRGHPHSHGTPHCYSAEELPLGQAP
PHLLARGAKWGQALPVALVSSLEAASHRGRHERPSATTQCPVLRPEEV
LEADTHQRSISPWRYRVDTDEDRYPQKLAFAECLCRGCIDARTGRETA
ALNSVRLLQSLLVLRRRPCSRDGSGLPTPGAFAFHTEFIHVPVGCTCV
LPRSV

Human IL-17D is encoded by the following mRNA sequence (NCBI Accession No. NM_138284 and SEQ ID NO: 7):

```
  1 aaaatgtttt cagctcctgg aggcgaaagg tgcagagtcg ctctgtgtcc gtgaggccgg
 61 gcggcgacct cgctcagtcg gcttctcggt ccgagtcccc gggtctggAT Gctggtagcc
```

-continued

```
 121 ggcttcctgc tggcgctgcc gccgagctgg gccgcgggcg ccccgagggc gggcaggcgc
 181 cccgcgcggc cgcggggctg cgcggaccgg ccggaggagc tactggagca gctgtacggg
 241 cgcctggcgg ccggcgtgct cagtgccttc caccacacgc tgcagctggg gccgcgtgag
 301 caggcgcgca acgcgagctg cccggcaggg ggcaggcccg ccgaccgccg cttccggccg
 361 cccaccaacc tgcgcagcgt gtcgccctgg gcctacagaa tctcctacga cccggcgagg
 421 tacccccaggt acctgcctga agcctactgc ctgtgccggg gctgcctgac cgggctgttc
 481 ggcgaggagg acgtgcgctt ccgcagcgcc cctgtctaca tgcccaccgt cgtcctgcgc
 541 cgcaccccccg cctgcgccgg cggccgttcc gtctacaccg aggcctacgt caccatcccc
 601 gtgggctgca cctgcgtccc cgagccggag aaggacgcag acagcatcaa ctccagcatc
 661 gacaaacagg gcgccaagct cctgctgggc cccaacgacg cgcccgctgg ccctgaggc
 721 cggtcctgcc ccgggaggtc tccccggccc gcatcccgag gcgcccaagc tggagccgcc
 781 tggagggctc ggtcggcgac ctctgaagag agtgcaccga gcaaaccaag tgccggagca
 841 ccagcgccgc ctttccatgg agactcgtaa gcagcttcat ctgacacggg catccctggc
 901 ttgcttttag ctacaagcaa gcagcgtggc tggaagctga tgggaaacga cccggcacgg
 961 gcatcctgtg tgcggcccgc atggagggtt tggaaaagtt cacggaggct ccctgaggag
1021 cctctcagat cggctgctgc gggtgcaggg cgtgactcac cgctgggtgc ttgccaaaga
1081 gatagggacg catatgcttt ttaaagcaat ctaaaaataa taataagtat agcgactata
1141 tacctacttt taaaatcaac tgttttgaat agaggcagag ctattttata ttatcaaatg
1201 agagctactc tgttacattt cttaacatat aaacatcgtt ttttacttct tctggtagaa
1261 ttttttaaag cataattgga atccttggat aaattttgta gctggtacac tctggcctgg
1321 gtctctgaat tcagcctgtc accgatggct gactgatgaa atggacacgt ctcatctgac
1381 ccactcttcc ttccactgaa ggtcttcacg ggcctccagg tggaccaaag ggatgcacag
1441 gcggctcgca tgccccaggg ccagctaaga gttccaaaga tctcagattt ggttttagtc
1501 atgaatacat aaacagtctc aaactcgcac aatttttttcc cccttttgaa agccactggg
1561 gccaatttgt ggttaagagg tggtgagata agaagtggaa cgtgacatct ttgccagttg
1621 tcagaagaat ccaagcaggt attggcttag ttgtaagggc tttaggatca ggctgaatat
1681 gaggacaaag tgggccacgt tagcatctgc agagatcaat ctggaggctt ctgtttctgc
1741 attctgccac gagagctagg tccttgatct tttctttaga ttgaaagtct gtctctgaac
1801 acaattattt gtaaaagtta gtagttcttt tttaaatcat taaaagaggc ttgctgaagg
1861 aaaaaaaaaa aaa
```

Human IL-17D is encoded by the following amino acid sequence (NCBI Accession No. NM_138284 and SEQ ID NO: 8)

MLVAGFLLALPPSWAAGAPRAGRRPARPRGCADRPEELLEQLYGRLAA
GVLSAFHHTLQLGPREQARNASCPAGGRPADRRFRPPTNLRSVSPWAY
RISYDPARYPRYLPEAYCLCRGCLTGLFGEEDVRFRSAPVYMPTVVLR
RTPACAGGRSVYTEAYVTIPVGCTCVPEPEKDADSINSSIDKQGAKLL
LGPNDAPAGP

Human IL-17E is encoded by the following mRNA sequence (NCBI Accession No. AF305200 and SEQ ID NO: 9):

```
  1 ggcttgctga aataaaatc aggactccta acctgctcca gtcagcctgc ttccacgagg
 61 cctgtcagtc agtgcccgac ttgtgactga gtgtgcagtg cccagcatgt accaggtcag
121 tgcagagggc tgcctgaggg ctgtgctgag agggagagga gcagagatgc tgctgagggt
```

```
181 ggagggaggc caagctgcca ggtttgggc tggggccaa gtggagtgag aaactgggat
241 cccagggga gggtgcagat gagggagcga cccagattag gtgaggacag ttctctcatt
301 agccttttcc tacaggtggt tgcattcttg gcaatggtca tgggaaccca cacctacagc
361 cactggccca gctgctgccc cagcaaaggg caggacacct ctgaggagct gctgaggtgg
421 agcactgtgc ctgtgcctcc cctagagcct gctaggccca accgccaccc agagtcctgt
481 agggccagtg aagatggacc cctcaacagc agggccatct cccctggag atatgagttg
541 gacagagact tgaaccggct ccccaggac ctgtaccacg cccgttgcct gtgcccgcac
601 tgcgtcagcc tacagacagg ctcccacatg accccgggg gcaactcgga gctgctctac
661 cacaaccaga ctgtcttcta caggcggcca tgccatggcg agaagggcac ccacaagggc
721 tactgcctgg agcgcaggct gtaccgtgtt tccttagctt gtgtgtgtgt gcggccccgt
781 gtgatgggct agccggacct gctggaggct ggtccctttt tgggaaacct ggagccaggt
841 gtacaaccac ttgccatgaa gggccaggat gcccagatgc ttggcccctg tgaagtgctg
901 tctggagcag caggatcccg gacaggatg ggggctttg gggaaaacct gcacttctgc
961 acattttgaa aagagcagct gctgcttagg gccgccggaa gctggtgtcc tgtcattttc
1021 tctcaggaaa ggttttcaaa gttctgccca tttctggagg ccaccactcc tgtctcttcc
1081 tcttttccca tcccctgcta ccctggccca gcacaggcac tttctagata tttcccctt
1141 gctggagaag aaagagcccc tggttttatt tgtttgttta ctcatcactc agtgagcatc
1201 tactttgggt gcattctagt gtagttacta gtcttttgac atggatgatt ctgaggagga
1261 agctgttatt gaatgtatag agatttatcc aaataaatat ctttatttaa aaatgaaaaa
1321 aaaaaaaaaa aaaaa
```

Human IL-17E is encoded by the following amino acid sequence (NCBI Accession No. AF305200 and SEQ ID NO: 10):

MRERPRLGEDSSLISLFLQVVAFLAMVMGTHTYSHWPSCCPSKGQDTS
EELLRWSTVPVPPLEPARPNRHPESCRASEDGPLNSRAISPWRYELDR
DLNRLPQDLYHARCLCPHCVSLQTGSHMDPRGNSELLYHNQTVFYRRP
CHGEKGTHKGYCLERRLYRVSLACVCVRPRVMG

Human IL-17F is encoded by the following mRNA sequence (NCBI Accession No. NM_052872 and SEQ ID NO: 11):

```
  1 gaacacaggc atacacagga agatacattc acagaaagag cttcctgcac aaagtaagcc
 61 accagcgcaa cATGacagtg aagaccctgc atggcccagc catggtcaag tacttgctgc
121 tgtcgatatt ggggcttgcc tttctgagtg aggcggcagc tcggaaaatc cccaaagtag
181 gacatacttt tttccaaaag cctgagagtt gcccgcctgt gccaggaggt agtatgaagc
241 ttgacattgg catcatcaat gaaaaccagc gcgtttccat gtcacgtaac atcgagagcc
301 gctccacctc cccctggaat tacactgtca cttgggaccc caaccggtac ccctcggaag
361 ttgtacaggc ccagtgtagg aacttgggct gcatcaatgc tcaaggaaag gaagacatct
421 ccatgaattc cgttcccatc cagcaagaga ccctggtcgt ccggaggaag caccaaggct
481 gctctgtttc tttccagttg gagaaggtgc tggtgactgt tggctgcacc tgcgtcaccc
541 ctgtcatcca ccatgtgcag taagaggtgc atatccactc agctgaagaa gctgtagaaa
601 tgccactcct tacccagtgc tctgcaacaa gtcctgtctg accccaatt ccctccactt
661 cacaggactc ttaataagac ctgcacggat ggaaacagaa atattcaca atgtatgtgt
721 gtatgtacta cactttatat ttgatatcta aaatgttagg agaaaatta atatattcag
781 tgctaatata ataaagtatt aataattt
```

Human IL-17F is encoded by the following amino acid sequence (NCBI Accession No. NM_052872 and SEQ ID NO: 12)

MTVKTLHGPAMVKYLLLSILGLAFLSEAAARKIPKVGHTFFQKPESCP

PVPGGSMKLDIGIINENQRVSMSRNIESRSTSPWNYTVTWDPNRYPSE

VVQAQCRNLGCINAQGKEDISMNSVPIQQETLVVRRKHQGCSVSFQLE

KVLVTVGCTCVTPVIHHVQ

Interleukin-17 Receptors:

The composition of the invention comprises a polynucleotide, a polypeptide, an antibody, a compound, or a small molecule, or fragment thereof, with means to inhibit or modify the transcription, transcript stability, translation, modification, localization, secretion, or function of a polynucleotide or polypeptide encoding an IL-17 receptor. One contemplated IL-17 heteromeric receptor complex comprises IL-17RA and IL-17RC. The present composition comprises a compound that is targeted to either element, IL-17RA or IL-17RC, of this receptor complex. IL-17RC exists in three different forms comprised by transcripts 1-3. However, additional IL-17 receptors are contemplated. In alternative embodiments, IL-17RB, IL-17RD, and IL-17RE are targeted in isolation or in combination by antagonists of IL-17 function. The invention comprises one or more antagonists of IL-17 receptors IL-17RA, IL-17RB, IL-17RC, IL-17RD, and IL-17RE.

IL-17RA is encoded by the following mRNA sequence (NCBI Accession No. NM_014339 and SEQ ID NO: 13):

```
   1 ctgggcccgg gctggaagcc ggaagcgagc aaagtggagc cgactcgaac tccaccgcgg
  61 aaaagaaagc ctcagaacgt tcgttcgctg cgtccccagc cggggccgag ccctccgcga
 121 cgccagccgg gccATGgggg ccgcacgcag cccgccgtcc gctgtcccgg ggcccctgct
 181 ggggctgctc ctgctgctcc tgggcgtgct ggccccgggt ggcgcctccc tgcgactcct
 241 ggaccaccgg gcgctggtct gctcccagcc ggggctaaac tgcacggtca agaatagtac
 301 ctgcctggat gacagctgga ttcaccctcg aaacctgacc cctcctccc caaaggacct
 361 gcagatccga ctgcactttg cccacaccca acaaggagac ctgttccccg tggctcacat
 421 cgaatggaca ctgcagacag acgccagcat cctgtacctc gagggtgcag agttatctgt
 481 cctgcagctg aacaccaatg aacgtttgtg cgtcaggttt gagtttctgt ccaaactgag
 541 gcatcaccac aggcggtggc gttttacctt cagccacttt gtggttgacc ctgaccagga
 601 atatgaggtg accgttcacc acctgcccaa gccatccct gatggggacc caaaccacca
 661 gtccaagaat ttccttgtgc ctgactgtga gcacgccagg atgaaggtaa ccacgccatg
 721 catgagctca ggcagcctgt gggacccaa catcaccgtg gagaccctgg aggcccacca
 781 gctgcgtgtg agcttcaccc tgtggaacga atctacccat taccagatcc tgctgaccag
 841 ttttccgcac atggagaacc acagttgctt tgagcacatg caccacatac ctgcgcccag
 901 accagaagag ttccaccagc gatccaacgt cacactcact ctacgcaacc ttaaagggtg
 961 ctgtcgccac caagtgcaga tccagccctt cttcagcagc tgcctcaatg actgcctcag
1021 acactccgcg actgtttcct gcccagaaat gccagacact ccagaaccaa ttccggacta
1081 catgcccctg tgggtgtact ggttcatcac gggcatctcc atcctgctgg tgggctccgt
1141 catcctgctc atcgtctgca tgacctggag gctagctggg cctggaagtg aaaaatacag
1201 tgatgacacc aaatacaccg atggcctgcc tgcggctgac ctgatccccc caccgctgaa
1261 gcccaggaag gtctggatca tctactcagc cgaccacccc ctctacgtgg acgtggtcct
1321 gaaattcgcc cagttcctgc tcaccgcctg cggcacggaa gtggccctgg acctgctgga
1381 agagcaggcc atctcggagg caggagtcat gacctgggtg ggccgtcaga gcaggagat
1441 ggtggagagc aactctaaga tcatcgtcct gtgctcccgc ggcacgcgcg ccaagtggca
1501 ggcgctcctg ggccgggggg cgcctgtgcg gctgcgctgc gaccacggaa gcccgtggg
1561 ggacctgttc actgcagcca tgaacatgat cctcccggac ttcaagaggc cagcctgctt
1621 cggcacctac gtagtctgct acttcagcga ggtcagctgt gacggcgacg tccccgacct
1681 gttcggcgcg cgccgcgcgt acccgctcat ggacaggttc gaggaggtgt acttccgcat
1741 ccaggaccct gagatgttcc agccgggccg catgcaccgc gtaggggagc tgtcggggga
```

```
1801 caactacctg cggagcccgg gcggcaggca gctccgcgcc gccctggaca ggttccggga
1861 ctggcaggtc cgctgtcccg actggttcga atgtgagaac ctctactcag cagatgacca
1921 ggatgccccg tccctggacg aagaggtgtt tgaggagcca ctgctgcctc cgggaaccgg
1981 catcgtgaag cgggcgcccc tggtgcgcga gcctggctcc caggcctgcc tggccataga
2041 cccgctggtc ggggaggaag gaggagcagc agtggcaaag ctggaacctc acctgcagcc
2101 ccggggtcag ccagcgccgc agcccctcca cccctggtg ctcgccgcag aggaggggc
2161 cctggtggcc gcggtggagc ctgggcccct ggctgacggt gccgcagtcc ggctggcact
2221 ggcgggggag ggcgaggcct gcccgctgct gggcagcccg ggcgctgggc gaaatagcgt
2281 cctcttcctc cccgtggacc ccgaggactc gccccttggc agcagcaccc ccatggcgtc
2341 tcctgacctc cttccagagg acgtgaggga gcacctcgaa ggcttgatgc tctcgctctt
2401 cgagcagagt ctgagctgcc aggcccaggg gggctgcagt agacccgcca tggtcctcac
2461 agacccacac acgccctacg aggaggagca gcggcagtca gtgcagtctg accagggcta
2521 catctccagg agctccccgc agccccccga gggactcacg gaaatggagg aagaggagga
2581 agaggagcag gacccaggga agccggcccc gccactctct cccgaggacc tggagagcct
2641 gaggagcctc cagcggcagc tgcttttccg ccagctgcag aagaactcgg gctgggacac
2701 gatggggtca gagtcagagg ggcccagtgc atgagggcgg ctccccaggg accgcccaga
2761 tcccagcttt gagagaggag tgtgtgtgca cgtattcatc tgtgtgtaca tgtctgcatg
2821 tgtatatgtt cgtgtgtgaa atgtaggctt taaaatgtaa atgtctggat tttaatccca
2881 ggcatccctc ctaactttc tttgtgcagc ggtctggtta tcgtctatcc ccaggggaat
2941 ccacacagcc cgctcccagg agctaatggt agagcgtcct tgaggctcca ttattcgttc
3001 attcagcatt tattgtgcac ctactatgtg gcgggcattt gggataccaa gataaattgc
3061 atgcggcatg gccccagcca tgaaggaact taaccgctag tgccgaggac acgttaaacg
3121 aacaggatgg gccgggcacg gtggctcacg cctgtaatcc cagcacactg ggaggccgag
3181 gcaggtggat cactctgagg tcaggagttt gagccagcct ggccaacatg gtgaaacccc
3241 atctccacta aaaatagaaa aattagccgg gcatggtgac acatgcctgt agtcctagct
3301 acttgggagg ctgaggcagg agaattgctt gaatctggga ggcagaggtt gcagtgagcc
3361 gagattgtgc cattgcactg cagcctggat gacagagcga gactctatct caaaaaaaaa
3421 aaaaaaaaa
```

IL-17RA is encoded by the following amino acid sequence (NCBI Accession No. NM_14339 and SEQ ID NO: 14):

MGAARSPPSAVPGPLLGLLLLLLGVLAPGGASLRLLDHRALVCSQPGL
NCTVKNSTCLDDSWIHPRNLTPSSPKDLQIQLHFAHTQQGDLFPVAHI
EWTLQTDASILYLEGAELSVLQLNTNERLCVRFEFLSKLRHHHRRWRF
TFSHFVVDPDQEYEVTVHHLPKPIPDGDPNHQSKNFLVPDCEHARMKV
TTPCMSSGSLWDPNITVETLEAHQLRVSFTLWNESTHYQILLTSFPHM
ENHSCFEHMHHIPAPRPEEFHQRSNVTLTLRNLKGCCRHQVQIQPFFS
SCLNDCLRHSATVSCPEMPDTPEPIPDYMPLWVYWFITGISILLVGSV
ILLIVCMTWRLAGPGSEKYSDDTKYTDGLPAADLIPPPLKPRKVWIIY
SADHPLYVDVVLKFAQFLLTACGTEVALDLLEEQAISEAGVMTWVGRQ
KQEMVESNSKIIVLCSRGTRAKWQALLGRGAPVRLRCDHGKPVGDLFT
AAMNMILPDFKRPACFGTYVVCYFSEVSCDGDVPDLFGAAPRYPLMDR
FEEVYFRIQDLEMFQPGRMHRVGELSGDNYLRSPGGRQLRAALDRFRD
WQVRCPDWFECENLYSADDQDAPSLDEEVFEEPLLPPGTGIVKRAPLV
REPGSQACLAIDPLVGEEGGAAVAKLEPHLQPRGQPAPQPLHTLVLAA
EEGALVAAVEPGPLADGAAVRLALAGEGEACPLLGSPGAGRNSVLFLP
VDPEDSPLGSSTPMASPDLLPEDVREHLEGLMLSLFEQSLSCQAQGGC
SRPAMVLTDPHTPYEEEQRQSVQSDQGYISRSSPQPPEGLTEMEEEEE
EEQDPGKPALPLSPEDLESLRSLQRQLLFRQLQKNSGWDTMGSESEGP
SA

IL-17RB is encoded by the following mRNA sequence (NCBI Accession No. NM_018725 and SEQ ID NO: 15):

```
   1 agcgtgcggg tggcctggat cccgcgcagt ggcccggcgA TGtcgctcgt gctgctaagc
  61 ctggccgcgc tgtgcaggag cgccgtaccc cgagagccga ccgttcaatg tggctctgaa
 121 actgggccat ctccagagtg gatgctacaa catgatctaa tccccggaga cttgagggac
 181 ctccgagtag aacctgttac aactagtgtt gcaacagggg actattcaat tttgatgaat
 241 gtaagctggg tactccgggc agatgccagc atccgcttgt tgaaggccac caagatttgt
 301 gtgacgggca aaagcaactt ccagtcctac agctgtgtga ggtgcaatta cacagaggcc
 361 ttccagactc agaccagacc ctctggtggt aaatggacat tttcctacat cggcttccct
 421 gtagagctga acacagtcta tttcattggg gcccataata ttcctaatgc aaatatgaat
 481 gaagatggcc cttccatgtc tgtgaatttc acctcaccag gctgcctaga ccacataatg
 541 aaatataaaa aaaagtgtgt caaggccgga agcctgtggg atccgaacat cactgcttgt
 601 aagaagaatg aggagacagt agaagtgaac ttcacaacca ctcccctggg aaacagatac
 661 atggctctta tccaacacag cactatcatc gggttttctc aggtgtttga gccacaccag
 721 aagaaacaaa cgcgagcttc agtggtgatt ccagtgactg gggatagtga aggtgctacg
 781 gtgcagctga ctccatattt tcctacttgt ggcagcgact gcatccgaca taaaggaaca
 841 gttgtgctct gcccacaaac aggcgtccct ttccctctgg ataacaacaa aagcaagccg
 901 ggaggctggc tgcctctcct cctgctgtct ctgctggtgg ccacatgggt gctggtggca
 961 gggatctatc taatgtggag gcacgaaagg atcaagaaga cttcctttc taccaccaca
1021 ctactgcccc ccattaaggt tcttgtggtt tacccatctg aaatatgttt ccatcacaca
1081 atttgttact tcactgaatt tcttcaaaac cattgcagaa gtgaggtcat ccttgaaaag
1141 tggcagaaaa agaaaatagc agagatgggt ccagtgcagt ggcttgccac tcaaaagaag
1201 gcagcagaca aagtcgtctt ccttctttcc aatgacgtca acagtgtgtg cgatggtacc
1261 tgtggcaaga gcgagggcag tcccagtgag aactctcaag acctcttccc ccttgccttt
1321 aaccttttct gcagtgatct aagaagccag attcatctgc acaaatacgt ggtggtctac
1381 tttagagaga ttgatacaaa agacgattac aatgctctca gtgtctgccc caagtaccac
1441 ctcatgaagg atgccactgc tttctgtgca gaacttctcc atgtcaagca gcaggtgtca
1501 gcaggaaaaa gatcacaagc ctgccacgat ggctgctgct ccttgtagcc cacccatgag
1561 aagcaagaga ccttaaaggc ttcctatccc accaattaca gggaaaaaac gtgtgatgat
1621 cctgaagctt actatgcagc ctacaaacag ccttagtaat taaacatttt tataccaata
1681 aaattttcaa atattgctaa ctaatgtagc attaactaac gattggaaac tacatttaca
1741 acttcaaagc tgttttatac atagaaatca attacagttt taattgaaaa ctataaccat
1801 tttgataatg caacaataaa gcatcttcag ccaaacatct agtcttccat agaccatgca
1861 ttgcagtgta cccagaactg tttagctaat attctatgtt taattaatga atactaactc
1921 taagaacccc tcactgattc actcaatagc atcttaagtg aaaaaccttc tattacatgc
1981 aaaaaatcat tgttttttaag ataacaaaag tagggaataa acaagctgaa cccactttta
2041 aaaaaaaaaa aaaaaaaaaa aaaaaaaaa aa
```

IL-17RB is encoded by the following amino acid sequence (NCBI Accession No. NM_018725 and SEQ ID NO: 16):

MSLVLLSLAALCRSAVPREPTVQCGSETGPSPEWMLQHDLIPGDLRDL

RVEPVTTSVATGDYSILMNVSWVLRADASIRLLKATKICVTGKSNFQS

YSCVRCNYTEAFQTQTRPSGGKWTFSYIGFPVELNTVYFIGAHNIPNA

NMNEDGPSMSVNFTSPGCLDHIMKYKKKCVKAGSLWDPNITACKKNEE

TVEVNFTTTPLGNRYMALIQHSTIIGFSQVFEPHQKKQTRASVVIPVT

GDSEGATVQLTPYFPTCGSDCIRHKGTVVLCPQTGVPFPLDNNKSKPG

GWLPLLLLSLLVATWVLVAGIYLMWRHERIKKTSFSTTTLLPPIKVLV

VYPSEICFHHTICYFTEFLQNHCRSEVILEKWQKKKIAEMGPVQWLAT

QKKAADKVVFLLSNDVNSVCDGTCGKSEGSPSENSQDLFPLAFNLFCS

DLRSQIHLHKYVVVYFREIDTKDDYNALSVCPKYHLMKDATAFCAELL

HVKQQVSAGKRSQACHDGCCSL

IL-17RC, transcript variant 1, is encoded by the following mRNA sequence (NCBI Accession No. NM_153461 and SEQ ID NO: 17):

```
   1 aaaacgaaag cactccgtgc tggaagtagg aggagagtca ggactcccag gacagagagt
  61 gcacaaacta cccagcacag cccctccgc ccctctgga ggctgaagag ggattccagc
 121 ccctgccacc cacagacacg ggctgactgg ggtgtctgcc cccttgggg ggggcagca
 181 cagggcctca ggctgggtg ccacctggca cctagaagAT Gcctgtgccc tggttcttgc
 241 tgtccttggc actgggccga agcccagtgg tcctttctct ggagaggctt gtggggcctc
 301 aggacgctac ccactgctct ccggtgagtc tggaaccctg gggagacgag gaaaggctca
 361 gggttcagtt tttggctcag caaagcctta gcctggctcc tgtcactgct gccactgcca
 421 gaactgccct gtctggtctg tctggtgctg atggtagaag agaagaacgg ggaaggggca
 481 agagctgggg ctgtctttct ctgggagggt ctgggaatac ggagcccag aaaaagggcc
 541 tctcctgccg cctctgggac agtgacatac tctgcctgcc tggggacatc gtgcctgctc
 601 cgggccccgt gctggcgcct acgcacctgc agacagagct ggtgctgagg tgccagaagg
 661 agaccgactg tgacctctgt ctgcgtgtgg ctgtccactt ggccgtgcat gggcactggg
 721 aagagcctga agatgaggaa aagtttggag gagcagctga ctcaggggtg gaggagccta
 781 ggaatgcctc tctccaggcc caagtcgtgc tctccttcca ggcctaccct actgcccgct
 841 gcgtcctgct ggaggtgcaa gtgcctgctg cccttgtgca gtttggtcag tctgtgggct
 901 ctgtggtata tgactgcttc gaggctgccc tagggagtga ggtacgaatc tggtcctata
 961 ctcagcccag gtacgagaag gaactcaacc acacacagca gctgcctgac tgcaggggc
1021 tcgaagtctg gaacagcatc ccgagctgct gggccctgcc ctggctcaac gtgtcagcag
1081 atggtgacaa cgtgcatctg gttctgaatg tctctgagga gcagcacttc ggcctctccc
1141 tgtactggaa tcaggtccag ggccccccaa aacccggtg gcacaaaaac ctgactggac
1201 cgcagatcat taccttgaac cacacagacc tggttccctg cctctgtatt caggtgtggc
1261 ctctggaacc tgactccgtt aggacgaaca tctgcccctt cagggaggac ccccgcgcac
1321 accagaacct ctggcaagcc gcccgactgc gactgctgac cctgcagagc tggctgctgg
1381 acgcaccgtg ctcgctgccc gcagaagcgg cactgtgctg gcgggctccg ggtggggacc
1441 cctgccagcc actggtccca ccgctttcct gggagaacgt cactgtggac aaggttctcg
1501 agttcccatt gctgaaaggc caccctaacc tctgtgttca ggtgaacagc tcggagaagc
1561 tgcagctgca ggagtgcttg tgggctgact ccctgggcc tctcaaagac gatgtgctac
1621 tgttggagac acgaggcccc caggacaaca gatccctctg tgccttggaa cccagtggct
1681 gtacttcact acccagcaaa gcctccacga gggcagctcg ccttggagag tacttactac
1741 aagacctgca gtcaggccag tgtctgcagc tatgggacga tgacttggga gcgctatggg
1801 cctgccccat ggacaaatac atccacaagc gctgggccct cgtgtggctg gcctgcctac
1861 tcttttgccgc tgcgcttttcc ctcatcctcc ttctcaaaaa ggatcacgcg aaagggtggc
```

```
1921 tgaggctctt gaaacaggac gtccgctcgg gggcggccgc caggggccgc gcggctctgc
1981 tcctctactc agccgatgac tcgggtttcg agcgcctggt gggcgccctg gcgtcggccc
2041 tgtgccagct gccgctgcgc gtggccgtag acctgtggag ccgtcgtgaa ctgagcgcgc
2101 aggggcccgg gcttggtttt cacgcgcagc ggcgccagac cctgcaggag ggcggcgtgg
2161 tggtcttgct cttctctccc ggtgcggtgg cgctgtgcag cgagtggcta caggatgggg
2221 tgtccgggcc cggggcgcac ggcccgcacg acgccttccg cgcctcgctc agctgcgtgc
2281 tgcccgactt cttgcagggc cgggcgcccg gcagctacgt gggggcctgc ttcgacaggc
2341 tgctccaccc ggacgccgta cccgcccttt tccgcaccgt gccctgcttc acactgccct
2401 cccaactgcc agacttcctg ggggccctgc agcagcctcg cgccccgcgt tccgggcggc
2461 tccaagagag agcggagcaa gtgtcccggg cccttcagcc agccctggat agctacttcc
2521 atccccgggg gactcccgcg ccgggacgcg gggtgggacc aggggcggga cctggggcgg
2581 gggacgggac ttaaataaag gcagacgctg tttttctacc catgtggccc aaaaaaaaaa
2641 aaaaaaaaaa aaaaaaaaaa aaaaaaaaaa aaaaaaaaaa aaaaaaaaaa a
```

IL-17RC, transcript variant 1, is encoded by the following amino acid sequence (NCBI Accession No. NM_153461 and SEQ ID NO: 18):

MPVPWFLLSLALGRSPVVLSLERLVGPQDATHCSPVSLEPWGDEERLR
VQFLAQQSLSLAPVTAATARTALSGLSGADGRREERGRGKSWVCLSLG
GSGNTEPQKKGLSCRLWDSDILCLPGDIVPAPGPVLAPTHLQTELVLR
CQKETDCDLCLRVAVHLAVHGHWEEPEDEEKFGGAADSGVEEPRNASL
QAQVVLSFQAYPTARCVLLEVQVPAALVQFGQSVGSVVYDCFEAALGS
EVRIWSYTQPRYEKELNHTQQLPDCRGLEVWNSIPSCWALPWLNVSAD
GDNVHLVLNVSEEQHFGLSLYWNQVQGPPKPRWHKNLTGPQIITLNHT
DLVPCLCIQVWPLEPDSVRTNICPFREDPRAHQNLWQAARLRLLTLQS
WLLDAPCSLPAEAALCWRAPGGDPCQPLVPPLSWENVTVDKVLEFPLL
KGHPNLCVQVNSSEKLQLQECLWADSLGPLKLDDVLLLETRGPQDNRS
LCALEPSGCTSLPSKASTRAARLGEYLLQDLQSGQCLQLWDDDLGALW
ACPMDKYIHKRWALVWLACLLFAAALSLILLLKKDHAKGWLRLLKQDV
RSGAAARGRAALLLYSADDSGFERLVGALASALCQLPLRVAVDLWSRR
ELSAQGPVAWFHAQRRQTLQEGGVVVLLFSPGAVALCSEWLQDGVSGP
GAHGPHDAFRASLSCVLPDFLQGRAPGSYVGACFDRLLHPDAVPALFR
TVPVFTLPSQLPDFLGALQQPRAPRSGRLQERAEQVSRALQPALDSYF
HPPGTPAPGRGVGPGAGPGAGDGT

IL-17RC, transcript variant 2, is encoded by the following mRNA sequence (NCBI Accession No. NM_153460 and SEQ ID NO: 19):

```
   1 aaaacgaaag cactccgtgc tggaagtagg aggagagtca ggactcccag gacagagagt
  61 gcacaaacta cccagcacag cccctccgc cccctctgga ggctgaagag ggattccagc
 121 ccctgccacc cacagacacg ggctgactgg ggtgtctgcc ccccttgggg gggggcagca
 181 cagggcctca ggcctgggtg ccacctggca cctagaagAT Gcctgtgccc tggttcttgc
 241 tgtccttggc actgggccga agcccagtgg tcctttctct ggagaggctt gtggggcctc
 301 aggacgctac ccactgctct ccgggcctct cctgccgcct ctgggacagt gacatactct
 361 gcctgcctgg ggacatcgtg cctgctccgg gccccgtgct ggcgcctacg cacctgcaga
 421 cagagctggt gctgaggtgc cagaaggaga ccgactgtga cctctgtctg cgtgtggctg
 481 tccacttggc cgtgcatggg cactgggaag agcctgaaga tgaggaaaag tttggaggag
 541 cagctgactc aggggtggag gagcctagga atgcctctct ccaggcccaa gtcgtgctct
 601 ccttccaggc ctaccctact gcccgctgcg tcctgctgga ggtgcaagtg cctgctgccc
 661 ttgtgcagtt tggtcagtct gtgggctctg tggtatatga ctgcttcgag gctgccctag
 721 ggagtgaggt acgaatctgg tcctatactc agcccaggta cgagaaggaa ctcaaccaca
 781 cacagcagct gcctgactgc agggggctcg aagtctggaa cagcatcccg agctgctggg
```

```
 841 ccctgccctg gctcaacgtg tcagcagatg gtgacaacgt gcatctggtt ctgaatgtct 901 ctgaggagca gcacttcggc ctctccctgt actggaatca ggtccagggc cccccaaaac 961 cccggtggca caaaaacctg actggaccgc agatcattac cttgaaccac acagacctgg 1021 ttccctgcct ctgtattcag gtgtggcctc tggaacctga ctccgttagg acgaacatct 1081 gccccttcag ggaggacccc cgcgcacacc agaacctctg gcaagccgcc cgactgcgac 1141 tgctgaccct gcagagctgg ctgctggacg caccgtgctc gctgcccgca gaagcggcac 1201 tgtgctggcg ggctccgggt ggggacccct gccagccact ggtcccaccg ctttcctggg 1261 agaacgtcac tgtggacaag gttctcgagt tcccattgct gaaaggccac cctaacctct 1321 gtgttcaggt gaacagctcg gagaagctgc agctgcagga gtgcttgtgg gctgactccc 1381 tggggcctct caaagacgat gtgctactgt tggagacacg aggcccccag gacaacagat 1441 ccctctgtgc cttggaaccc agtggctgta cttcactacc cagcaaagcc tccacgaggg 1501 cagctcgcct tggagagtac ttactacaag acctgcagtc aggccagtgt ctgcagctat 1561 gggacgatga cttgggagcg ctatgggcct gccccatgga caaatacatc cacaagcgct 1621 gggccctcgt gtggctggcc tgcctactct tgccgctgc gctttccctc atcctccttc 1681 tcaaaaagga tcacgcgaaa gggtggctga ggctcttgaa acaggacgtc cgctcggggg 1741 cggccgccag gggccgcgcg gctctgctcc tctactcagc cgatgactcg ggtttcgagc 1801 gcctggtggg cgccctggcg tcggccctgt gccagctgcc gctgcgcgtg gccgtagacc 1861 tgtggagccg tcgtgaactg agcgcgcagg gccccgtggc ttggtttcac gcgcagcggc 1921 gccagaccct gcaggagggc ggcgtggtgg tcttgctctt ctctcccggt gcggtggcgc 1981 tgtgcagcga gtggcacag gatggggtgt ccgggcccgg ggcgcacggc ccgcacgacg 2041 ccttccgcgc ctcgctcagc tgcgtgctgc ccgacttctt gcagggccgg gcgcccggca 2101 gctacgtggg ggcctgcttc gacaggctgc tccaccggga cgccgtaccc gccctttttcc 2161 gcaccgtgcc cgtcttcaca ctgccctccc aactgccaga cttcctgggg gccctgcagc 2221 agcctcgcgc cccgcgttcc gggcggctcc aagagagagc ggagcaagtg tcccgggccc 2281 ttcagccagc cctggatagc tacttccatc ccccggggac tccgcgccg ggacgcgggg 2341 tgggaccagg ggcgggacct ggggcggggg acgggactta aataaaggca gacgctgttt 2401 ttctaccat gtggcccaaa aaaaaaaaaa aaaaaaaaaa aaaaaaaaaa aaaaaaaaaa 2461 aaaaaaaaaa aaaaaaaa
```

IL-17RC, transcript variant 2, is encoded by the following amino acid sequence (NCBI Accession No. NM_153460 and SEQ ID NO: 20):

MPVPWFLLSLALGRSPVVLSLERLVGPQDATHCSPGLSCRLWDSDILCLP
GDIVPAPGPVLAPTHLQTELVLRCQKETDCDLCLRVAVHLAVHGHWEEPE
DEEKFGGAADSGVEEPRNASLQAQVVLSFQAYPTARCVLLEVQVPAALVQ
FGQSVGSVVYDCFEAALGSEVRIWSYTQPRYEKELNHTQQLPDCRGLEVW
NSIPSCWALPWLNVSADGDNVHLVLNVSEEQHFGLSLYWNQVQGPPKPRW
HKNLTGPQIITLNHTDLVPCLCIQVWPLEPDSVRTNICPFREDPRAHQNL
WQAARLRLLTLQSWLLDAPCSLPAEAALCWRAPGGDPCQPLVPPLSWENV
TVDKVLEFPLLKGHPNLCVQVNSSEKLQLQECLWADSLGPLKDDVLLLET
RGPQDNRSLCALEPSGCTSLPSKASTRAARLGEYLLQDLQSGQCLQLWDD
DLGALWACPMDKYIHKRWALVWLACLLFAAALSLILLLKKDHAKGWLRLL
KQDVRSGAAARGRAALLLYSADDSGFERLVGALASALCQLPLRVAVDLWS
RRELSAQGPVAWFHAQRRQTLQEGGVVVLLFSPGAVALCSEWLQDGVSGP
GAHGPHDAFRASLSCVLPDFLQGRAPGSYVGACFDRLLHPDAVPALFRTV
PVFTLPSQLPDFLGALQQPRAPRSGRLQERAEQVSRALQPALDSYFHPPG
TPAPGRGVGPGAGPGAGDGT

IL-17RC, transcript variant 3, is encoded by the following mRNA sequence (NCBI Accession No. NM_032732 and SEQ ID NO: 21):

```
   1 aaaacgaaag cactccgtgc tggaagtagg aggagagtca ggactcccag acagagagt
  61 gcacaaacta cccagcacag cccctccgc ccctctgga ggctgaagag ggattccagc
 121 ccctgccacc cacagacacg ggctgactgg ggtgtctgcc cccttgggg gggcagca
 181 cagggcctca ggcctgggtg ccacctggca cctagaagAT Gcctgtgccc tggttcttgc
 241 tgtccttggc actgggccga agcccagtgg tcctttctct ggagaggctt gtggggcctc
 301 aggacgctac ccactgctct ccgggcctct cctgccgcct ctgggacagt gacatactct
 361 gcctgcctgg ggacatcgtg cctgctccgg gccccgtgct ggcgcctacg cacctgcaga
 421 cagagctggt gctgaggtgc agaaggaga ccgactgtga cctctgtctg cgtgtggctg
 481 tccacttggc cgtgcatggg cactgggaag agcctgaaga tgaggaaaag tttggaggag
 541 cagctgactc aggggtggag gagcctagga atgcctctct ccaggcccaa gtcgtgctct
 601 ccttccaggc ctaccctact gcccgctgcg tcctgctgga ggtgcaagtg cctgctgccc
 661 ttgtgcagtt tggtcagtct gtgggctctg tggtatatga ctgcttcgag gctgccctag
 721 ggagtgaggt acgaatctgg tcctatactc agcccaggta cgagaaggaa ctcaaccaca
 781 cacagcagct gcctgccctg ccctggctca acgtgtcagc agatggtgac aacgtgcatc
 841 tggttctgaa tgtctctgag gagcagcact tcggcctctc cctgtactgg aatcaggtcc
 901 agggcccccc aaaaccccgg tggcacaaaa acctgactgg accgcagatc attaccttga
 961 accacacaga cctggttccc tgcctctgta ttcaggtgtg gcctctggaa cctgactccg
1021 ttaggacgaa catctgcccc ttcagggagg accccgcgc acaccagaac ctctggcaag
1081 ccgcccgact gcgactgctg accctgcaga gctggctgct ggacgcaccg tgctcgctgc
1141 ccgcagaagc ggcactgtgc tggcgggctc cgggtgggga cccctgccag ccactggtcc
1201 caccgctttc ctgggagaac gtcactgtgg acaaggttct cgagttccca ttgctgaaag
1261 gccaccctaa cctctgtgtt caggtgaaca gctcggagaa gctgcagctg caggagtgct
1321 tgtgggctga ctccctgggg cctctcaaag acgatgtgct actgttggag acacgaggcc
1381 cccaggacaa cagatccctc tgtgccttgg aacccagtgg ctgtacttca ctacccagca
1441 aagcctccac gagggcagct cgccttggag agtacttact acaagacctg cagtcaggcc
1501 agtgtctgca gctatgggac gatgacttgg gagcgctatg ggcctgcccc atggacaaat
1561 acatccacaa gcgctgggcc ctcgtgtggc tggcctgcct actctttgcc gctgcgcttt
1621 ccctcatcct ccttctcaaa aaggatcacg cgaaagggtg gctgaggctc ttgaaacagg
1681 acgtccgctc gggggcggcc gccagggcc gcgcggctct gctcctctac tcagccgatg
1741 actcgggttt cgagcgcctg gtgggcgccc tggcgtcggc cctgtgccag ctgccgctgc
1801 gcgtggccgt agacctgtgg agccgtcgtg aactgagcgc gcagggcccc gtggcttggt
1861 ttcacgcgca gcggcgccag accctgcagg agggcggcgt ggtggtcttg ctcttctctc
1921 ccggtgcggt ggcgctgtgc agcgagtggc tacaggatgg ggtgtccggg cccggggcgc
1981 acggcccgca cgacgcctcc cgcgcctcgc tcagctgcgt gctgcccgac ttcttgcagg
2041 gccgggcgcc cggcagctac gtgggggcct gcttcgacag gctgctccac ccggacgccg
2101 tacccgccct tttccgcacc gtgccgtct tcacactgcc ctcccaactg ccagacttcc
2161 tgggggccct gcagcagcct cgcgcccgc gttccgggcg gctccaagag agagcggagc
2221 aagtgtcccg ggcccttcag ccagccctgg atagctactt ccatccccg gggactcccg
2281 cgccgggacg cggggtggga ccaggggcgg gacctggggc gggggacggg acttaaataa
2341 aggcagacgc tgttttttcta cccatgtggc ccaaaaaaaa aaaaaaaaaa aaaaaaaaaa
2401 aaaaaaaaaa aaaaaaaaaa aaaaaaaaaa aaa
```

IL-17RC, transcript variant 3, is encoded by the following amino acid sequence (NCBI Accession No. NM_032732 and SEQ ID NO: 22):

MPVPWFLLSLALGRSPVVLSLERLVGPQDATHCSPGLSCRLWDSDILCLP
GDIVPAPGPVLAPTHLQTELVLRCQKETDCDLCLRVAVHLAVHGHWEEPE
DEEKFGGAADSGVEEPRNASLQAQVVLSFQAYPTARCVLLEVQVPAALVQ
FGQSVGSVVYDCFEAALGSEVRIWSYTQPRYEKELNHTQQLPALPWLNVS
ADGDNVHLVLNVSEEQHFGLSLYWNQVQGPPKPRWHKNLTGPQIITLNHT
DLVPCLCIQVWPLEPDSVRTNICPFREDPRAHQNLWQAARLRLLTLQSWL
LDAPCSLPAEAALCWRAPGGDPCQPLVPPLSWENVTVDKVLEFPLLKGHP

-continued

NLCVQVNSSEKLQLQECLWADSLGPLKDDVLLLETRGPQDNRSLCALEPS
GCTSLPSKASTRAARLGEYLLQDLQSGQCLQLWDDDLGALWACPMDKYIH
KRWALVWLACLLLFAAALSLILLLKKDHAKGWLRLLKQDVRSGAAARGRAA
LLLYSADDSGFERLVGALASALCQLPLRVAVDLWSRRELSAQGPVAWFHA
QRRQTLQEGGVVVLLFSPGAVALCSEWLQDGVSGPGAHGPHDAFRASLSC
VLPDFLQGRAPGSYVGACFDRLLHPDAVPALFRTVPVFTLPSQLPDFLGA
LQQPRAPRSGRLQERAEQVSRALQPALDSYFHPPGTPAPGRGVGPGAGPG
AGDGT

IL-17RD, transcript 1, is encoded by the following mRNA sequence (NCBI Accession No. NM_001080973 and SEQ ID NO: 23):

```
   1 gcggccgccg cggccaccgc ccactcgggg ctggccagcg gcgggcggcc ggggcgcaga
  61 gaacggcctg gctgggcgag cgcacggccA TGgccccgtg gctgcagctc tgctccgtct
 121 tctttacggt caacgcctgc ctcaacggct cgcagctggc tgtggccgct ggcgggtccg
 181 gccgcgcgcg gggcgccgac acctgtggct ggaggggagt ggggccagcc agcagaaaca
 241 gtgggctgta caacatcacc ttcaaatatg acaattgtac cacctacttg aatccagtgg
 301 ggaagcatgt gattgctgac gcccagaata tcaccatcag ccagtatgct tgccatgacc
 361 aagtggcagt caccattctt tggtccccag ggccctcgg catcgaattc ctgaaaggat
 421 ttcgggtaat actggaggag ctgaagtcgg agggaagaca gtgccaacaa ctgattctaa
 481 aggatccgaa gcagctcaac agtagcttca aaagaactgg aatggaatct caacctttcc
 541 tgaatatgaa atttgaaacg gattatttcg taaaggttgt ccctttctcct tccattaaaa
 601 acgaaagcaa ttaccaccct ttcttcttta gaacccgagc ctgtgacctg ttgttacagc
 661 cggacaatct agcttgtaaa cccttctgga agcctcggaa cctgaacatc agccagcatg
 721 gctcggacat gcaggtgtcc ttcgaccatg caccgcacaa cttcggcttc cgtttcttct
 781 atcttcacta caagctcaag cacgaaggac ctttcaagcg aaagacctgt aagcaggagc
 841 aaactacaga gacgaccagc tgcctccttc aaaatgtttc tccaggggat tatataattg
 901 agctggtgga tgacactaac acaacaagaa aagtgatgca ttatgcctta aagccagtgc
 961 actccccgtg ggccgggccc atcagagccg tggccatcac agtgccactg gtagtcatat
1021 cggcattcgc gacgctcttc actgtgatgt gccgcaagaa gcaacaagaa aatatatatt
1081 cacatttaga tgaagagagc tctgagtctt ccacatacac tgcagcactc ccaagagaga
1141 ggctccggcc gcggccgaag gtctttctct gctattccag taaagatggc cagaatcaca
1201 tgaatgtcgt ccagtgtttc gcctacttcc tccaggactt ctgtggctgt gaggtggctc
1261 tggacctgtg ggaagacttc agcctctgta gagaagggca gagagaatgg gtcatccaga
1321 agatccacga gtcccagttc atcattgtgg tttgttccaa aggtatgaag tactttgtgg
1381 acaagaagaa ctacaaacac aaaggaggtg gccgaggctc ggggaaagga gagctcttcc
1441 tggtggcggt gtcagccatt gccgaaaagc tccgccaggc caagcagagt tcgtccgcgg
1501 cgctcagcaa gtttatcgcc gtctactttg attattcctg cgagggagac gtccccggta
1561 tcctagacct gagtaccaag tacagactca tggacaatct tcctcagctc tgttcccact
1621 tgcactcccg agaccacggc ctccaggagc cggggcagca cacgcgacag ggcagcagaa
1681 ggaactactt ccggagcaag tcaggccggt ccctatacgt cgccatttgc aacatgcacc
1741 agtttattga cgaggagccc gactggttcg aaaagcagtt cgttcccttc catcctcctc
```

-continued

```
1801 cactgcgcta ccgggagcca gtcttggaga aatttgattc gggcttggtt ttaaatgatg
1861 tcatgtgcaa accagggcct gagagtgact tctgcctaaa ggtagaggcg gctgttcttg
1921 gggcaaccgg accagccgac tcccagcacg agagtcagca tgggggcctg gaccaagacg
1981 gggaggcccg gcctgccctt gacggtagcg ccgccctgca cccctgctg cacacggtga
2041 aagccggcag ccctcggac atgccgcggg actcaggcat ctatgactcg tctgtgccct
2101 catccgagct gtctctgcca ctgatggaag gactctcgac ggaccagaca gaaacgtctt
2161 ccctgacgga gagcgtgtcc tcctcttcag gcctgggtga ggaggaacct cctgcccttc
2221 cttccaagct cctctcttct gggtcatgca aagcagatct tggttgccgc agctacactg
2281 atgaactcca cgcggtcgcc cctttgtaac aaaacgaaag agtctaagca ttgccacttt
2341 agctgctgcc tccctctgat tccccagctc atctccctgg ttgcatggcc cacttggagc
2401 tgaggtctca tacaaggata tttggagtga aatgctggcc agtacttgtt ctcccttgcc
2461 ccaaccctt accggatatc ttgacaaact ctccaatttt ctaaaatgat atggagctct
2521 gaaaggcatg tccataaggt ctgacaacag cttgccaaat ttggttagtc cttggatcag
2581 agcctgttgt gggaggtagg gaggaaatat gtaaagaaaa acaggaagat acctgcacta
2641 atcattcaga cttcattgag ctctgcaaac tttgcctgtt tgctattggc taccttgatt
2701 tgaaatgctt tgtgaaaaaa ggcacttta acatcatagc cacagaaatc aagtgccagt
2761 ctatctggaa tccatgttgt attgcagata atgttctcat ttatttttga tgtagaattt
2821 acattgccat gggtgttaaa taagctttga gtcaaaagtc aagaaagtga ctgaatatac
2881 agtcaccttt tatgaaatga gtctctgtgt tactgggtgg catgactgat tgaggtgaag
2941 ctcacgggc caggctgacc gtcttgaccg ttccacttga gataggttgg tcatcgtgca
3001 gaaggcccca ggacctcagc acacacagcc tcctcttggt ctgagtaggc atcatgtggg
3061 ggccagatct gcctgctgtt tccatgggtt acatttactg tgctgtatct cagatgttgg
3121 tgtctggaag tttattctta agagactgct acccagctgg tctgtattat tggaagttgc
3181 agttcgtgct ttggttggcc ttctggtcta aagctgtgtc ctgaatatta gggatcacaa
3241 ttcactgaaa tacagcagtg tgtggaggtg atggccagtt aatctgctga actggttttg
3301 actaatgaca aacctctttt taagatggta gaatggaggt gatagtcaca aaagtaaatg
3361 ttccattttt atgaatgact ttctacagag tttctatttc taaagaaaaa acaattgttc
3421 acatcccatc tgatgattag catgtgtgta atgaatgctg tcttggtctc ccctgtggaa
3481 acccttctcc ctgtgcctta gagcaggtgt gtacatctct cactaccttt ctcatgggtg
3541 ctgttagatt ttggcacccg ttttctcagc attcagccca gggaatgtgg ttttcacttc
3601 ttcgtcagat aagaccaaca tgaagggta tgttgagaaa catcctgagg caaggtggga
3661 ggtgggatgg gacaggactt tcccttccaa gcacatgcat ggcaggtggg gaaagggggg
3721 cttgcacccc tgctggaaag aaaaggtttg tgtatatttc tgatgcaaat gtcatactca
3781 ctgctctgta aaggcagctg gcagcttttt gggaaaagaa cgtgctcgtc tgttctctgg
3841 catcaagttt cttgcagctg ctctgaggga gagacagtga gctgcaagac tgcctcccca
3901 taacaacagg caactcagag aagagtcatt ttatgttgtt cctatggaat ctggaatgag
3961 tgcagagctc ctacccacac atgactgccc cgccattca tcctaggcat tctgtgaagg
4021 agattggtta gtccaaactt gctaacatac gaaaattcac ttgaacatg atgagagatt
4081 tcttattgag gccaagagat gtttcctgtc ccagaggaac cattaggagt cgcttttagg
4141 gtattcagct ttgttcatga aataaggcat ctctgagaaa gtggccccag ggagagaatg
```

-continued

```
4201 gaggactggg aggagaagca ttaactgagc tccaagggtg tgtgggcaga gagcttgcta
4261 tgtgaactca ctccttaaga aaatggaaga gaaaagaga gtgctagtta aaaaatcggg
4321 atgttttagt ttggatttag ggttttgata cttatgttga aatactaatg tttctgatca
4381 ataaaatcaa actcttaata taccgagtaa tgaaaccata gtgtgattgc ctcagaataa
4441 attgagaagt ccaacttcct agttttgttt aattagtttc acttttcta ctctccccag
4501 tatgctagaa atgggaatcg ttgccctgca gattacggca aaacatctgt tttaagcaaa
4561 gctgcatttt ttgactcaga aattgtccca gacggtggat ataagatgaa attcagaaaa
4621 acgttctgcc aagtcacagg cttttagata ttatggaaac aagaaatgga aaacaggatg
4681 atctccatga gaggccttga tcctgagagt aaaaggcttg tgtagatagg ttagacaacg
4741 tcctctagaa aagagaccag ggataagtcc aggtttccag gaaaaccaag aagcctgcgg
4801 gtagctgaag gtagagtgct agttgttcat cttaacttac caatgagcta cagaaaggac
4861 ttagcatctg atgtcatcag ctttgccagg agagtgatca aggaggttaa agctcaggta
4921 aaggtgtgcc ttctcagaga ttggctacaa gcaacagaga ccacctcaac agagaccacc
4981 tcaacagact cagcccagcc atacaaggtg ccaaagctcc tccagagggc tgtcttgggc
5041 ctttgaggca attgatctcc agaaagagtc agaagtcatt ccagtccagg cccaggtatt
5101 cagatggtga cccagccaga taatagtatc ttgagcaaat aatagtatct tgagtgcaaa
5161 taagcaggaa gactgtcctt caaaaaatgt ggggttacat gattttcaga gccttttttt
5221 cagagttgag catcttttct tttaaaagaa ataaggggca agaggaccaa ttttattcct
5281 tgaggaaaaa tgacacaccc ttctcccaaa agaaagaaaa ctctctggcc ccccaacttc
5341 aacactaatt tggctccctg aagaagagag aaaatattat ttctgtcttt attgaagaga
5401 aatgggcaat gccaatgtga aggttactag tctttttttat tttctattgg tgaagactac
5461 tactgctctt atttagcaga tcttatacct tcagtggtca ccagtatagc aggtgaggta
5521 taaggaaaac agcagtgtga tgataaatgg taattaatat actttgtctg tgtcagcaat
5581 agggaatggt ggggactgtg gcaaactgaa gcgcccctgt tccacccaca gtgggtaatt
5641 ttccagtcga ctgtggccat gaagtacttc ctgatcttcc cattttttcaa gaaaagctga
5701 caatctggat ttttatatga aaaattctga ttttaaaaaa tattggcaac taagttaaaa
5761 ttcaagtgaa tttagaccca gcagaagaca tggatggacc tgatttggtc cactgactac
5821 cagtttgtta acctgtgctt tataagattt gaaggaaagg cattcatggt aattacagac
5881 ggtgccacca gaaaatgctc ttgctaaatg cagccagtag ttagattgct tctttctcca
5941 gtctcccccg caaagaaatt tgacgtgatt ctgaatgcac tggacatgtc ttgattgcgt
6001 ctttacattt cacagtgtct taaaagaaag gcaagccagt tgttaatttc agaatcagat
6061 ttatgctctc tcaatttaaa aaatgctggg aacaatttca tttttttttt tttgagatgg
6121 agtcttgctc tgttgcccag gctggagtgc agtggcgtga tctcggctca ctgcaagctc
6181 cacctcccgg gttcacgcca ttctcctgcc tcagcctcct gagtagctgg gactacaggc
6241 gcccaccacc acgcctggct aattttttg tatttttagt agagacgggg tttcactgtg
6301 ttagccagga tgatctcgat ctcctgacct ggtgatccgc ttgcctcggc ctcccaaagt
6361 gctgggatta caggcgtgag ccactgcgcc cggcctaaca atttcattta aactccacaa
6421 cctaaagggc tttgtttata gttttagctc ttggcataat ttttttcagg tggtgtgcaa
6481 ttctgagcat aggccaagac atgattagga aagcaggcag ttgtagagag taaggcaagg
6541 aacctcctag cgtccattag agccaggtat ttgcattatc ttccgtttta agtggtctgt
6601 gaattgactg tgttttggag gtgtgaaaca gtatacagag aaaagctttt cctgatactg
```

```
6661 agatatcagt taggagtcca aatggggtgt tgggtcatcc ttgccatatc acctcctttc
6721 caggctcaga gtgaaaatag acaaaaggaa atctgactgc aagccagtgg ctttgattcc
6781 agtttcagag tttagggact aggagagagt ttagattatc tagcatattc tccccctggt
6841 gtcagacagg gctgtgcctg aattattcca gacatatggc tgtagatggt attctttatt
6901 ttataagaag gagattctgt aacctaccct gctgatcaga tagttctttg tatgtcttag
6961 agaaattcaa gccagcttcc ttttgttcgg cttgtagtgg agaaagaaca gctggtcacc
7021 ttccatgtat tcaaaaacca cagtgaagtc atcccctgg tgttttatt tcagtgataa
7081 ataattccac ccacttaaac cattcttcat ggctcttgtt ttccaggggc taataattt
7141 tcactgctgt aatgtttctc agcttcacac ttagtttagt tgcccaaaca atgttggtgc
7201 cttactcaca ttggtgcctt gtgaagacga ggctcaggat gggattatg gggaaattct
7261 tgcacaccca gctcctctta ccacttaaaa atataatggc actttcacaa aatgatatgt
7321 cacctatatt cattgagaat tatttgactg ccacattttt cccctgatga tagtcatcta
7381 tcataacttg tgtttgtttt cctcctgaga tcaaacactt ggtgcttatt cctgatgtat
7441 actctgagac cagctcttac cttctgagtg gcagctaccc ctccctccca attttagatc
7501 ctattttttac acatctctat agatatcacc tttatttcat gactcacaat attaaatggt
7561 acagacttca gtttaaccac tggtgtggta acagcagtag ttgctaagta ccaccttccc
7621 attgctgttt gagggctaat ttgcaaagac atttgaatct cccagtgaag atgtctgggg
7681 aattttggcc agttgtcttc cctcttgccc ttttgttctt taaaattcag cttggaccat
7741 agacacctcc aggatcttgt ttatgttctg ctctcaattg accaagcact gcgttttgca
7801 caatcagaag tctcacaaaa gcaaacagtt atgactgcat atctgatgtt tatatcctat
7861 aaaatttcag gaagattcag agtcaatctt ctatttgtac atgatgtaga caaaattagc
7921 tgctccaatt gttagacaaa aaattgccat tggattacac taatgtgctc atctgttgtt
7981 ttaaaagttt ggtatcaggc ggggcacggt ggctcacgcc tgtaatccca gcatttgggg
8041 aggccaaggt gggcggatca cctgaggtcc agagttcaag accagcctga ccaacatggt
8101 gaaaccctgt ctctactaaa aatacaaaat taatcaggcg tggttgtgtg tgcctgtaat
8161 cccagctact cgagaggctg aggcaggaga atcgcttgaa tccgggaggc agaggttgca
8221 gtgagctgag atcacgccat tgcactctag cctgggcaac aagagcgaaa ctccgtctca
8281 acaacaacaa caaaaagttt ggtatgtttc tctcaagaaa aaagcatggt gagtccagac
8341 agcagcaaaa gcttttgtga aaaccaattg tgttcatcta gatagtaagt aactcctatt
8401 tttactgtta attttttaaa agagaatttt tccctgtgga aactccctgt tagtacgtcc
8461 taggggagaa agcctgtgga atatggtggt tattgatggc gttgcctttg tttcatcttt
8521 gagtttgccc tttgtgggat ctagtgggat aatgagcact gacagaactc ttaacagcgt
8581 gctgtatttt tgacattgaa aatgttaatg acttgatttg tacataactc tgtaactagg
8641 tgaaagtaga tcacagctga catttacaaa atgttttgt accttagaat ttctgcatta
8701 aataaaatgt tttgttttaa
```

IL-17RD, transcript 1, is encoded by the following amino acid sequence (NCBI Accession No. NM_001080973 and SEQ ID NO: 24):

MAPWLQLCSVFFTVNACLNGSQLAVAAGGSGRARGADTCGWRGVGPASRN
SGLYNITFKYDNCTTYLNPVGKHVIADAQNITISQYACHDQVAVTILWSP
GALGIEFLKGFRVILEELKSEGRQCQQLILKDPKQLNSSFKRTGMESQPF
LNMKFETDYFVKVVPFPSIKNESNYHPFFFRTRACDLLLQPDNLACKPFW
KPRNLNISQHGSDMQVSFDHAPHNFGFRFFYLHYKLKHEGPFKRKTCKQE

-continued

QTTETTSCLLQNVSPGDYIIELVDDTNTTRKVMHYALKPVHSPWAGPIRA
VAITVPLVVISAFATLFTVMCRKKQQENIYSHLDEESSESSTYTAALPRE
RLRPRPKVFLCYSSKDGQNHMNVVQCFAYFLQDFCGCEVALDLWEDFSLC
REGQREWVIQKIHESQFIIVVCSKGMKYFVDKKNYKHKGGGRGSGKGELF
LVAVSAIAEKLRQAKQSSSAALSKFIAVYFDYSCEGDVPGILDLSTKYRL
MDNLPQLCSHLHSRDHGLQEPGQHTRQGSRRNYFRSKSGRSLYVAICNMH

-continued

QFIDEEPDWFEKQFVPFHPPPLRYREPVLEKFDSGLVLNDVMCKPGPESD
FCLKVEAAVLGATGPADSQHESQHGGLDQDGEARPALDGSAALQPLLHTV
KAGSPSDMPRDSGIYDSSVPSSELSLPLMEGLSTDQTETSSLTESVSSSS
GLGEEEPPALPSKLLSSGSCKADLGCRSYTDELHAVAPL

IL-17RD, transcript 2, is encoded by the following mRNA sequence (NCBI Accession No. NM_017563 and SEQ ID NO: 25, note that this sequence contains an alternative start codon from nucleotide position 208-210):

```
   1 atccgctctt cttttcctcc gggaaaagaa acgggaagtg gccgtgggcc ggtgaattcc
  61 gtgtagtggc caagctttgt tccaaagagg gggaggtggt gacagtctct tgcccactga
 121 agcgtgccag acagagtgct aggcatgggg gcagaggtga atcagatgac agccacctct
 181 caccacgagg agtggctgaa agtgtgaCTG gactacaggc aatcctggcc ttggcaggga
 241 gtggggccag ccagcagaaa cagtgggctg tacaacatca ccttcaaata tgacaattgt
 301 accacctact tgaatccagt ggggaagcat gtgattgctg acgccagaa tatcaccatc
 361 agccagtatg cttgccatga ccaagtggca gtcaccattc tttggtcccc aggggccctc
 421 ggcatcgaat tcctgaaagg atttcgggta atactggagg agctgaagtc ggagggaaga
 481 cagtgccaac aactgattct aaaggatccg aagcagctca acagtagctt caaaagaact
 541 ggaatggaat ctcaaccttt cctgaatatg aaatttgaaa cggattattt cgtaaaggtt
 601 gtccctttc cttccattaa aaacgaaagc aattaccacc ctttcttctt tagaacccga
 661 gcctgtgacc tgttgttaca gccggacaat ctagcttgta aaccttctg gaagcctcgg
 721 aacctgaaca tcagccagca tggctcggac atgcaggtgt ccttcgacca tgcaccgcac
 781 aacttcggct tccgtttctt ctatcttcac tacaagctca agcacgaagg acctttcaag
 841 cgaaagacct gtaagcagga gcaaactaca gagacgacca gctgcctcct tcaaaatgtt
 901 tctccagggg attatataat tgagctggtg gatgacacta acacaacaag aaaagtgatg
 961 cattatgcct taaagccagt gcactcccg tgggccgggc ccatcagagc cgtggccatc
1021 acagtgccac tggtagtcat atcggcattc gcgacgctct tcactgtgat gtgccgcaag
1081 aagcaacaag aaaatatata ttcacattta gatgaagaga gctctgagtc ttccacatac
1141 actgcagcac tcccaagaga gaggctccgg ccgcggccga aggtctttct ctgctattcc
1201 agtaaagatg gccagaatca catgaatgtc gtccagtgtt tcgcctactt cctccaggac
1261 ttctgtggct gtgaggtggc tctggacctg tgggaagact cagcctctg tagagaaggg
1321 cagagagaat gggtcatcca aagatccac gagtcccagt tcatcattgt ggtttgttcc
1381 aaaggtatga agtactttgt ggacaagaag aactacaaac acaaggagg tggccgaggc
1441 tcggggaaag gagagctctt cctggtggcg gtgtcagcca ttgccgaaaa gctccgccag
1501 gccaagcaga gttcgtccgc ggcgctcagc aagtttatcg ccgtctactt tgattattcc
1561 tgcgagggag acgtccccgg tatcctagac ctgagtacca agtacagact catggacaat
1621 cttcctcagc tctgttccca cttgcactcc cgagaccacg gcctccagga gccggggcag
1681 cacacgcgac agggcagcag aaggaactac ttccggagca agtcaggccg gtccctatac
1741 gtcgccattt gcaacatgca ccagtttatt gacgaggagc ccgactggtt cgaaaagcag
1801 ttcgttccct ccatcctcc tccactgcgc taccgggagc cagtcttgga gaaatttgat
1861 tcgggcttgg ttttaaatga tgtcatgtgc aaaccagggc ctgagagtga cttctgccta
1921 aaggtagagg cggctgttct tggggcaacc ggaccagccg actcccagca cgagagtcag
```

-continued

```
1981  catgggggcc tggaccaaga cggggaggcc cggcctgccc ttgacggtag cgccgccctg
2041  caacccctgc tgcacacggt gaaagccggc agccctcgg acatgccgcg ggactcaggc
2101  atctatgact cgtctgtgcc ctcatccgag ctgtctctgc cactgatgga aggactctcg
2161  acggaccaga cagaaacgtc ttccctgacg gagagcgtgt cctcctcttc aggcctgggt
2221  gaggaggaac ctcctgccct tccttccaag ctcctctctt ctgggtcatg caaagcagat
2281  cttggttgcc gcagctacac tgatgaactc cacgcggtcg ccccttgta acaaaacgaa
2341  agagtctaag cattgccact ttagctgctg cctccctctg attccccagc tcatctccct
2401  ggttgcatgg cccacttgga gctgaggtct catacaagga tatttggagt gaaatgctgg
2461  ccagtacttg ttctcccttg ccccaaccct ttaccggata tcttgacaaa ctctccaatt
2521  ttctaaaatg atatggagct ctgaaaggca tgtccataag gtctgacaac agcttgccaa
2581  atttggttag tccttggatc agagcctgtt gtgggaggta gggaggaaat atgtaaagaa
2641  aaacaggaag atacctgcac taatcattca gacttcattg agctctgcaa actttgcctg
2701  tttgctattg gctaccttga tttgaaatgc tttgtgaaaa aaggcacttt taacatcata
2761  gccacagaaa tcaagtgcca gtctatctgg aatccatgtt gtattgcaga taatgttctc
2821  atttattttt gatgtagaat ttacattgcc atgggtgtta aataagcttt gagtcaaaag
2881  tcaagaaagt gactgaatat acagtcacct tttatgaaat gagtctctgt gttactgggt
2941  ggcatgactg attgaggtga agctcacggg gccaggctga ccgtcttgac cgttccactt
3001  gagataggtt ggtcatcgtg cagaaggccc caggacctca gcacacacag cctcctcttg
3061  gtctgagtag gcatcatgtg ggggccagat ctgcctgctg tttccatggg ttacatttac
3121  tgtgctgtat ctcagatgtt ggtgtctgga agtttattct taagagactg ctacccagct
3181  ggtctgtatt attggaagtt gcagttcgtg ctttggttgg ccttctggtc taaagctgtg
3241  tcctgaatat tagggatcac aattcactga aatacagcag tgtgtggagg tgatggccag
3301  ttaatctgct gaactggttt tgactaatga caaacctctt tttaagatgg tagaatggag
3361  gtgatagtca caaagtaaa tgttccattt ttatgaatga cttttctacag agtttctatt
3421  tctaaagaaa aaacaattgt tcacatccca tctgatgatt agcatgtgtg taatgaatgc
3481  tgtcttggtc tcccctgtgg aaaccttct ccctgtgcct tagagcaggt gtgtacatct
3541  ctcactacct ttctcatggg tgctgttaga ttttggcacc cgttttctca gcattcagcc
3601  cagggaatgt ggttttcact tcttcgtcag ataagaccaa catgaagggg tatgttgaga
3661  aacatcctga ggcaaggtgg gaggtgggat ggggcaggac tttcccttcc aagcacatgc
3721  atggcaggtg gggaaagggg ggcttgcacc cctgctggaa agaaaaggtt tgtgtatatt
3781  tctgatgcaa atgtcatact cactgctctg taaaggcagc tggcagcttt tgggaaaag
3841  aacgtgctcg tctgttctct ggcatcaagt ttcttgcagc tgctctgagg gagagacagt
3901  gagctgcaag actgcctccc cataacaaca ggcaactcag agaagagtca ttttatgttg
3961  ttcctatgga atctggaatg agtgcagagc tcctacccac acatgactgc cccgccattt
4021  catcctaggc attctgtgaa ggagattggt tagtccaaac ttgctaacat acgaaaattc
4081  acttggaaca tgatgagaga tttcttattg aggccaagag atgtttcctg tcccagagga
4141  accattagga gtcgctttta gggtattcag ctttgttcat gaaataaggc atctctgaga
4201  aagtggcccc agggagagaa tggaggactg ggaggagaag cattaactga gctccaaggg
4261  tgtgtgggca gagagcttgc tatgtgaact cactccttaa gaaaatggaa gagaaaaaga
4321  gagtgctagt taaaaaatcg ggatgtttta gtttggattt agggttttga tacttatgtt
```

-continued

```
4381 gaaatactaa tgtttctgat caataaaatc aaactcttaa tataccgagt aatgaaacca
4441 tagtgtgatt gcctcagaat aaattgagaa gtccaacttc ctagttttgt ttaattagtt
4501 tcactttttc tactctcccc agtatgctag aaatgggaat cgttgccctg cagattacgg
4561 caaaacatct gttttaagca aagctgcatt ttttgactca gaaattgtcc cagacggtgg
4621 atataagatg aaattcagaa aaacgttctg ccaagtcaca ggcttttaga tattatggaa
4681 acaagaaatg gaaaacagga tgatctccat gagaggcctt gatcctgaga gtaaaaggct
4741 tgtgtagata ggttagacaa cgtcctctag aaaagagacc agggataagt ccaggtttcc
4801 aggaaaacca agaagcctgc gggtagctga aggtagagtg ctagttgttc atcttaactt
4861 accaatgagc tacagaaagg acttagcatc tgatgtcatc agctttgcca ggagagtgat
4921 caaggaggtt aaagctcagg taaaggtgtg ccttctcaga gattggctac aagcaacaga
4981 gaccacctca acagagacca cctcaacaga ctcagcccag ccatacaagg tgccaaagct
5041 cctccagagg gctgtcttgg gcctttgagg caattgatct ccagaaagag tcagaagtca
5101 ttccagtcca ggcccaggta ttcagatggt gacccagcca gataatagta tcttgagcaa
5161 ataatagtat cttgagtgca aataagcagg aagactgtcc ttcaaaaaat gtggggttac
5221 atgattttca gagccttttt ttcagagttg agcatctttt cttttaaaag aaataagggg
5281 caagaggacc aattttattc cttgaggaaa aatgacacac ccttctccca aagaaagaa
5341 aactctctgg cccccccaact tcaacactaa tttggctccc tgaagaagag agaaaatatt
5401 atttctgtct ttattgaaga gaaatgggca atgccaatgt gaaggttact agtcttttt
5461 attttctatt ggtgaagact actactgctc ttatttagca gatcttatac cttcagtggt
5521 caccagtata gcaggtgagg tataaggaaa acagcagtgt gatgataaat ggtaattaat
5581 atactttgtc tgtgtcagca ataggaatg gtggggactg tggcaaactg aagcgcccct
5641 gttccaccca cagtgggtaa ttttccagtc gactgtggcc atgaagtact tcctgatctt
5701 cccattttc aagaaaagct gacaatctgg attttatat gaaaattct gattttaaaa
5761 aatattggca actaagttaa aattcaagtg aatttagacc cagcagaaga catggatgga
5821 cctgatttgg tccactgact accagtttgt taacctgtgc tttataagat ttgaaggaaa
5881 ggcattcatg gtaattacag acggtgccac cagaaaatgc tcttgctaaa tgcagccagt
5941 agttagatt cttctttctc cagtctcccc cgcaaagaaa tttgacgtga ttctgaatgc
6001 actggacatg tcttgattgc gtcttttacat ttcacagtgt cttaaaagaa aggcaagcca
6061 gttgttaatt tcagaatcag atttatgctc tctcaattta aaaaatgctg gaacaatt
6121 cattttttt tttttgagat ggagtcttgc tctgttgccc aggctggagt gcagtggcgt
6181 gatctcggct cactgcaagc tccacctccc gggttcacgc cattctcctg cctcagcctc
6241 ctgagtagct gggactacag gcgcccacca ccacgcctgg ctaattttt tgtattttta
6301 gtagagacgg ggtttcactg tgttagccag gatgatctcg atctcctgac ctggtgatcc
6361 gcttgcctcg gcctcccaaa gtgctgggat tacaggcgtg agccactgcg cccggcctaa
6421 caatttcatt taaactccac aacctaaagg gctttgttta tagttttagc tcttggcata
6481 atttttttca ggtggtgtgc aattctgagc ataggccaag acatgattag gaaagcaggc
6541 agttgtagag agtaaggcaa ggaacctcct agcgtccatt agagccaggt atttgcatta
6601 tcttccgttt taagtggtct gtgaattgac tgtgttttgg aggtgtgaaa cagtatacag
6661 agaaaagctt ttcctgatac tgagatatcg gttaggagtc caaatggggt gttgggtcat
6721 ccttgccata tcacctcctt tccaggctca gagtgaaaat agacaaaagg aaatctgact
6781 gcaagccagt ggctttgatt ccagtttcag agtttaggga ctaggagaga gtttagatta
```

```
6841 tctagcatat tctcccctg gtgtcagaca gggctgtgcc tgaattattc cagacatatg 6901 gctgtagatg gtattcttta ttttataaga aggagattct gtaacctacc ctgctgatca 6961 gatagttctt tgtatgtctt agagaaattc aagccagctt cctttgttc ggcttgtagt 7021 ggagaaagaa cagctggtca ccttccatgt attcaaaaac cacagtgaag tcatccccct 7081 ggtgttttta tttcagtgat aaataattcc acccacttaa accattcttc atggctcttg 7141 ttttccaggg gcctaataat tttcactgct gtaatgtttc tcagcttcac acttagttta 7201 gttgcccaaa caatgttggt gccttactca cattggtgcc ttgtgaagac gaggctcagg 7261 atggggatta tggggaaatt cttgcacacc cagctcctct taccacttaa aaatataatg 7321 gcactttcac aaaatgatat gtcacctata ttcattgaga attatttgac tgccacattt 7381 ttccctgat gatagtcatc tatcataact tgtgtttgtt ttcctcctga gatcaaacac 7441 ttggtgctta ttcctgatgt atactctgag accagctctt accttctgag tggcagctac 7501 ccctccctcc caattttaga tcctattttt acacatctct atagatatca cctttatttc 7561 atgactcaca atattaaatg gtacagactt cagtttaacc actggtgtgg taacagcagt 7621 agttgctaag taccaccttc ccattgctgt ttgagggcta atttgcaaag acatttgaat 7681 ctcccagtga agatgtctgg ggaattttgg ccagttgtct tccctcttgc ccttttgttc 7741 tttaaaattc agcttggacc atagacacct ccaggatctt gtttatgttc tgctctcaat 7801 tgaccaagca ctgcgttttg cacaatcaga agtctcacaa aagcaaacag ttatgactgc 7861 atatctgatg tttatatcct ataaaatttc aggaagattc agagtcaatc ttctatttgt 7921 acatgatgta gacaaaatta gctgctccaa ttgttagaca aaaaattgcc attggattac 7981 actaatgtgc tcatctgttg ttttaaaagt ttggtatcag gcggggcacg gtggctcacg 8041 cctgtaatcc cagcattttg ggaggccaag gtgggcggat cacctgaggt ccagagttca 8101 agaccagcct gaccaacatg gtgaaaccct gtctctacta aaaatacaaa attaatcagg 8161 cgtggttgtg tgtgcctgta atcccagcta ctcgagaggc tgaggcagga gaatcgcttg 8221 aatccgggag gcagaggttg cagtgagctg agatcacgcc attgcactct agcctgggca 8281 acaagagcga aactccgtct caacaacaac aacaaaaagt ttggtatgtt tctctcaaga 8341 aaaaagcatg gtgagtccag acagcagcaa aagcttttgt gaaaaccaat tgtgttcatc 8401 tagatagtaa gtaactccta tttttactgt taatttttta aaagagaatt tttccctgtg 8461 gaaactccct gttagtacgt cctaggggag aaagcctgtg gaatatggtg gttattgatg 8521 gcgttgcctt tgtttcatct ttgagtttgc cctttgtggg atctagtggg ataatgagca 8581 ctgacagaac tcttaacagc gtgctgtatt tttgacattg aaaatgttaa tgacttgatt 8641 tgtacataac tctgtaacta ggtgaaagta gatcacagct gacatttaca aaatgttttt 8701 gtaccttaga atttctgcat taaataaaat gttttgtttt aa
```

IL-17RD, transcript 2, is encoded by the following amino acid sequence (NCBI Accession No. NM_017563 and SEQ ID NO: 26):

MDYRQSWPWQGVGPASRNSGLYNITFKYDNCTTYLNPVGKHVIADAQNIT

ISQYACHDQVAVTILWSPGALGIEFLKGFRVILEELKSEGRQCQQLILKD

PKQLNSSFKRTGMESQPFLNMKFETDYFVKVVPFPSIKNESNYHPFFFRT

RACDLLLQPDNLACKPFWKPRNLNISQHGSDMQVSFDHAPHNFGFRFFYL

HYKLKHEGPFKRKTCKQEQTTETTSCLLQNVSPGDYIIELVDDTNTTRKV

MHYALKPVHSPWAGPIRAVAITVPLVVISAFATLFTVMCRKKQQENIYSH

LDEESSESSTYTAALPRERLRPRPKVFLCYSSKDGQNHMNVVQCFAYFLQ

DFCGCEVALDLWEDFSLCREGQREWVIQKIHESQFIIVVCSKGMKYFVDK

KNYKHKGGGRGSGKGELFLVAVSAIAEKLRQAKQSSSAALSKFIAVYFDY

SCEGDVPGILDLSTKYRLMDNLPQLCSHLHSRDHGLQEPGQHTRQGSRRN

YFRSKSGRSLYVAICNMHQFIDEEPDWFEKQFVPFHPPPLRYREPVLEKF

DSGLVLNDVMCKPGPESDFCLKVEAAVLGATGPADSQHESQHGGLDQDGE

ARPALDGSAALQPLLHTVKAGSPSDMPRDSGIYDSSVPSSELSLPLMEGL

STDQTETSSLTESVSSSSGLGEEEPPALPSKLLSSGSCKADLGCRSYTDE

LHAVAPL

IL-17RE, transcript variant 1, is encoded by the following mRNA sequence (NCBI Accession No. NM_153480 and SEQ ID NO: 27):

```
   1 cgagggctcc tgctggtact gtgttcgctg ctgcacagca aggccctgcc acccaccttc
  61 aggccatgca gccatgttcc gggagcccta attgcacaga gcccATGgg gagctccaga
 121 ctggcagccc tgctcctgcc tctcctcctc atagtcatcg acctctctga ctctgctggg
 181 attggctttc gccacctgcc ccactggaac acccgctgtc ctctggcctc ccacacggat
 241 gacagtttca ctggaagttc tgcctatatc ccttgccgca cctggtgggc cctcttctcc
 301 acaaagcctt ggtgtgtgcg agtctggcac tgttcccgct gtttgtgcca gcatctgctg
 361 tcaggtggct caggtcttca acggggcctc ttccacctcc tggtgcagaa atccaaaaag
 421 tcttccacat tcaagttcta taggagacac aagatgccag cacctgctca gaggaagctg
 481 ctgcctcgtc gtcacctgtc tgagaagagc catcacattt ccatccctc cccagacatc
 541 tcccacaagg gacttcgctc taaaaggacc caaccttcgg atccagagac atgggaaagt
 601 cttcccagat tggactcaca aaggcatgga ggacccgagt tctcctttga tttgctgcct
 661 gaggcccggg ctattcgggt gaccatatct tcaggccctg aggtcagcgt gcgtctttgt
 721 caccagtggg cactggagtg tgaagagctg agcagtccct atgatgtcca gaaaattgtg
 781 tctgggggcc acactgtaga gctgccttat gaattccttc tgccctgtct gtgcatagag
 841 gcatcctacc tgcaagagga cactgtgagg cgcaaaaaat gtcccttcca gagctggcca
 901 gaagcctatg gctcggactt ctggaagtca gtgcacttca ctgactacag ccagcacact
 961 cagatggtca tggccctgac actccgctgc ccactgaagc tggaagctgc cctctgccag
1021 aggcacgact ggcatacct tgcaaagac ctcccgaatg ccacagctcg agagtcagat
1081 gggtggtatg ttttggagaa ggtggacctg cacccccagc tctgcttcaa gttctctttt
1141 ggaaacagca gccatgttga atgcccccac cagactgggt ctctcacatc ctggaatgta
1201 agcatggata cccaagccca gcagctgatt cttcacttct cctcaagaat gcatgccacc
1261 ttcagtgctg cctggagcct cccaggcttg gggcaggaca ctttggtgcc ccccgtgtac
1321 actgtcagcc aggcccgggg ctcaagccca gtgtcactag acctcatcat tcccttcctg
1381 aggccagggt gctgtgtcct ggtgtggcgg tcagatgtcc agtttgcctg aagcacctc
1441 ttgtgtccgg atgtctctta cagacacctg gggctcttga tcctggcact gctggccctc
1501 ctcaccctac tgggtgttgt tctggccctc acctgccggc gccacagtc aggcccgggc
1561 ccagcgcggc cagtgctcct cctgcacgcg gcggactcgg aggcgcagcg gcgcctggtg
1621 ggagcgctgg ctgaactgct acgggcagcg ctgggcggcg ggcgcgacgt gatcgtggac
1681 ctgtgggagg ggaggcacgt ggcgcgcgtg ggcccgctgc cgtggctctg ggcggcgcgg
1741 acgcgcgtag cgcgggagca gggcactgtg ctgctgctgt ggagcggcgc cgaccttcgc
1801 ccggtcagcg gccccgaccc ccgcgccgcg ccctgctcg ccctgctcca cgctgccccg
1861 cgcccgctgc tgctgctcgc ttacttcagt cgcctctgcg ccaagggcga catccccccg
1921 ccgctgcgcg ccctgccgcg ctaccgcctg ctgcgcgacc tgccgcgtct gctgcgggcg
1981 ctggacgcgc ggcctttcgc agaggccacc agctggggcc gccttgggc gcggcagcgc
2041 aggcagagcc gcctagagct gtgcagccgg ctcgaacgag aggccgcccg acttgcagac
2101 ctaggttgag cagagctcca ccgcagtccc gggtgtctgc ggccgcaacg caacggacac
```

-continued

```
2161 tggctggaac cccggaatga gccttcgacc ctgaaatcct tggggtgcct cgaggacgac 2221 tggccgaaaa gccgcattcc ctgcctcaca ggccggaagt cccagcccag tccccgcgcg 2281 cgtccctctt cctcctcata ctttcccttg actgagagct cctctaaccc ctgttctgat 2341 ggggagggc ggtcttccca cttcctctcc agaactccag aaagagcagt gtgcttatgc 2401 ttcagtccag gctggagagg ttggggccgg ggtagggagg caggagccat gtcagttctg 2461 aaggagggtg aggcggtggg ggattgcagg gggcggctga gagaaaacct ccttgggggc 2521 cagggattcc ctttcccact ctgaggctct ggccagaggg agagaggact ctggacctag 2581 gaaaagaggc ttttggctcc aggtggtcag gacagtgggg gttgggggtg gggtgggtgg 2641 gtgctggcgg tggggaccaa gatccggaaa gatgaataaa gacaaacatg acaaactaag 2701 aaaaaaaaaa aaaaaaa
```

IL-17RE, transcript variant 1, is encoded by the following amino acid sequence (NCBI Accession No. NM_153480 and SEQ ID NO: 28):

MGSSRLAALLLPLLLIVIDLSDSAGIGFRHLPHWNTRCPLASHTDDSFTG

SSAYIPCRTWWALFSTKPWCVRVWHCSRCLCQHLLSGGSGLQRGLFHLLV

QKSKKSSTFKFYRRHKMPAPAQRKLLPRRHLSEKSHHISIPSPDISHKGL

RSKRTQPSDPETWESLPRLDSQRHGGPEFSFDLLPEARAIRVTISSGPEV

SVRLCHQWALECEELSSPYDVQKIVSGGHTVELPYEFLLPCLCIEASYLQ

EDTVRRKKCPFQSWPEAYGSDFWKSVHFTDYSQHTQMVMALTLRCPLKLE

AALCQRHDWHTLCKDLPNATARESDGWYVLEKVDLHPQLCFKFSFGNSSH

VECPHQTGSLTSWNVSMDTQAQQLILHFSSRMHATFSAAWSLPGLGQDTL

VPPVYTVSQARGSSPVSLDLIIPFLRPGCCVLVWRSDVQFAWKHLLCPDV

SYRHLGLLILALLALLTLLGVVLALTCRRPQSGPGPARPVLLLHAADSEA

QRRLVGALAELLRAALGGGRDVIVDLWEGRHVARVGPLPWLWAARTRVAR

EQGTVLLLWSGADLRPSGPDPRAAPLLALLHAAPRPLLLLAYFSRLCAKG

DIPPPLRALPRYRLLRDLPRLLRALDARPFAEATSWGRLGARQRRQSRLE

LCSRLEREAARLADLG

IL-17RE, transcript variant 2, is encoded by the following mRNA sequence (NCBI Accession No. NM_153481 and SEQ ID NO: 29):

```
   1 cgagggctcc tgctggtact gtgttcgctg ctgcacagca aggccctgcc acccaccttc 61 aggccatgca gccatgttcc gggagcccta attgcacaga agcccatggg gagctccaga 121 ctggcagccc tgctcctgcc tctcctcctc atagtcatcg acctctctga ctctgctggg 181 attggctttc gccacctgcc ccactggaac acccgctgtc ctctggcctc ccacacggtc 241 ttcaacgggg cctcttccac ctcctggtgc agaaatccaa aaagtcttcc acattcaagt 301 tctataggag acacaagATG ccagcacctg ctcagaggaa gctgctgcct cgtcgtcacc 361 tgtctgagaa gagccatcac atttccatcc cctccccaga catctcccac aagggacttc 421 gctctaaaag gacccaacct tcggatccag agacatggga aagtcttccc agattggact 481 cacaaaggca tggaggaccc gagttctcct ttgatttgct gcctgaggcc cgggctattc 541 gggtgaccat atcttcaggc cctgaggtca gcgtgcgtct ttgtcaccag tgggcactgg 601 agtgtgaaga gctgagcagt ccctatgatg tccagaaaat tgtgtctggg ggccacactg 661 tagagctgcc ttatgaattc cttctgccct gtctgtgcat agaggcatcc tacctgcaag 721 aggacactgt gaggcgcaaa aaatgtccct tccagagctg gccagaagcc tatggctcgg 781 acttctgaa gtcagtgcac ttcactgact acagccagca cactcagatg gtcatggccc 841 tgacactccg ctgcccactg aagctggaag ctgccctctg ccagaggcac gactggcata 901 cccttgcaa agacctcccg aatgccacag ctcgagagtc agatgggtgg tatgttttgg 961 agaaggtgga cctgcacccc cagctctgct tcaagttctc ttttggaaac agcagccatg 1021 ttgaatgccc ccaccagact gggtctctca catcctggaa tgtaagcatg gatacccaag
```

```
1081 cccagcagct gattcttcac ttctcctcaa gaatgcatgc caccttcagt gctgcctgga 1141 gcctcccagg cttggggcag gacactttgg tgcccccgt gtacactgtc agccaggccc 1201 ggggctcaag cccagtgtca ctagacctca tcattcctt cctgaggcca gggtgctgtg 1261 tcctggtgtg gcggtcagat gtccagtttg cctggaagca cctcttgtgt ccggatgtct 1321 cttacagaca cctgggctc ttgatcctgg cactgctggc cctcctcacc ctactgggtg 1381 ttgttctggc cctcacctgc cggcgccac agtcaggccc gggcccagcg cggccagtgc 1441 tcctcctgca cgcggcggac tcggaggcgc agcggcgcct ggtgggagcg ctggctgaac 1501 tgctacgggc agcgctgggc ggcgggcgcg acgtgatcgt ggacctgtgg gaggggaggc 1561 acgtggcgcg cgtgggcccg ctgccgtggc tctggcggc gcggacgcgc gtagcgcggg 1621 agcagggcac tgtgctgctg ctgtggagcg gcgccgacct tgcccggtc agcggcccg 1681 accccgcgc cgcgcccctg ctcgcccctgc tccacgctgc cccgcgcccg ctgctgctgc 1741 tcgcttactt cagtcgcctc tgcgccaagg gcgacatccc ccgccgctg cgcgccctgc 1801 cgcgctaccg cctgctgcgc gacctgccgc gtctgctgcg ggcgctggac gcgcggcctt 1861 tcgcagaggc caccagctgg ggccgccttg gggcgcggca gcgcaggcag agccgcctag 1921 agctgtgcag ccggctcgaa cgagaggccg cccgacttgc agacctaggt tgagcagagc 1981 tccaccgcag tcccgggtgt ctgcggccgc aacgcaacgg acactggctg aacccccgga 2041 atgagccttc gaccctgaaa tccttggggt gcctcgagga cgactggccg aaaagccgca 2101 ttccctgcct cacaggccgg aagtcccagc ccagtccccg cgcgcgtccc tcttcctcct 2161 catactttcc cttgactgag agctcctcta acccctgttc tgatgggga gggcggtctt 2221 cccacttcct ctccagaact ccagaaagag cagtgtgctt atgcttcagt ccaggctgga 2281 gaggttgggg ccggggtagg gaggcaggag ccatgtcagt tctgaaggag ggtgaggcgg 2341 tgggggattg caggggggcgg ctgagagaaa acctccttgg gggccaggga ttcccttcc 2401 cactctgagg ctctggccag agggagagag gactctggac ctaggaaaag aggcttttgg 2461 ctccaggtgg tcaggacagt gggggttggg ggtggggtgg gtgggtgctg gcggtgggga 2521 ccaagatccg gaaagatgaa taaagacaaa catgacaaac taagaaaaaa aaaaaaaaa 2581 a
```

IL-17RE, transcript variant 2, is encoded by the following amino acid sequence (NCBI Accession No. NM_153481 and SEQ ID NO: 30):

MPAPAQRKLLPRRHLSEKSHHISIPSPDISHKGLRSKRTQPSDPETWESL
PRLDSQRHGGPEFSFDLLPEARAIRVTISSGPEVSVRLCHQWALECEELS
SPYDVQKIVSGGHTVELPYEFLLPCLCIEASYLQEDTVRRKKCPFQSWPE
AYGSDFWKSVHFTDYSQHTQMVMALTLRCPLKLEAALCQRHDWHTLCKDL
PNATARESDGWYVLEKVDLHPQLCFKFSFGNSSHVECPHQTGSLTSWNVS
MDTQAQQLILHFSSRMHATFSAAWSLPGLGQDTLVPPVYTVSQARGSSPV
SLDLIIPFLRPGCCVLVWRSDVQFAWKHLLCPDVSYRHLGLLILALLALL
TLLGVVLALTCRRPQSGPGPARPVLLLHAADSEAQRRLVGALAELLRAAL
GGGRDVIVDLWEGRHVARVGPLPWLWAARTRVAREQGTVLLLWSGADLRP
VSGPDPRAAPLLALLHAAPRPLLLLAYFSRLCAKGDIPPPLRALPRYRLL
RDLPRLLRALDARPFAEATSWGRLGARQRRQSRLELCSRLEREAARLADL
G

IL-17RE, transcript variant 5, is encoded by the following mRNA sequence (NCBI Accession No. NM_153483 and SEQ ID NO: 31):

```
  1 ggtgcgtccc ccaacctgat gctagcccct ttcctgttac ttctcaccca cagcaggagc 61 cccttgtctt tcaggccatg cagccatgtt ccgggagccc taattgcaca gaagcccATG

121 gggagctcca gactggcagc cctgctcctg cctctcctcc tcatagtcat cgacctctct 181 gactctgctg ggattggctt tcgccacctg ccccactgga acacccgctg tcctctggcc
```

-continued

```
 241 tcccacacgg atgacagttt cactggaagt tctgcctata tcccttgccg cacctggtgg 301 gccctcttct ccacaaagcc ttggtgtgtg cgagtctggc actgttcccg ctgtttgtgc 361 cagcatctgc tgtcaggtgg ctcaggtctt caacggggcc tcttccacct cctggtgcag 421 aaatccaaaa agtcttccac attcaagttc tataggagac acaagatgcc agcacctgct 481 cagaggaagc tgctgcctcg tcgtcacctg tctgagaaga gccatcacat ttccatcccc 541 tccccagaca tctcccacaa gggacttcgc tctaaaagga cccaaccttc ggatccagag 601 acatgggaaa gtcttcccag attggactca caaaggcatg gaggacccga gttctccttt 661 gatttgctgc ctgaggcccg ggctattcgg gtgaccatat cttcaggccc tgaggtcagc 721 gtgcgtcttt gtcaccagtg ggcactggag tgtgaagagc tgagcagtcc ctatgatgtc 781 cagaaaattg tgtctggggg ccacactgta gagctgcctt atgaattcct tctgccctgt 841 ctgtgcatag aggcatccta cctgcaagag acactgtga ggcgcaaaaa atgtcccttc 901 cagagctggc cagaagccta tgctcggac ttctggaagt cagtgcactt cactgactac 961 agccagcaca ctcagatggt catggccctg acactccgct gcccactgaa gctggaagct 1021 gccctctgcc agaggcacga ctggcatacc ctttgcaaag acctcccgaa tgccacagct 1081 cgagagtcag atgggtggta tgttttggag aaggtggacc tgcaccccca gctctgcttc 1141 aagttctctt ttggaaacag cagccatgtt gaatgccccc accagactgg gtctctcaca 1201 tcctggaatg taagcatgga tacccaagcc cagcagctga ttcttcactt ctcctcaaga 1261 atgcatgcca ccttcagtgc tgcctggagc ctcccaggct gggggcagga cactttggtg 1321 ccccccgtgt acactgtcag ccaggcccgg ggctcaagcc cagtgtcact agacctcatc 1381 attcccttcc tgaggccagg gtgctgtgtc ctggtgtggc ggtcagatgt ccagtttgcc 1441 tggaagcacc tcttgtgtcc ggatgtctct tacagacacc tggggctctt gatcctggca 1501 ctgctggccc tcctcaccct actgggtgtt gttctggccc tcacctgccg gcgcccacag 1561 tcaggcccgg gccagcgcg ccagtgctc ctcctgcacg cggcggactc ggaggcgcag 1621 cggcgcctgg tgggagcgct ggctgaactg ctacgggcag cgctgggcgg cgggcgcgac 1681 gtgatcgtgg acctgtggga ggggaggcac gtggcgcgcg tgggcccgct gccgtggctc 1741 tgggcggcgc ggacgcgcgt agcgcgggag cagggcactg tgctgctgct gtggagcggc 1801 gccgaccttc gccggtcag cggccccgac cccgcgccg cgccctgct cgccctgctc 1861 cacgctgccc cgcgcccgct gctgctgctc gcttacttca gtcgcctctg cgccaagggc 1921 gacatccccc cgccgctgcg cgccctgccg cgctaccgcc tgctgcgcga cctgccgcgt 1981 ctgctgcggg cgctggacgc gcggcctttc gcagaggcca ccagctgggg ccgccttggg 2041 gcgcggcagc gcaggcagag ccgcctagag ctgtgcagcc ggctcgaacg agaggccgcc 2101 cgacttgcag acctaggttg agcagagctc accgcagtc ccgggtgtct gcggccgcaa 2161 cgcaacggac actggctgga accccggaat gagccttcga ccctgaaatc cttggggtgc 2221 ctcgaggacg actggccgaa aagccgcatt ccctgcctca caggccggaa gtcccagccc 2281 agtcccgcg cgcgtccctc ttcctcctca tactttccct tgactgagag ctcctctaac 2341 ccctgttctg atggggagg gcggtcttcc cacttcctct ccagaactcc agaaagagca 2401 gtgtgcttat gcttcagtcc aggctggaga ggttggggcc gggtaggga ggcaggagcc 2461 atgtcagttc tgaaggaggg tgaggcggtg ggggattgca gggggcggct gagagaaaac
```

```
2521 ctccttgggg gccagggatt ccctttccca ctctgaggct ctggccagag ggagagagga 2581 ctctggacct aggaaaagag gcttttggct ccaggtggtc aggacagtgg gggttggggg 2641 tggggtgggt gggtgctggc ggtggggacc aagatccgga aagatgaata aagacaaaca 2701 tgacaaacta agaaaaaaaa aaaaaaaa
```

IL-17RE, transcript variant 5, is encoded by the following amino acid sequence (NCBI Accession No. NM_153483 and SEQ ID NO: 32):

MGSSRLAALLLPLLLIVIDLSDSAGIGFRHLPHWNTRCPLASHTDDSFTG

SSAYIPCRTWWALFSTKPWCVRVWHCSRCLCQHLLSGGSGLQRGLFHLLV

QKSKKSSTFKFYRRHKMPAPAQRKLLPRRHLSEKSHHISIPSPDISHKGL

RSKRTQPSDPETWESLPRLDSQRHGGPEFSFDLLPEARAIRVTISSGPEV

SVRLCHQWALECEELSSPYDVQKIVSGGHTVELPYEFLLPCLCIEASYLQ

EDTVRRKKCPFQSWPEAYGSDFWKSVHFTDYSQHTQMVMALTLRCPLKLE

AALCQRHDWHTLCKDLPNATARESDGWYVLEKVDLHPQLCFKFSFGNSSH

VECPHQTGSLTSWNVSMDTQAQQLILHFSSRMHATFSAAWSLPGLGQDTL

VPPVYTVSQARGSSPVSLDLIIPFLRPGCCVLVWRSDVQFAWKHLLCPDV

SYRHLGLLILALLALLTLLGVVLALTCRRPQSGPGPARPVLLLHAADSEA

QRRLVGALAELLRAALGGGRDVIVDLWEGRHVARVGPLPWLWAARTRVAR

EQGTVLLLWSGADLRPVSGPDPRAAPLLALLHAAPRPLLLLAYFSRLCAK

GDIPPPLRALPRYRLLRDLPRLLRALDARPFAEATSWGRLGARQRRQSRL

ELCSRLEREAARLADLG

Silencing Expression with MicroRNAs

The invention comprises compositions with means to inhibit the activity of IL-17 or an IL-17R, by delivering microRNA (miRNA) molecules to an ocular or adnexal tissue with an appropriate pharmaceutical carrier. Compositions that comprise a miRNA targeted to either IL-17 or an IL-17R antagonize the function of an IL-17R. The composition comprises one or more miRNA(s) that bind to one or more regions of IL-17 or an IL-17R. The following table contains exemplary miRNAs that have been shown to partially or completely silence the expression of human IL-17 or an IL-17R.

TABLE 1

Summary of miRNAs, their human target genes, nucleotide sequences, and their sequence identifier numbers.

| Target Gene | miRNA | Polynucleotide sequence (5' to 3') | SEQ ID NO: |
|---|---|---|---|
| IL-17R | miR-24 | UGGCUCAGUUCGGAACAG | 33 |
| IL-17R | miR-378 | CUCCUGACUCCAGGUCCUGUGU | 34 |
| IL-17R | Let-7g | UGAGGUAGUAGUUUGUACAGU | 35 |

Pharmaceutically-Appropriate Carriers

Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist.

Optionally, the composition further contains a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

Drug Delivery by Contact Lens

The invention comprises a contact lens and a composition that inhibits an activity of an inflammatory interleukin-1 cytokine. For example, the composition is incorporated into or coated onto said lens. The composition is chemically bound or physically entrapped by the contact lens polymer. Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of the invention include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, fluorofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyfluflocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A.

Exemplary materials used to fabricate a hydrophilic lens with means to deliver the compositions of the invention include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A.

Antibody Compositions:

Compositions of the claimed invention comprise at least one antibody. This antibody is either monoclonal or polyclonal. The claimed antibody targets an intracellular or extracellular IL-17 cytokine or IL-17 receptor, preferably, the IL-17A or F cytokine or the IL-17RA or IL-17RC receptor. This antibody binds to at least one intracellular or extracellular sequence, or epitope, of an IL-17 cytokine or IL-17 receptor. In certain embodiments, the claimed antibody is a single-chain antibody. Alternatively, the antibody is a humanized, recombinant, or chimeric antibody. This antibody is optionally derived from commercially-available antibodies designed for in vitro or in vivo use. The claimed antibody is conjugated directly or indirectly to one or more compound(s) that inhibit or modify the activity of an IL-17 cytokine or an IL-17 receptor. Alternatively, the claimed antibody is an intracellular antibody, or intrabody.

The claimed antibody binds to one or more regions of an IL-17 cytokine. Exemplary regions to which the claimed antibody binds include, but are not limited to, an intracellular domain, an extracellular domain, a catalytic domain, a protein-binding domain, a ligand-binding domain, a scaffolding domain, a signal peptide, a domain of an immature cytokine, a precursor domain, a fibronectin domain, a linker region, a regulatory domain, an oligomerization domain, or a signaling domain.

EXAMPLES

Example 1

CD4$^+$IL-17$^+$ T Cell Abundance in a Mouse Model of DES

Dry Eye Syndrome (DES) was induced in mice by subcutaneous injection of scopolamine and placement in controlled-environment chambers. Following induction of DES and an incubation period, the abundance of CD4$^+$IL-17$^+$ T cells in draining lymph nodes was measured using flow cytometry. For Examples 1-4, the monoclonal anti-mouse IL-17 antibody used was obtained from R&D Systems, Inc. (Clone: 50104, Cat. #MAB421). FIG. 1 shows that the abundance of IL-17-producing CD4$^+$ T cells in the draining lymph nodes of mice with DES increases compared to those of healthy controls.

Example 2

IL-17 mRNA Expression in Conjunctiva of DES Mice

Figure 2:
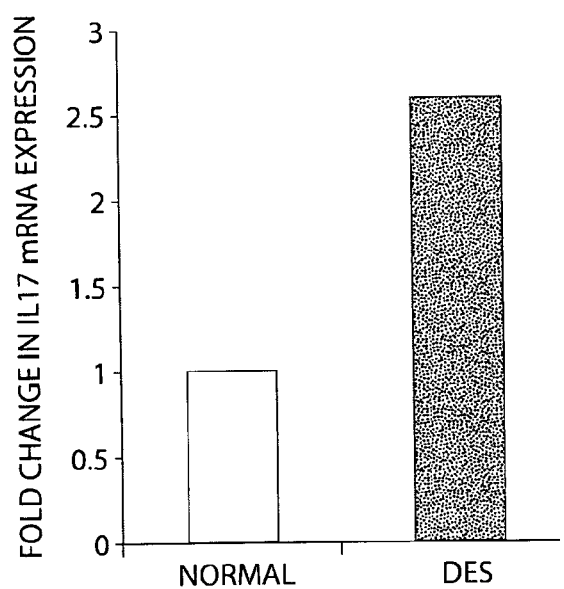
FIG. 2 is a graph showing the fold change in IL-17 expression in normal versus DES mice. Conjunctiva of mice with DES expresses approximately a 2.5-3 fold increase in IL-17 mRNA abundance compared to those of normal mice.

IL-17 mRNA transcripts expressed within the conjunctiva of DES versus normal mice was quantified using real time polymerase chain reaction (PCR). The conjunctiva is the thin, transparent tissue that covers the outer surface of the eye. This structure begins at the outer edge of the cornea, covering the visible part of the sclera, and lining the inside of the eyelids. DES mice demonstrated a three fold increase in the abundance of IL-17 mRNA transcripts in this structure compared to healthy controls, as shown in FIG. 2.

Example 3

IL-17RA Expression on Ocular Surfaces

Figure 3A:
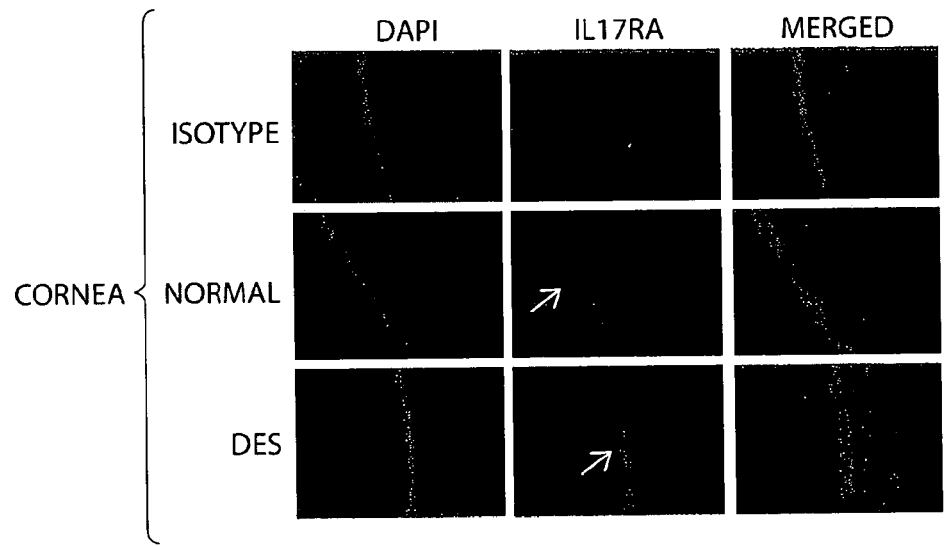
FIG. 3A-B is a pair of photographs of immunofluorescence showing that IL-17RAs are constitutively expressed on the epithelium of (A) cornea and (B) conjunctiva of both normal mice as well as mice with DES.
Figure 3B:
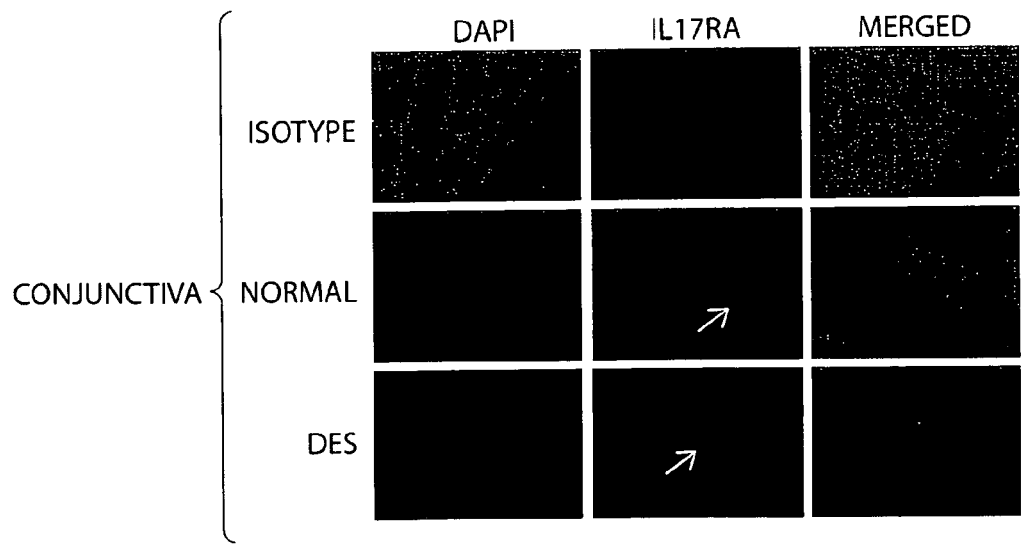
Figure 4A:
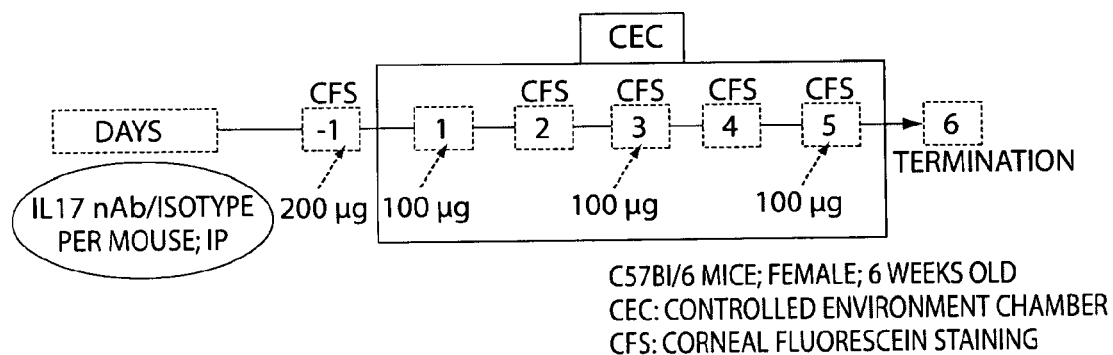
FIG. 4A is a schematic diagram of the experimental design for FIGS. 4B, 4C, and 4D.
Figure 4B:
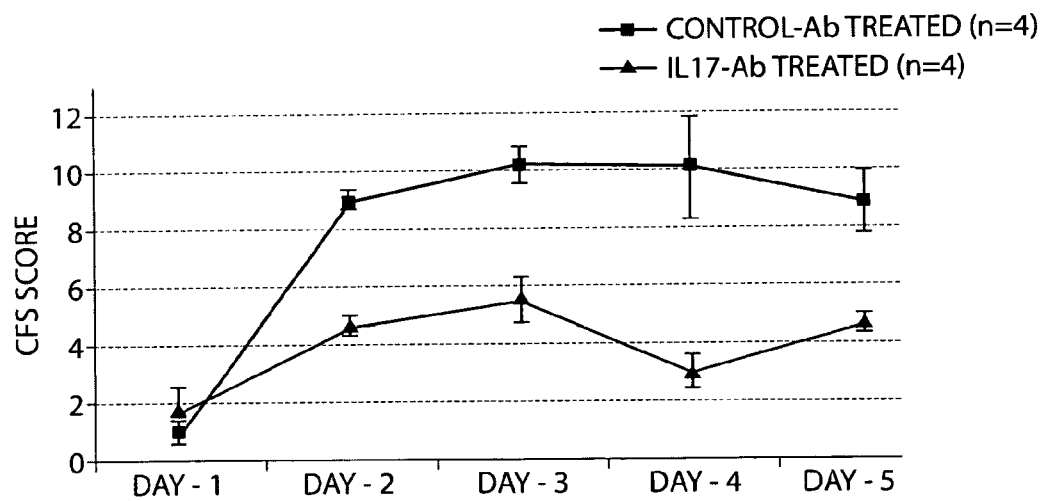
FIG. 4B is a graph showing the CFS score on days 1-5 of either control or IL-17 Ab treated corneas. More than 50% reduction in the DES-clinical score was observed during induction as well as progression phase of the disease in mice treated with anti-IL-17 antibody compared to those treated with control antibody
Figure 4C:
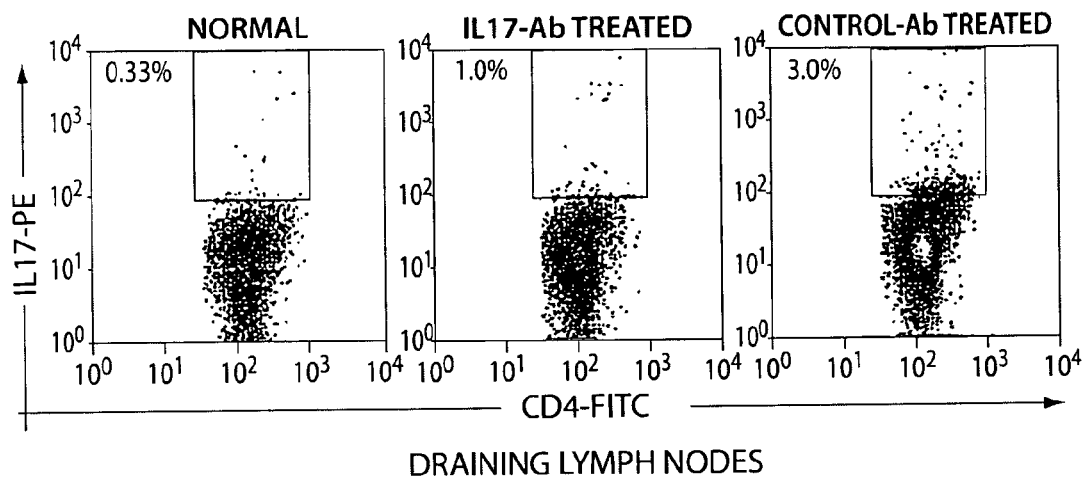
FIG. 4C is a series of graphs depicting flow cytometric dots demonstrating that a decreased frequency of IL-17+CD4+ T cells was observed in the draining lymph nodes of anti-IL-17 antibody treated group as compared to those of the control-antibody treated group.
Figure 4D:
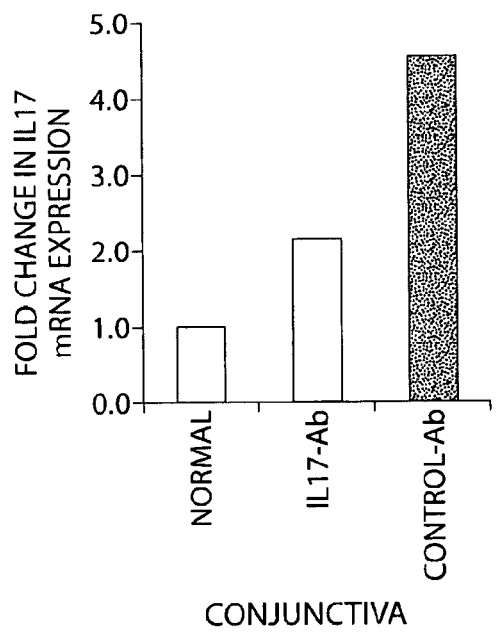
FIG. 4D is a graph of the fold change in IL-17 mRNA expression in the conjunctiva of normal versus either IL-17 or Control Ab-treated groups. Conjunctiva of mice treated with anti-IL-17 antibody showed decreased IL-17 mRNA expression than those of treated with control antibody.

IL-17 receptor expression on ocular surfaces was analyzed using immunofluorescence microscopy. In contrast to the dramatic upregulation of IL-17 mRNA in the conjunctiva of DES mice, FIG. 3 shows that IL-17RA protein was constitutively expressed on corneal as well as conjunctival epithelium of both DES and control groups.

Example 4

In Vivo Blockade of IL-17 in DES Mice

Healthy and DES mice were intraperitoneally injected with neutralizing anti-IL-17 antibodies to determine the effect of blocking IL-17 activity on both the induction and progression of DES. The results showed a significant decrease in the intensity of clinical signs of DES (measured by corneal fluorescein staining (CFS) scoring) during the induction as well as the progression phases of the disease in the anti-IL-17 antibody-treated group as compared to the control antibody-treated group (shown in FIG. 4, panels a and b). Furthermore, lymph nodes and conjunctiva of the anti-IL-17 antibody-treated group showed reductions in the abundance of Th17 cells and the expression of IL-17 mRNA, respectively, compared to the control-antibody treated group (shown in FIG. 4, panels c and d).

FIG. 5 shows the oxford schema for grading corneal and conjunctival staining used for scoring clinical severity in this example.

Example 5

Recovery of Regulatory T-Cell (Treg) Suppressor Function by Anti-IL-17 Therapy

Figure 7:
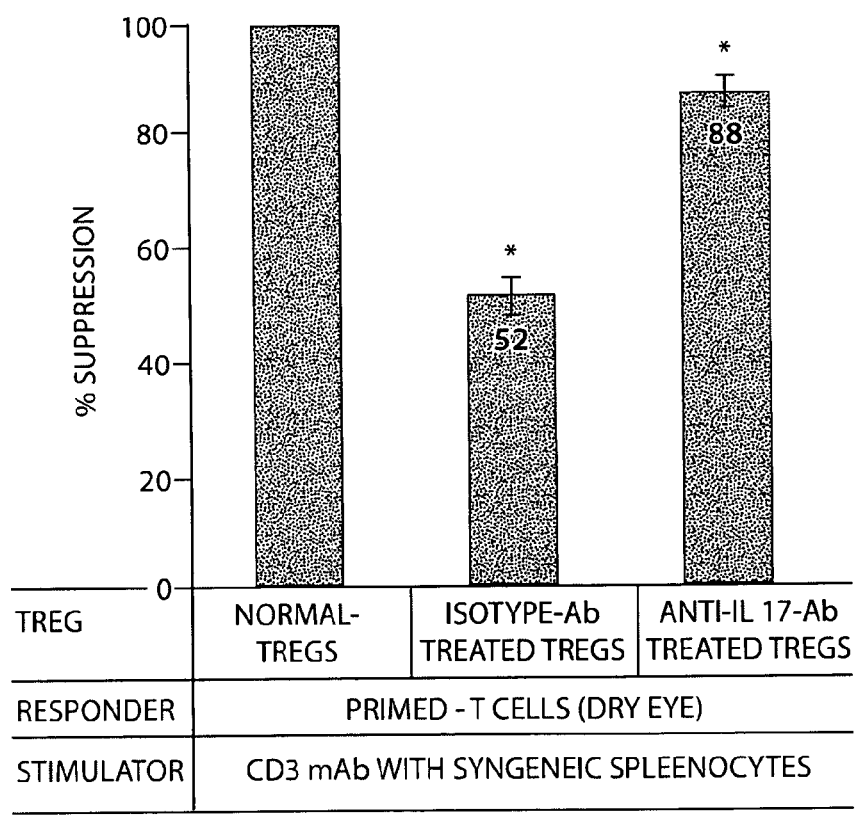
FIG. 7 is a graph showing the results of an in vitro regulatory T cell (Treg) suppression assay using CD3 stimulated primed-T cells (isolated from the LN of dry eye mice) and Tregs (isolated from the LN of mice treated with anti-IL-17 or isotype antibodies). The data show a significant recovery in the suppressor potential of Tregs only in mice treated with anti-IL-17 antibody (i.p.) compared to those isolated from the isotype antibody treated groups (p=0.029). The suppressor potential of Tregs isolated from different groups is calculated in relation to the suppression potential of Tregs of normal mice, considered as 100%. The data suggest a reversal of regulatory-T cell (Treg) suppressor function by anti-IL-17 therapy.

The in vitro Treg suppression assay using CD3 stimulated primed-T cells (isolated from the LN of dry eye mice) and Tregs (isolated from the LN of mice treated with anti-IL-17 or isotype antibodies) shows a significant recovery in the suppressor potential of Tregs only in mice treated with anti-IL-17 antibody (i.p.) compared to those isolated from the isotype antibody treated groups (p=0.029). The suppressor potential of Tregs isolated from different groups is calculated in relation to the suppression potential of Tregs of normal mice, considered as 100% (FIG. 7).

In dry eye disease there is a significant functional loss of Treg suppression of about 50%. Anti-IL-17 antibody treatment promotes Treg function and restores and/or augments Treg-mediated immune suppression.

Example 6

Topical Application of Anti-IL-17 Antibody Ameliorates Dry Eye Disease

Figure 8A:
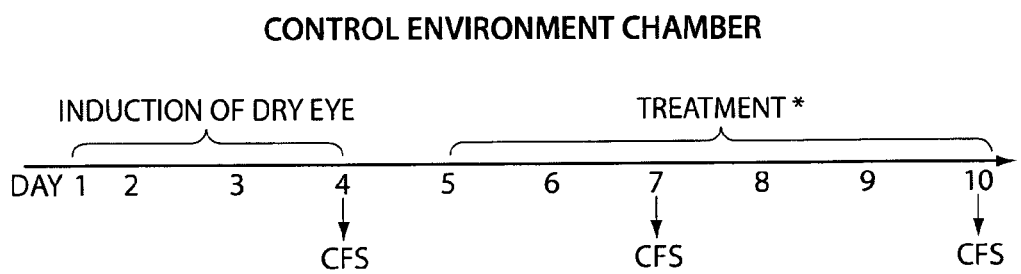
FIG. 8A is a schematic diagram of the experimental design to study the effects of in vivo IL-17 blockade using topical application of anti-IL-17 antibody or isotype-antibody on clinical signs.
Figure 8B:
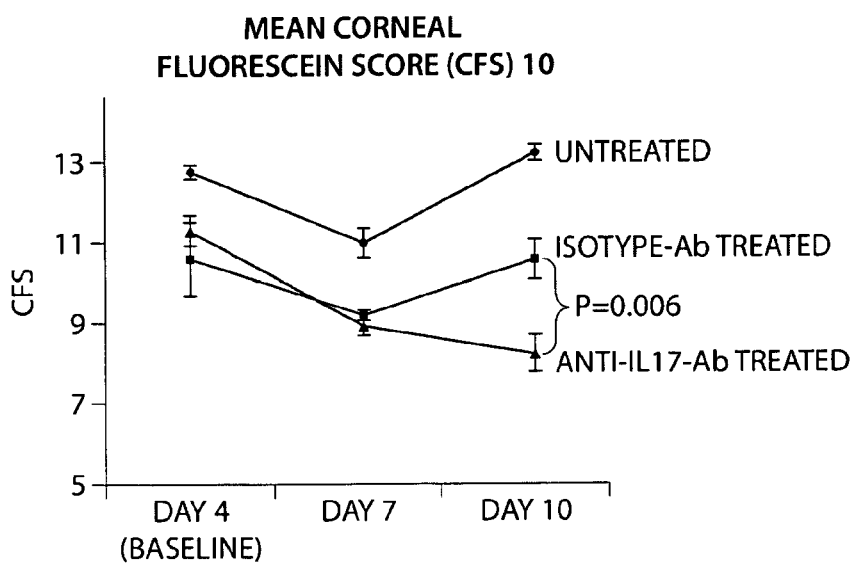
FIG. 8B is a graph showing corneal fluorescein staining (CFS) scores, a readout for the principal clinical sign of dry eye, in anti-IL-17 antibody-treated, isotype antibody-treated and untreated groups from Day 4 (base line) to Day 10.
Figure 8C:
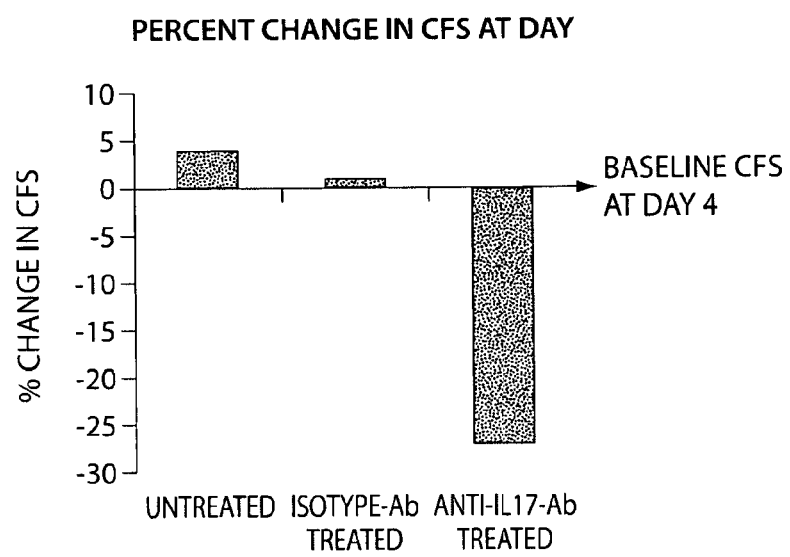
FIG. 8C is a graph showing the percent change in CFS scores at Day 10 from baseline CFS scores (Day 4) in different groups. CFS scores are significantly lower in anti-IL-17 antibody-treated mice compared to isotype antibody-treated and untreated groups.

FIG. 8A shows a schematic diagram of the experimental design to study the effects of in vivo IL-17 blockade using topical application of anti-IL17-antibody or isotype-antibody on clinical signs. CFS are significantly lower in anti-IL-17 antibody-treated mice compared to isotype antibody-treated and untreated groups (FIGS. 8B and 8C).

Example 7

Figure 9:
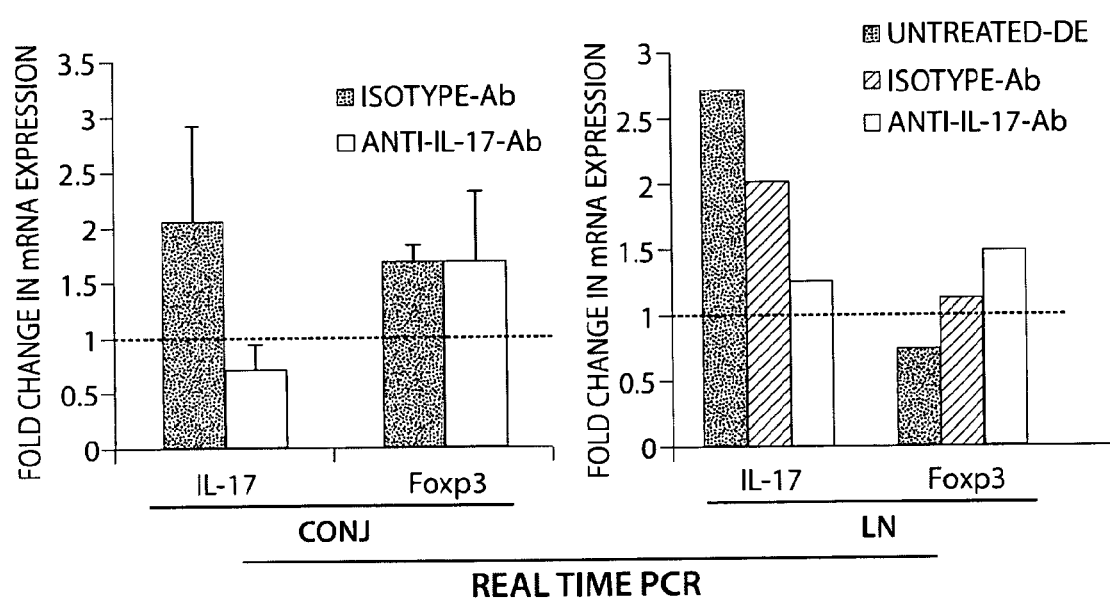
FIG. 9 is a pair of graphs showing that topical application of anti-IL-17 antibody reduces frequencies of pathogenic Th17 cells both in conjunctiva (Conj) (left) and the draining lymph nodes (LN) (right). Conjunctiva and the draining lymph nodes were harvested at day 10 (as shown in FIG. 8) from anti-IL-17 antibody and isotype antibody treated mice. Real-time PCR was performed to analyze mRNA expression levels of IL-17 (Th17 cells) and Foxp3 (Treg cells). Dotted line represents mRNA levels in normal controls.

Topical Application of Anti-IL-17 Antibody Reduces Frequencies of Pathogenic Th17 Cells Both in Conjunctiva and the Draining Lymph Nodes Conjunctiva and the draining lymph nodes were harvested at Day 10 (as shown in FIG. 8) from Anti-IL17 antibody and Isotype antibody treated mice. Real-time PCR was performed to analyze mRNA expression levels of IL-17 (Th17 cells) and Foxp3 (Treg cells). FIGS. 9A and 9B show that treatment with an anti-IL-17 antibody specifically decreases expression of IL-17 in Th17 cells of the conjunctiva and lymph nodes.

Example 8

Figure 10A:
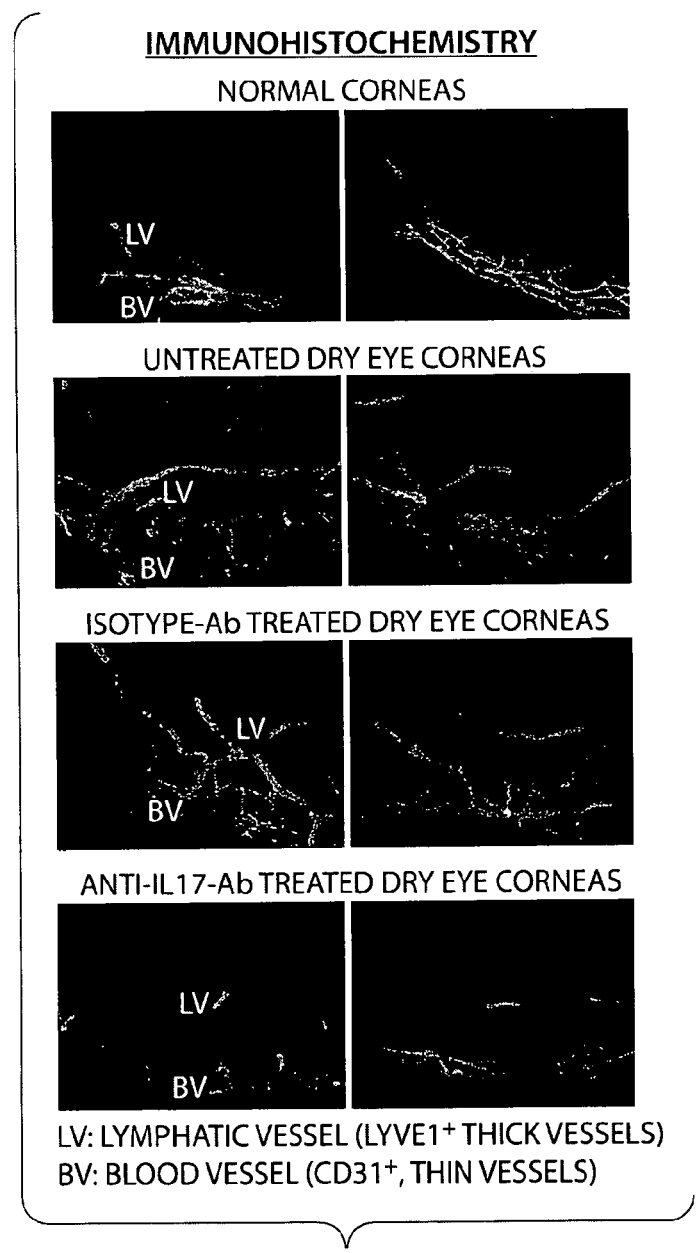
FIG. 10A is a series of micrographs showing that topical application of anti-IL-17 antibody inhibits dry eye induced corneal lymphatic vessels via decreased secretion of lymphangiogenesis-specific growth factors, particularly VEGF-C and -D in dry eye corneas. Induction of new lymphatic vessels in dry eye corneas facilitate the migration of resident corneal antigen presenting cells to the draining lymph nodes which in turn induce generation of adaptive immunity to ocular surface. Representative micrographs of corneal whole mounts showing lymphatic vessels (LV) and blood vessels (BV) in different groups.
Figure 10B:
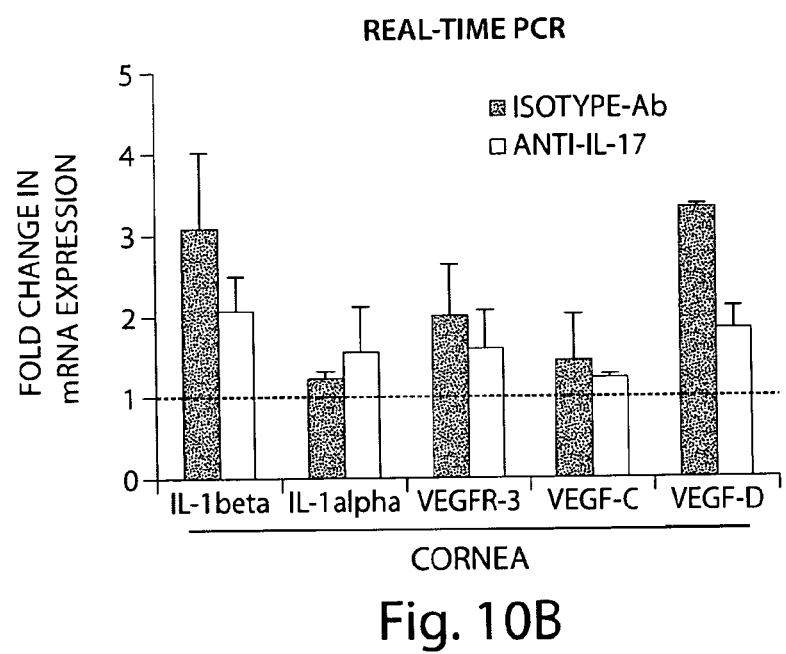
FIG. 10B is a graph showing that topical application of anti-IL-17 antibody inhibits dry eye induced corneal lymphatic vessels via decreased secretion of lymphangiogenesis-specific growth factors, particularly VEGF-C and -D in dry eye corneas. Induction of new lymphatic vessels in dry eye corneas facilitate the migration of resident corneal antigen presenting cells to the draining lymph nodes which in turn induce generation of adaptive immunity to ocular surface. Real-time PCR analysis of whole cornea showing mRNA levels of Interleukin-1 (IL1)-beta, IL1-alpha, and lymphatic vessel-specific growth factors VEGF-C and -D, and their cognate receptor, VEGFR-3. Dotted line represents mRNA levels in cornea of normal controls.

Topical Application of Anti-IL-17 Antibody Inhibits Dry Eye Induced Corneal Lymphatic Vessels via Decreased Secretion of Lymphangiogenesis-Specific Growth Factors, Particularly VEGF-C and D in Dry Eye Corneas Induction of new lymphatic vessels in dry eye corneas facilitate the migration of resident corneal antigen presenting cells to the draining lymph nodes, which, in turn, induce generation of adaptive immunity to ocular surface. Untreated and control Ab treated Dry Eye groups show an invasion of lymphatic vessels into the cornea (FIG. 10A), compared to Normal cornea. Treatment with anti-IL-17 antibody decreases invasion of lymphatic vessels into the cornea (FIG. 10A). Anti-IL17 antibody treatment decreases mRNA expression of known angiogenic molecules, such as VEGF-C, VEGF-D, and VEGFR-3 (FIG. 10B).

Example 9

Topical Application of Anti-IL-17 Antibody Maintains the Normal Phenotype of CD11b+ Cells in Cornea Corneas of Anti-IL-17 antibody-treated group show that similar to normal cornea, majority of CD11b+ cells have phenotype of resident dendritic cells. However, corneas of isotype-antibody treated group show that the phenotype of majority of CD11b+ cells are similar to the infiltrating pathogenic macrophages/monocytes (FIG. 11).

Example 10

Topical Application of Anti-IL-17 Antibody Prevents Corneal Nerve Degeneration

Figure 12:
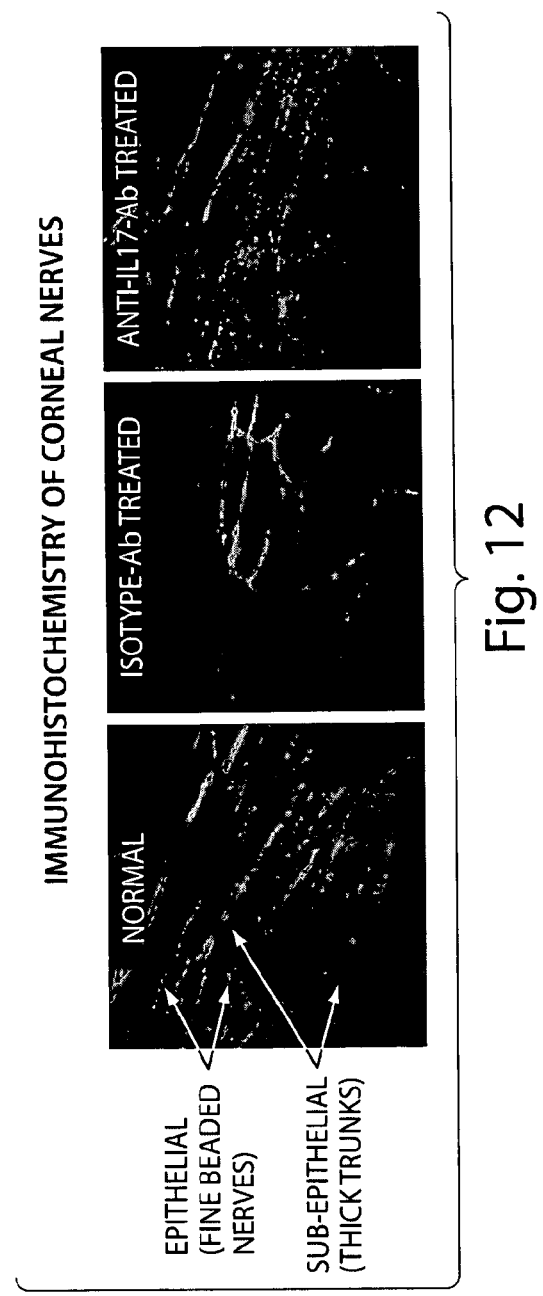
FIG. 12 is a series of micrographs showing that topical application of anti-IL-17 antibody prevents corneal nerve degeneration. Representative micrographs of corneal whole mount showing epithelial and sub-epithelial nerves (Tubulin-III, Red) in different groups. Patterns of nerves in the corneas of Anti-IL17-antibody treated group show similarity to those in the normal corneas, whereas corneas of Isotype-antibody treated group show loss of epithelial nerves.

FIG. 12 shows representative micrographs of corneal whole mount depicting epithelial and sub-epithelial nerves (Tubulin-III, Red) in different groups. Patterns of nerves in the corneas of Anti-IL17-antibody treated group show similarity to those in the normal corneas, whereas corneas of isotype-antibody treated group show loss of epithelial nerves.

Example 11

Figure 14A:
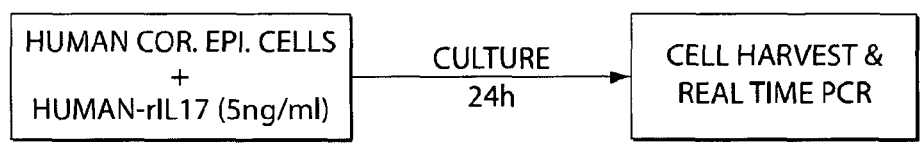
FIG. 14A is a schematic diagram of the experiments performed to generate the data of FIG. 14B.
Figure 14B:
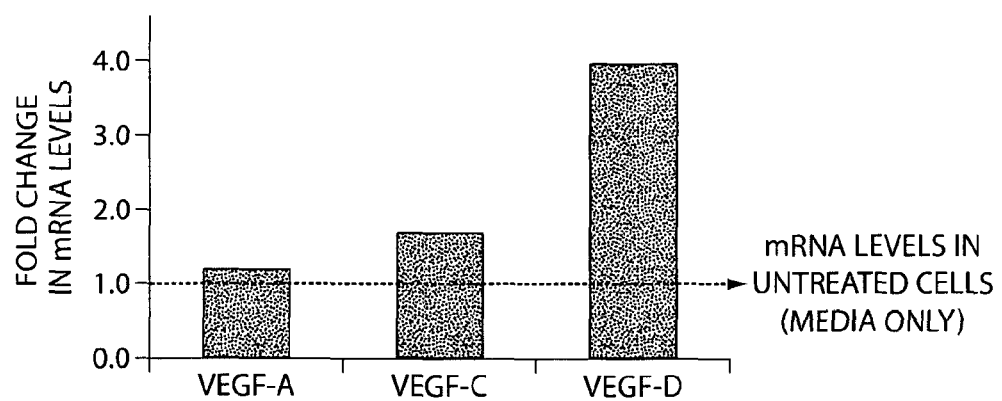
FIG. 14B is a graph of the fold change in mRNA levels of lymphangiogenesis growth factors, such as VEGF-A, VEGF-C, and VEGF-D, in human corneal epithelial cells treated with human-r-IL-17 (5 ng/ml).

Human Corneal Epithelial Cells Respond to IL-17 Cytokine by Increased Secretion of Lymphangiogenesis-Specific Growth Factors To delineate the mechanism(s) of IL-17 mediated lymphangiogenesis in the corneas of dry eye mice (as shown in FIG. 4) and to ensure that IL-17 has similar effects on human cornea, primary human corneal epithelial cells were cultured for 24 h in the presence of IL-17 and the gene expression levels of different VEGF-species were compared to normal untreated cells (FIG. 14A). Real time PCR analyses show that IL-17 treated human corneal epithelial cells express higher levels of lymphangiogenesis-specific growth factors, particularly VEGF-D (4-fold) and VEGF-C (1.8-fold) compared to untreated cells (FIG. 14B).

Example 12

Topical Application of Anti-IL-17 Antibody Enhances Corneal Nerve Regeneration

Anti-IL-17 antibody treatment is applied to the isotype-antibody treated group of Example 10 or non-treated group of mice. Corneas are treated as described above for Example 10. Anti-IL-17 antibody treatment enhances nerve regeneration such that the amount of nerve fibers associated with damaged corneas is increased compared to untreated or isotype-treated corneas.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing the severity of dry eye syndrome comprising
   identifying a subject characterized as suffering from dry eye syndrome;
   topically administering directly to an eye of a subject a composition that inhibits binding of an inflammatory interleukin-17 (IL-17) cytokine to an IL-17 receptor; and
   inhibiting or reducing eye dryness associated with said dry eye syndrome, thereby reducing the severity of said dry eye syndrome, wherein said dry eye syndrome is a non-Sjogren's syndrome associated dry eye syndrome associated with meibomian gland dysfunction, and is not uveitis, intraocular conditions, or inflammation of interior tissues of the eye.

2. The method of claim 1, wherein said identifying step comprises detection of a sign or symptom selected from the group consisting of eye dryness, scratching, stinging, itching, burning, irritation, pain, redness, inflammation, discharge, and excessive watering, and wherein said method inhibits or reduces the severity of at least one of said signs or symptoms.

3. The method of claim 1, wherein said method comprises sequential or simultaneous administration of a composition that inhibits binding of an inflammatory IL-17 cytokine to an IL-17 receptor and a secondary composition.

4. The method of claim 1, wherein the form of said composition is a solid, an ointment, a gel, a liquid, an aerosol, a mist, a polymer, a contact lens, a film, an emulsion, or a suspension.

5. The method of claim 1, wherein said method does not comprise systemic administration or substantial dissemination to non-ocular tissue.

6. The method of claim 1, wherein said composition further comprises a compound selected from the group consisting of a physiologically acceptable salt, poloxamer analogs with carbopol, carbopol/HPMC, carbopol-methyl cellulose, a mucolytic agent, carboxymethylcellulose (CMC), hyaluronic acid, cyclodextrin, and petroleum.

7. The method of claim 1, wherein said method comprises administration of both a composition that inhibits binding of an inflammatory IL-17 cytokine to an IL-17 receptor and a second composition comprising one or more inflammatory antagonist(s).

8. The method of claim 1, wherein said composition comprises:
   (a) a monoclonal or polyclonal antibody;
   (b) an antibody that targets an intracellular or extracellular IL-17 cytokine or IL-17 receptor;
   (c) an antibody that binds to at least one intracellular or extracellular sequence of an IL-17 cytokine or IL-17 receptor;

(d) a single-chain antibody;
(e) a humanized, recombinant, or chimeric antibody;
(f) an antibody conjugated directly or indirectly to a compound that inhibits or modifies the activity of an IL-17 cytokine or an IL-17 receptor or
(g) a composition that inhibits or modifies the transcription, transcript stability, translation, modification, localization, secretion, or function of a polynucleotide or polypeptide encoding an inflammatory interleukin-17 cytokine or an IL-17 receptor.

9. The method of claim 1, wherein said composition inhibits an activity of an inflammatory cytokine selected from the group consisting of IL-17A, IL-17B, IL-17C, IL-17D, IL-17E, and IL-17F.

10. The method of claim 1, wherein said composition inhibits an activity of an inflammatory cytokine receptor selected from the group consisting of IL-17RA, IL-17RB, IL-17RC, IL-17RD, IL-17RE, and IL-17RF.

* * * * *

SEQUENCE LISTING

<160> NUMBER OF SEQ ID NOS: 35

<210> SEQ ID NO 1
<211> LENGTH: 1859
<212> TYPE: DNA

<213> ORGANISM: Homo sapiens

<400> SEQUENCE: 1

```
gcaggcacaa actcatccat ccccagttga ttggaagaaa caacgatgac tcctgggaag      60
acctcattgg tgtcactgct actgctgctg agcctggagg ccatagtgaa ggcaggaatc     120
acaatcccac gaaatccagg atgcccaaat tctgaggaca agaacttccc ccggactgtg     180
atggtcaacc tgaacatcca taaccggaat accaatacca atcccaaaag gtcctcagat     240
tactacaacc gatccacctc accttggaat ctccaccgca atgaggaccc tgagagatat     300
ccctctgtga tctgggaggc aaagtgccgc cacttgggct gcatcaacgc tgatgggaac     360
gtggactacc acatgaactc tgtccccatc cagcaagaga tcctggtcct gcgcagggag     420
cctccacact gccccaactc cttccggctg gagaagatac tggtgtccgt gggctgcacc     480
tgtgtcaccc cgattgtcca ccatgtggcc taagagctct ggggagccca cactccccaa     540
agcagttaga ctatggagag ccgacccagc ccctcaggaa ccctcatcct tcaaagacag     600
cctcatttcg gactaaactc attagagttc ttaaggcagt ttgtccaatt aaagcttcag     660
aggtaacact tggccaagat atgagatctg aattacctttt ccctctttcc aagaaggaag   720
gtttgactga gtaccaattt gcttcttgtt tacttttta agggctttaa gttatttatg     780
tatttaatat gccctgagat aactttgggg tataagattc cattttaatg aattacctac     840
tttatttttgt ttgtcttttt aaagaagata agattctggg cttgggaatt ttattattta    900
aaaggtaaaa cctgtattta tttgagctat ttaaggatct atttatgttt aagtatttag     960
aaaaaggtga aaagcacta ttatcagttc tgcctaggta aatgtaagat agaattaaat     1020
ggcagtgcaa aatttctgag tctttacaac atacggatat agtatttcct cctctttgtt   1080
tttaaaagtt ataacatggc tgaaaagaaa gattaaacct actttcatat gtattaattt   1140
aaattttgca atttgttgag gttttacaag agatacagca agtctaactc tctgttccat   1200
taaacccta taataaaatc cttctgtaat aataaagttt caaaagaaaa tgtttatttg   1260
ttctcattaa atgtattta gcaaactcag ctcttcccta ttgggaagag ttatgcaaat   1320
tctcctataa gcaaaacaaa gcatgtcttt gagtaacaat gacctggaaa tacccaaaat   1380
tccaagttct cgatttcaca tgccttcaag actgaacacc gactaaggtt ttcatactat   1440
tagccaatgc tgtagacaga agcatttttga taggaataga gcaaataaga taatggccct   1500
gaggaatggc atgtcattat taaagatcat atggggaaaa tgaaaccctc cccaaaatac   1560
aagaagttct gggaggagac attgtcttca gactacaatg tccagtttct cccctagact   1620
caggcttcct ttggagatta aggcccctca gagatcaaca gaccaacatt tttctcttcc   1680
tcaagcaaca ctcctagggc ctggcttctg tctgatcaag gcaccacaca acccagaaag   1740
gagctgatgg ggcagaacga actttaagta tgagaaaagt tcagcccaag taaaataaaa   1800
actcaatcac attcaattcc agagtagttt caagtttcac atcgtaacca ttttcgccc    1859
```

<210> SEQ ID NO 2
<211> LENGTH: 155
<212> TYPE: PRT
<213> ORGANISM: Homo sapiens

<400> SEQUENCE: 2

```
Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30
```

```
Cys Pro Asn Ser Glu Asp Lys Asn Phe Pro Arg Thr Val Met Val Asn
        35                  40                  45
Leu Asn Ile His Asn Arg Asn Thr Asn Thr Asn Pro Lys Arg Ser Ser
 50                  55                  60
Asp Tyr Tyr Asn Arg Ser Thr Ser Pro Trp Asn Leu His Arg Asn Glu
 65                  70                  75                  80
Asp Pro Glu Arg Tyr Pro Ser Val Ile Trp Glu Ala Lys Cys Arg His
                 85                  90                  95
Leu Gly Cys Ile Asn Ala Asp Gly Asn Val Asp Tyr His Met Asn Ser
            100                 105                 110
Val Pro Ile Gln Gln Glu Ile Leu Val Leu Arg Arg Glu Pro Pro His
            115                 120                 125
Cys Pro Asn Ser Phe Arg Leu Glu Lys Ile Leu Val Ser Val Gly Cys
        130                 135                 140
Thr Cys Val Thr Pro Ile Val His His Val Ala
145                 150                 155
```

<210> SEQ ID NO 3
<211> LENGTH: 711
<212> TYPE: DNA
<213> ORGANISM: Homo sapiens

<400> SEQUENCE: 3

```
tggggttcca ggcgggcagc agctgcaggc tgaccttgca gcttggcgga atggactggc      60
ctcacaacct gctgtttctt cttaccattt ccatcttcct ggggctgggc cagcccagga    120
gccccaaaag caagaggaag ggcaagggc ggcctgggcc cctggcccct ggccctcacc     180
aggtgccact ggacctggtg tcacggatga aaccgtatgc ccgcatggag gagtatgaga    240
ggaacatcga ggagatggtg gcccagctga ggaacagctc agagctggcc cagagaaagt    300
gtgaggtcaa cttgcagctg tggatgtcca caagaggag cctgtctccc tggggctaca    360
gcatcaacca cgaccccagc cgtatccccg tggacctgcc ggaggcacgg tgcctgtgtc    420
tgggctgtgt gaaccccttc accatgcagg aggaccgcag catggtgagc gtgccggtgt    480
tcagccaggt tcctgtgcgc cgccgcctct gcccgccacc gccccgcaca gggccttgcc    540
gccagcgcgc agtcatggag accatcgctg tgggctgcac ctgcatcttc tgaatcacct    600
ggcccagaag ccaggccagc agcccgagac catcctcctt gcacctttgt gccaagaaag    660
gcctatgaaa agtaaacact gacttttgaa agcaaaaaaa aaaaaaaaa a              711
```

<210> SEQ ID NO 4
<211> LENGTH: 180
<212> TYPE: PRT
<213> ORGANISM: Homo sapiens

<400> SEQUENCE: 4

```
Met Asp Trp Pro His Asn Leu Leu Phe Leu Leu Thr Ile Ser Ile Phe
 1               5                  10                  15
Leu Gly Leu Gly Gln Pro Arg Ser Pro Lys Ser Lys Arg Lys Gly Gln
             20                  25                  30
Gly Arg Pro Gly Pro Leu Ala Pro Gly Pro His Gln Val Pro Leu Asp
         35                  40                  45
Leu Val Ser Arg Met Lys Pro Tyr Ala Arg Met Glu Glu Tyr Glu Arg
 50                  55                  60
Asn Ile Glu Glu Met Val Ala Gln Leu Arg Asn Ser Ser Glu Leu Ala
 65                  70                  75                  80
```

```
Gln Arg Lys Cys Glu Val Asn Leu Gln Leu Trp Met Ser Asn Lys Arg
            85                  90                  95

Ser Leu Ser Pro Trp Gly Tyr Ser Ile Asn His Asp Pro Ser Arg Ile
            100                 105                 110

Pro Val Asp Leu Pro Glu Ala Arg Cys Leu Cys Leu Gly Cys Val Asn
        115                 120                 125

Pro Phe Thr Met Gln Glu Asp Arg Ser Met Val Ser Val Pro Val Phe
    130                 135                 140

Ser Gln Val Pro Val Arg Arg Leu Cys Pro Pro Pro Arg Thr
145                 150                 155                 160

Gly Pro Cys Arg Gln Arg Ala Val Met Glu Thr Ile Ala Val Gly Cys
            165                 170                 175

Thr Cys Ile Phe
            180

<210> SEQ ID NO 5
<211> LENGTH: 1048
<212> TYPE: DNA
<213> ORGANISM: Homo sapiens

<400> SEQUENCE: 5
gccaggtgtg caggccgctc aagcccagc ctgccccgct gccgccacca tgacgctcct      60
ccccggcctc ctgtttctga cctggctgca cacatgcctg gccccaccatg accctcccct   120
caggggcac ccccacagtc acggtacccc acactgctac tcggctgagg aactgcccct    180
cggccaggcc cccccacacc tgctggctcg aggtgccaag tggggcagg ctttgcctgt    240
agccctggtg tccagcctgg aggcagcaag ccacagggg aggcacgaga ggccctcagc    300
tacgacccag tgcccggtgc tgcggccgga ggaggtgttg gaggcagaca cccaccagcg    360
ctccatctca ccctggagat accgtgtgga cacggatgag accgctatc cacagaagct    420
ggccttcgcc gagtgcctgt gcagaggctg tatcgatgca cggacgggcc gcgagacagc    480
tgcgctcaac tccgtgcggc tgctccagag cctgctggtg ctgcgccgcc ggccctgctc    540
ccgcgacggc tcgggctcc ccacacctgg ggcctttgcc ttccacaccg agttcatcca    600
cgtcccgtc ggctgcacct gcgtgctgcc ccgttcagtg tgaccgccga ggccgtgggg    660
cccctagact ggacacgtgt gctccccaga gggcacccccc tatttatgtg tatttattgt   720
tatttatatg cctcccccaa cactacccctt ggggtctggg cattcccgt gtctggagga    780
cagcccccca ctgttctcct catctccagc ctcagtagtt gggggtagaa ggagctcagc    840
acctcttcca gcccttaaag ctgcagaaaa ggtgtcacac ggctgcctgt accttggctc    900
cctgtcctgc tccggcttc ccttacccta tcactggcct caggcccccg caggctgcct    960
cttcccaacc tccttggaag taccctgtt tcttaaacaa ttatttaagt gtacgtgtat   1020
tattaaactg atgaacacat ccccaaaa                                       1048

<210> SEQ ID NO 6
<211> LENGTH: 197
<212> TYPE: PRT
<213> ORGANISM: Homo sapiens

<400> SEQUENCE: 6

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30
```

```
Thr Pro His Cys Tyr Ser Ala Glu Glu Leu Pro Leu Gly Gln Ala Pro
             35                  40                  45

Pro His Leu Leu Ala Arg Gly Ala Lys Trp Gly Gln Ala Leu Pro Val
 50                  55                  60

Ala Leu Val Ser Ser Leu Glu Ala Ser His Arg Gly Arg His Glu
 65                  70                  75                  80

Arg Pro Ser Ala Thr Thr Gln Cys Pro Val Leu Arg Pro Glu Val
                 85                  90                  95

Leu Glu Ala Asp Thr His Gln Arg Ser Ile Ser Pro Trp Arg Tyr Arg
                100                 105                 110

Val Asp Thr Asp Glu Asp Arg Tyr Pro Gln Lys Leu Ala Phe Ala Glu
                115                 120                 125

Cys Leu Cys Arg Gly Cys Ile Asp Ala Arg Thr Gly Arg Glu Thr Ala
130                 135                 140

Ala Leu Asn Ser Val Arg Leu Leu Gln Ser Leu Val Leu Arg Arg
145                 150                 155                 160

Arg Pro Cys Ser Arg Asp Gly Ser Gly Leu Pro Thr Pro Gly Ala Phe
                165                 170                 175

Ala Phe His Thr Glu Phe Ile His Val Pro Val Gly Cys Thr Cys Val
                180                 185                 190

Leu Pro Arg Ser Val
        195
```

<210> SEQ ID NO 7
<211> LENGTH: 1873
<212> TYPE: DNA
<213> ORGANISM: Homo sapiens

<400> SEQUENCE: 7

```
aaaatgttttt cagctcctgg aggcgaaagg tgcagagtcg ctctgtgtcc gtgaggccgg     60
gcggcgacct cgctcagtcg gcttctcggt ccgagtcccc gggtctggat gctggtagcc    120
ggcttcctgc tggcgctgcc gccgagctgg gccgcgggcg ccccgagggc gggcaggcgc    180
cccgcgcggc cgcggggctg cgcggaccgg ccggaggagc tactggagca gctgtacggg    240
cgcctggcgg ccggcgtgct cagtgccttc accacacgc tgcagctggg gccgcgtgag    300
caggcgcgca acgcgagctg cccggcaggg ggcaggcccg ccgaccgccg cttccggccg    360
cccaccaacc tgcgcagcgt gtcgccctgg gcctacagaa tctcctacga cccggcgagg    420
taccccaggt acctgcctga agcctactgc ctgtgccggg gctgcctgac cgggctgttc    480
ggcgaggagg acgtgcgctt ccgcagcgcc cctgtctaca tgcccaccgt cgtcctgcgc    540
cgcaccccg cctgcgccgg cggccgttcc gtctacaccg aggcctacgt caccatcccc    600
gtgggctgca cctgcgtccc cgagccggag aaggacgcag acagcatcaa ctccagcatc    660
gacaaacagg gcgccaagct cctgctgggc ccaacgacg cgcccgctgg ccctgaggc    720
cggtcctgcc ccgggaggtc tccccggccc gcatcccgag gcgcccaagc tggagccgcc    780
tggagggctc ggtcggcgac ctctgaagag agtgcaccga gcaaaccaag tgccggagca    840
ccagcgccgc ctttccatgg agactcgtaa gcagcttcat ctgacacggg catccctggc    900
ttgcttttag ctacaagcaa gcagcgtggc tggaagctga tgggaaacga cccggcacgg    960
gcatcctgtg tgcggccccc atggagggtt tggaaaagtt cacggaggct ccctgaggag   1020
cctctcagat cggctgctgc gggtgcaggg cgtgactcac cgctgggtgc ttgccaaga   1080
gatagggacg catatgcttt ttaaagcaat ctaaaaataa taataagtat agcgactata   1140
```

```
tacctacttt taaaatcaac tgttttgaat agaggcagag ctattttata ttatcaaatg    1200
agagctactc tgttacattt cttaacatat aaacatcgtt ttttacttct tctggtagaa    1260
ttttttaaag cataattgga atccttggat aaattttgta gctggtacac tctggcctgg    1320
gtctctgaat tcagcctgtc accgatggct gactgatgaa atggacacgt ctcatctgac    1380
ccactcttcc ttccactgaa ggtcttcacg ggcctccagg tggaccaaag ggatgcacag    1440
gcggctcgca tgcccaggg ccagctaaga gttccaaaga tctcagattt ggttttagtc      1500
atgaatacat aaacagtctc aaactcgcac aattttttcc cccttttgaa agccactggg    1560
gccaatttgt ggttaagagg tggtgagata agaagtggaa cgtgacatct ttgccagttg    1620
tcagaagaat ccaagcaggt attggcttag ttgtaagggc tttaggatca ggctgaatat    1680
gaggacaaag tgggccacgt tagcatctgc agagatcaat ctggaggctt ctgtttctgc    1740
attctgccac gagagctagg tccttgatct tttctttaga ttgaaagtct gtctctgaac    1800
acaattattt gtaaaagtta gtagttcttt tttaaatcat taaaagaggc ttgctgaagg    1860
aaaaaaaaaa aaa                                                        1873
```

<210> SEQ ID NO 8
<211> LENGTH: 202
<212> TYPE: PRT
<213> ORGANISM: Homo sapiens

<400> SEQUENCE: 8

```
Met Leu Val Ala Gly Phe Leu Leu Ala Leu Pro Pro Ser Trp Ala Ala
1               5                   10                  15

Gly Ala Pro Arg Ala Gly Arg Arg Pro Ala Arg Pro Arg Gly Cys Ala
                20                  25                  30

Asp Arg Pro Glu Glu Leu Leu Glu Gln Leu Tyr Gly Arg Leu Ala Ala
            35                  40                  45

Gly Val Leu Ser Ala Phe His His Thr Leu Gln Leu Gly Pro Arg Glu
        50                  55                  60

Gln Ala Arg Asn Ala Ser Cys Pro Ala Gly Gly Arg Pro Ala Asp Arg
65                  70                  75                  80

Arg Phe Arg Pro Pro Thr Asn Leu Arg Ser Val Ser Pro Trp Ala Tyr
                85                  90                  95

Arg Ile Ser Tyr Asp Pro Ala Arg Tyr Pro Arg Tyr Leu Pro Glu Ala
                100                 105                 110

Tyr Cys Leu Cys Arg Gly Cys Leu Thr Gly Leu Phe Gly Glu Glu Asp
            115                 120                 125

Val Arg Phe Arg Ser Ala Pro Val Tyr Met Pro Thr Val Val Leu Arg
        130                 135                 140

Arg Thr Pro Ala Cys Ala Gly Gly Arg Ser Val Tyr Thr Glu Ala Tyr
145                 150                 155                 160

Val Thr Ile Pro Val Gly Cys Thr Cys Val Pro Glu Pro Glu Lys Asp
                165                 170                 175

Ala Asp Ser Ile Asn Ser Ser Ile Asp Lys Gln Gly Ala Lys Leu Leu
                180                 185                 190

Leu Gly Pro Asn Asp Ala Pro Ala Gly Pro
            195                 200
```

<210> SEQ ID NO 9
<211> LENGTH: 1335
<212> TYPE: DNA
<213> ORGANISM: Homo sapiens

<400> SEQUENCE: 9

```
ggcttgctga aaataaaatc aggactccta acctgctcca gtcagcctgc ttccacgagg      60
cctgtcagtc agtgcccgac ttgtgactga gtgtgcagtg cccagcatgt accaggtcag     120
tgcagagggc tgcctgaggg ctgtgctgag agggagagga gcagagatgc tgctgagggt     180
ggagggaggc caagctgcca ggtttggggc tggggccaa gtggagtgag aaactgggat      240
cccagggga gggtgcagat gagggagcga cccagattag gtgaggacag ttctctcatt      300
agccttttcc tacaggtggt tgcattcttg caatggtca tgggaaccca cacctacagc      360
cactggccca gctgctgccc cagcaaaggg caggacacct ctgaggagct gctgaggtgg     420
agcactgtgc ctgtgcctcc cctagagcct gctaggccca accgccaccc agagtcctgt     480
agggccagtg aagatggacc cctcaacagc agggccatct cccctggag atatgagttg      540
gacagagact tgaaccggct ccccaggac ctgtaccacg cccgttgcct gtgcccgcac      600
tgcgtcagcc tacagacagg ctcccacatg accccgggg caactcgga gctgctctac       660
cacaaccaga ctgtcttcta caggcggcca tgccatggcg agaagggcac ccacaagggc     720
tactgcctgg agcgcaggct gtaccgtgtt tccttagctt gtgtgtgtgt gcggccccgt     780
gtgatgggct agccggacct gctggaggct ggtcccttt tgggaaacct ggagccaggt      840
gtacaaccac ttgccatgaa gggccaggat gcccagatgc ttggcccctg tgaagtgctg     900
tctggagcag caggatcccg ggacaggatg ggggctttg gggaaaacct gcacttctgc      960
acattttgaa aagagcagct gctgcttagg gccgccggaa gctggtgtcc tgtcattttc    1020
tctcaggaaa ggttttcaaa gttctgccca tttctggagg ccaccactcc tgtctcttcc    1080
tcttttccca tccctgcta ccctggccca gcacaggcac tttctagata tttccccctt     1140
gctggagaag aaagagcccc tggttttatt tgtttgttta ctcatcactc agtgagcatc    1200
tactttgggt gcattctagt gtagttacta gtcttttgac atggatgatt ctgaggagga    1260
agctgttatt gaatgtatag agatttatcc aaataaatat ctttatttaa aaatgaaaaa    1320
aaaaaaaaaa aaaaa                                                    1335
```

<210> SEQ ID NO 10
<211> LENGTH: 177
<212> TYPE: PRT
<213> ORGANISM: Homo sapiens

<400> SEQUENCE: 10

```
Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
```

```
            115                 120                 125
Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly

<210> SEQ ID NO 11
<211> LENGTH: 808
<212> TYPE: DNA
<213> ORGANISM: Homo sapiens

<400> SEQUENCE: 11
gaacacaggc atacacagga agatacattc acagaaagag cttcctgcac aaagtaagcc      60
accagcgcaa catgacagtg aagaccctgc atggcccagc catggtcaag tacttgctgc     120
tgtcgatatt ggggcttgcc tttctgagtg aggcggcagc tcggaaaatc cccaaagtag     180
gacatacttt tttccaaaag cctgagagtt gcccgcctgt gccaggaggt agtatgaagc     240
ttgacattgg catcatcaat gaaaaccagc gcgtttccat gtcacgtaac atcgagagcc     300
gctccacctc ccctggaat tacactgtca cttgggaccc caaccggtac ccctcggaag     360
ttgtacaggc ccagtgtagg aacttgggct gcatcaatgc tcaaggaaag gaagacatct     420
ccatgaattc cgttcccatc agcaagagaa ccctggtcgt ccggaggaag caccaaggct     480
gctctgtttc tttccagttg gagaaggtgc tggtgactgt tggctgcacc tgcgtcaccc     540
ctgtcatcca ccatgtgcag taagaggtgc atatccactc agctgaagaa gctgtagaaa     600
tgccactcct tacccagtgc tctgcaacaa gtcctgtctg accccaatt ccctccactt      660
cacaggactc ttaataagac ctgcacggat ggaaacagaa atattcaca atgtatgtgt      720
gtatgtacta cactttatat ttgatatcta aaatgttagg agaaaatta atatattcag      780
tgctaatata ataaagtatt aataattt                                        808

<210> SEQ ID NO 12
<211> LENGTH: 163
<212> TYPE: PRT
<213> ORGANISM: Homo sapiens

<400> SEQUENCE: 12

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
                20                  25                  30

Ile Pro Lys Val Gly His Thr Phe Phe Gln Lys Pro Glu Ser Cys Pro
                35                  40                  45

Pro Val Pro Gly Gly Ser Met Lys Leu Asp Ile Gly Ile Ile Asn Glu
            50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
                100                 105                 110

Lys Glu Asp Ile Ser Met Asn Ser Val Pro Ile Gln Gln Glu Thr Leu
```

115                 120                 125
Val Val Arg Arg Lys His Gln Gly Cys Ser Val Ser Phe Gln Leu Glu
        130                 135                 140

Lys Val Leu Val Thr Val Gly Cys Thr Cys Val Thr Pro Val Ile His
145                 150                 155                 160

His Val Gln

<210> SEQ ID NO 13
<211> LENGTH: 3429
<212> TYPE: DNA
<213> ORGANISM: Homo sapiens

<400> SEQUENCE: 13

| | | | | | | |
|---|---|---|---|---|---|---|
| ctgggcccgg | gctggaagcc | ggaagcgagc | aaagtggagc | cgactcgaac | tccaccgcgg | 60 |
| aaaagaaagc | tcagaacgt | tcgttcgctg | cgtccccagc | cggggccgag | ccctccgcga | 120 |
| cgccagccgg | gccatggggg | ccgcacgcag | cccgccgtcc | gctgtcccgg | ggcccctgct | 180 |
| ggggctgctc | ctgctgctcc | tgggcgtgct | ggccccgggt | ggcgcctccc | tgcgactcct | 240 |
| ggaccaccgg | gcgctggtct | gctcccagcc | ggggctaaac | tgcacggtca | agaatagtac | 300 |
| ctgcctggat | gacagctgga | ttcaccctcg | aaacctgacc | ccctcctccc | caaggacct | 360 |
| gcagatccag | ctgcactttg | cccacaccca | acaaggagac | ctgttccccg | tggctcacat | 420 |
| cgaatggaca | ctgcagacag | cgccagcat | cctgtacctc | gagggtgcag | agttatctgt | 480 |
| cctgcagctg | aacaccaatg | aacgtttgtg | cgtcaggttt | gagtttctgt | ccaaactgag | 540 |
| gcatcaccac | aggcggtggc | gttttacctt | cagccacttt | gtggttgacc | ctgaccagga | 600 |
| atatgaggtg | accgttcacc | acctgcccaa | gccatccct | gatgggacc | caaaccacca | 660 |
| gtccaagaat | tccttgtgc | ctgactgtga | gcacgccagg | atgaaggtaa | ccacgccatg | 720 |
| catgagctca | ggcagcctgt | gggaccccaa | catcaccgtg | gagaccctgg | aggcccacca | 780 |
| gctgcgtgtg | agcttcaccc | tgtggaacga | atctacccat | taccagatcc | tgctgaccag | 840 |
| ttttccgcac | atggagaacc | acagttgctt | tgagcacatg | caccacatac | ctgcgcccag | 900 |
| accagaagag | ttccaccagc | gatccaacgt | cacactcact | ctacgcaacc | ttaaagggtg | 960 |
| ctgtcgccac | caagtgcaga | tccagcccct | cttcagcagc | tgcctcaatg | actgcctcag | 1020 |
| acactccgcg | actgtttcct | gcccagaaat | gccagacact | ccagaaccaa | ttccggacta | 1080 |
| catgcccctg | tgggtgtact | ggttcatcac | gggcatctcc | atcctgctgg | tgggctccgt | 1140 |
| catcctgctc | atcgtctgca | tgaccctgga | gctagctggg | cctggaagtg | aaaaatacag | 1200 |
| tgatgacacc | aaatacaccg | atggcctgcc | tgcggctgac | ctgatccccc | caccgctgaa | 1260 |
| gcccaggaag | gtctggatca | tctactcagc | cgaccacccc | ctctacgtgg | acgtggtcct | 1320 |
| gaaattcgcc | cagttcctgc | tcaccgcctg | cggcacggaa | gtggccctgg | acctgctgga | 1380 |
| agagcaggcc | atctcggagg | caggagtcat | gacctgggtg | ggccgtcaga | agcaggagat | 1440 |
| ggtggagagc | aactctaaga | tcatcgtcct | gtgctcccgc | ggcacgcgcg | ccaagtggca | 1500 |
| ggcgctcctg | ggccgggggg | cgcctgtgcg | gctgcgctgc | gaccacggaa | agcccgtggg | 1560 |
| ggacctgttc | actgcagcca | tgaacatgat | cctccccgga | cttcaagagc | cagcctgctt | 1620 |
| cggcacctac | gtagtctgct | acttcagcga | ggtcagctgt | gacggcgacg | tccccgacct | 1680 |
| gttcggcgcg | cgccgcgcgg | taccgctcat | ggacaggttc | gaggaggtgt | acttccgcat | 1740 |
| ccaggacctg | gagatgttcc | agccgggccg | catgcaccgc | gtaggggagc | tgtcggggga | 1800 |
| caactacctg | cggagcccgg | gcggcaggca | gctccgcgcc | gccctggaca | ggttccggga | 1860 |

```
ctggcaggtc cgctgtcccg actggttcga atgtgagaac ctctactcag cagatgacca    1920
ggatgccccg tccctggacg aagaggtgtt tgaggagcca ctgctgcctc cgggaaccgg    1980
catcgtgaag cgggcgcccc tggtgcgcga gcctggctcc caggcctgcc tggccataga    2040
cccgctggtc ggggaggaag gaggagcagc agtggcaaag ctggaacctc acctgcagcc    2100
ccggggtcag ccagcgccgc agcccctcca caccctggtg ctcgccgcag aggaggggc     2160 cctggtggcc gcgtggagc ctgggcccct ggctgacggt gccgcagtcc ggctggcact    2220 ggcggggag ggcgaggcct gcccgctgct gggcagcccg ggcgctgggc gaaatagcgt    2280
cctcttcctc cccgtggacc ccgaggactc gccccttggc agcagcaccc ccatggcgtc    2340
tcctgacctc cttccagagg acgtgaggga gcacctcgaa ggcttgatgc tctcgctctt    2400
cgagcagagt ctgagctgcc aggcccaggg gggctgcagt agacccgcca tggtcctcac    2460
agacccacac acgccctacg aggaggagca gcggcagtca gtgcagtctg accagggcta    2520
catctccagg agctccccgc agccccccga gggactcacg gaaatggagg aagaggagga    2580
agaggagcag gacccaggga gccggcccct gccactctct cccgaggacc tggagagcct    2640
gaggagcctc cagcggcagc tgcttttccg ccagctgcag aagaactcgg gctgggacac    2700
gatggggtca gagtcagagg ggcccagtgc atgagggcgg ctccccaggg accgcccaga    2760
tcccagcttt gagagaggag tgtgtgtgca cgtattcatc tgtgtgtaca tgtctgcatg    2820
tgtatatgtt cgtgtgtgaa atgtaggctt taaaatgtaa atgtctggat tttaatccca    2880
ggcatccctc ctaacttttc tttgtgcagc ggtctggtta tcgtctatcc ccaggggaat    2940
ccacacagcc cgctcccagg agctaatggt agagcgtcct tgaggctcca ttattcgttc    3000
attcagcatt tattgtgcac ctactatgtg gcgggcattt gggataccaa gataaattgc    3060
atgcggcatg gccccagcca tgaaggaact taaccgctag tgccgaggac acgttaaacg    3120
aacaggatgg gccgggcacg gtggctcacg cctgtaatcc cagcacactg ggaggccgag    3180
gcaggtggat cactctgagg tcaggagttt gagccagcct ggccaacatg gtgaaacccc    3240
atctccacta aaatagaaa attagccgg gcatggtgac acatgcctgt agtcctagct    3300
acttgggagg ctgaggcagg agaattgctt gaatctggga ggcagaggtt gcagtgagcc    3360
gagattgtgc cattgcactg cagcctggat gacagagcga gactctatct caaaaaaaaa    3420
aaaaaaaaa                                                            3429
```

<210> SEQ ID NO 14
<211> LENGTH: 866
<212> TYPE: PRT
<213> ORGANISM: Homo sapiens

<400> SEQUENCE: 14

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
```

```
            85                  90                  95
Glu Trp Thr Leu Gln Thr Asp Ala Ser Ile Leu Tyr Leu Glu Gly Ala
            100                 105                 110
Glu Leu Ser Val Leu Gln Leu Asn Thr Asn Glu Arg Leu Cys Val Arg
            115                 120                 125
Phe Glu Phe Leu Ser Lys Leu Arg His His Arg Arg Trp Arg Phe
            130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
            165                 170                 175
Ser Lys Asn Phe Leu Val Pro Asp Cys Glu His Ala Arg Met Lys Val
            180                 185                 190
Thr Thr Pro Cys Met Ser Ser Gly Ser Leu Trp Asp Pro Asn Ile Thr
            195                 200                 205
Val Glu Thr Leu Glu Ala His Gln Leu Arg Val Ser Phe Thr Leu Trp
            210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
            245                 250                 255
Pro Glu Glu Phe His Gln Arg Ser Asn Val Thr Leu Thr Leu Arg Asn
            260                 265                 270
Leu Lys Gly Cys Cys Arg His Gln Val Gln Ile Gln Pro Phe Phe Ser
            275                 280                 285
Ser Cys Leu Asn Asp Cys Leu Arg His Ser Ala Thr Val Ser Cys Pro
            290                 295                 300
Glu Met Pro Asp Thr Pro Glu Pro Ile Pro Asp Tyr Met Pro Leu Trp
305                 310                 315                 320
Val Tyr Trp Phe Ile Thr Gly Ile Ser Ile Leu Leu Val Gly Ser Val
            325                 330                 335
Ile Leu Leu Ile Val Cys Met Thr Trp Arg Leu Ala Gly Pro Gly Ser
            340                 345                 350
Glu Lys Tyr Ser Asp Asp Thr Lys Tyr Thr Asp Gly Leu Pro Ala Ala
            355                 360                 365
Asp Leu Ile Pro Pro Leu Lys Pro Arg Lys Val Trp Ile Ile Tyr
            370                 375                 380
Ser Ala Asp His Pro Leu Tyr Val Asp Val Val Leu Lys Phe Ala Gln
385                 390                 395                 400
Phe Leu Leu Thr Ala Cys Gly Thr Glu Val Ala Leu Asp Leu Leu Glu
            405                 410                 415
Glu Gln Ala Ile Ser Glu Ala Gly Val Met Thr Trp Val Gly Arg Gln
            420                 425                 430
Lys Gln Glu Met Val Glu Ser Asn Ser Lys Ile Ile Val Leu Cys Ser
            435                 440                 445
Arg Gly Thr Arg Ala Lys Trp Gln Ala Leu Leu Gly Arg Gly Ala Pro
            450                 455                 460
Val Arg Leu Arg Cys Asp His Gly Lys Pro Val Gly Asp Leu Phe Thr
465                 470                 475                 480
Ala Ala Met Asn Met Ile Leu Pro Asp Phe Lys Arg Pro Ala Cys Phe
            485                 490                 495
Gly Thr Tyr Val Val Cys Tyr Phe Ser Glu Val Ser Cys Asp Gly Asp
            500                 505                 510
```

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Val Phe Glu Glu
        595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Ala Val Glu Pro Gly Pro Leu Ala Asp
        675                 680                 685

Gly Ala Ala Val Arg Leu Ala Leu Ala Gly Glu Gly Glu Ala Cys Pro
690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
                740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu
                805                 810                 815

Glu Glu Gln Asp Pro Gly Lys Pro Ala Leu Pro Leu Ser Pro Glu Asp
                820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
850                 855                 860

Ser Ala
865

<210> SEQ ID NO 15
<211> LENGTH: 2072
<212> TYPE: DNA
<213> ORGANISM: Homo sapiens

<400> SEQUENCE: 15
agcgtgcggg tggcctggat cccgcgcagt ggcccggcga tgtcgctcgt gctgctaagc    60

```
ctggccgcgc tgtgcaggag cgccgtaccc cgagagccga ccgttcaatg tggctctgaa      120
actgggccat ctccagagtg gatgctacaa catgatctaa tccccggaga cttgagggac      180
ctccgagtag aacctgttac aactagtgtt gcaacagggg actattcaat tttgatgaat      240
gtaagctggg tactccgggc agatgccagc atccgcttgt tgaaggccac caagatttgt      300
gtgacgggca aaagcaactt ccagtcctac agctgtgtga ggtgcaatta cacagaggcc      360
ttccagactc agaccagacc ctctggtggt aaatggacat tttcctacat cggcttccct      420
gtagagctga acacagtcta tttcattggg gcccataata ttcctaatgc aaatatgaat      480
gaagatggcc cttccatgtc tgtgaatttc acctcaccag ctgcctaga ccacataatg       540 aaatataaaa aaagtgtgt caaggccgga agcctgtggg atccgaacat cactgcttgt       600
aagaagaatg aggagacagt agaagtgaac ttcacaacca ctcccctggg aaacagatac      660
atggctctta tccaacacag cactatcatc gggttttctc aggtgtttga gccacaccag      720
aagaaacaaa cgcgagcttc agtggtgatt ccagtgactg gggatagtga aggtgctacg      780
gtgcagctga ctccatattt tcctacttgt ggcagcgact gcatccgaca taaggaaca      840 gttgtgctct gccacaaac aggcgtccct ttccctctgg ataacaacaa agcaagccg       900 ggaggctggc tgcctctcct cctgctgtct ctgctggtgg ccacatgggt gctggtggca      960
gggatctatc taatgtggag gcacgaaagg atcaagaaga cttccttttc taccaccaca      1020
ctactgcccc ccattaaggt tcttgtggtt tacccatctg aaatatgttt ccatcacaca      1080
atttgttact tcactgaatt tcttcaaaac cattgcagaa gtgaggtcat ccttgaaaag      1140
tggcagaaaa agaaaatagc agagatgggt ccagtgcagt ggcttgccac tcaaaagaag      1200
gcagcagaca aagtcgtctt ccttctttcc aatgacgtca acagtgtgtg cgatggtacc      1260
tgtggcaaga gcgagggcag tcccagtgag aactctcaag acctcttccc ccttgccttt      1320
aaccttttct gcagtgatct aagaagccag attcatctgc acaaatacgt ggtggtctac      1380
tttagagaga ttgatacaaa agacgattac aatgctctca gtgtctgccc caagtaccac      1440
ctcatgaagg atgccactgc tttctgtgca gaacttctcc atgtcaagca gcaggtgtca      1500
gcaggaaaaa gatcacaagc ctgccacgat ggctgctgct ccttgtagcc cacccatgag      1560
aagcaagaga ccttaaaggc ttcctatccc accaattaca gggaaaaaac gtgtgatgat      1620
cctgaagctt actatgcagc ctacaaacag ccttagtaat taaacatttt ataccaata       1680 aaattttcaa atattgctaa ctaatgtagc attaactaac gattggaaac tacatttaca      1740
acttcaaagc tgttttatac atagaaatca attacagttt taattgaaaa ctataaccat      1800
tttgataatg caacaataaa gcatcttcag ccaaacatct agtcttccat agaccatgca      1860
ttgcagtgta cccagaactg tttagctaat attctatgtt taattaatga atactaactc      1920 taagaaccc tcactgattc actcaatagc atcttaagtg aaaaaccttc tattacatgc       1980
aaaaaatcat tgttttaag ataacaaaag tagggaataa acaagctgaa cccactttta       2040 aaaaaaaaa aaaaaaaaa aaaaaaaaa aa                                      2072
```

<210> SEQ ID NO 16
<211> LENGTH: 502
<212> TYPE: PRT
<213> ORGANISM: Homo sapiens

<400> SEQUENCE: 16

Met Ser Leu Val Leu Leu Ser Leu Ala Ala Leu Cys Arg Ser Ala Val
1               5                   10                  15

```
Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
                100                 105                 110

Arg Pro Ser Gly Gly Lys Trp Thr Phe Ser Tyr Ile Gly Phe Pro Val
            115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
                195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
                260                 265                 270

Gln Thr Gly Val Pro Phe Pro Leu Asp Asn Asn Lys Ser Lys Pro Gly
            275                 280                 285

Gly Trp Leu Pro Leu Leu Leu Ser Leu Leu Val Ala Thr Trp Val
290                 295                 300

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
                325                 330                 335

Val Tyr Pro Ser Glu Ile Cys Phe His His Thr Ile Cys Tyr Phe Thr
            340                 345                 350

Glu Phe Leu Gln Asn His Cys Arg Ser Glu Val Ile Leu Glu Lys Trp
    355                 360                 365

Gln Lys Lys Lys Ile Ala Glu Met Gly Pro Val Gln Trp Leu Ala Thr
370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
                405                 410                 415

Glu Asn Ser Gln Asp Leu Phe Pro Leu Ala Phe Asn Leu Phe Cys Ser
            420                 425                 430
```

```
Asp Leu Arg Ser Gln Ile His Leu His Lys Tyr Val Val Tyr Phe
        435                 440                 445

Arg Glu Ile Asp Thr Lys Asp Asp Tyr Asn Ala Leu Ser Val Cys Pro
    450                 455                 460

Lys Tyr His Leu Met Lys Asp Ala Thr Ala Phe Cys Ala Glu Leu Leu
465                 470                 475                 480

His Val Lys Gln Gln Val Ser Ala Gly Lys Arg Ser Gln Ala Cys His
            485                 490                 495

Asp Gly Cys Cys Ser Leu
            500

<210> SEQ ID NO 17
<211> LENGTH: 2691
<212> TYPE: DNA
<213> ORGANISM: Homo sapiens

<400> SEQUENCE: 17
aaaacgaaag cactccgtgc tggaagtagg aggagagtca ggactcccag gacagagagt      60
gcacaaacta cccagcacag ccccctccgc cccctctgga ggctgaagag ggattccagc     120
ccctgccacc cacagacacg ggctgactgg ggtgtctgcc cccttggggg ggggcagca     180 cagggcctca ggcctgggtg ccacctggca cctagaagat gcctgtgccc tggttcttgc     240
tgtccttggc actgggccga agcccagtgg tcctttctct ggagaggctt gtggggcctc     300
aggacgctac ccactgctct ccggtgagtc tggaaccctg gggagacgag gaaaggctca     360
gggttcagtt tttggctcag caaagcctta gcctggctcc tgtcactgct gccactgcca     420
gaactgccct gtctggtctg tctggtgctg atggtagaag agaagaacgg ggaaggggca     480
agagctgggt ctgtctttct ctgggagggt ctgggaatac ggagccccag aaaaagggcc     540
tctcctgccg cctctgggac agtgacatac tctgcctgcc tggggacatc gtgcctgctc     600
cgggccccgt gctggcgcct acgcacctgc agacagagct ggtgctgagg tgccagaagg     660
agaccgactg tgacctctgt ctgcgtgtgg ctgtccactt ggccgtgcat gggcactggg     720
aagagcctga agatgaggaa aagtttggag gagcagctga ctcaggggtg gaggagccta     780
ggaatgcctc tctccaggcc caagtcgtgc tctccttcca ggcctaccct actgcccgct     840
gcgtcctgct ggaggtgcaa gtgcctgctg cccttgtgca gtttggtcag tctgtgggct     900
ctgtggtata tgactgcttc gaggctgccc tagggagtga ggtacgaatc tggtcctata     960
ctcagcccag gtacgagaag gaactcaacc acacacagca gctgcctgac tgcaggggga    1020
tcgaagtctg gaacagcatc ccgagctgct gggcctgcc ctggctcaac gtgtcagcag    1080
atggtgacaa cgtgcatctg gttctgaatg tctctgagga gcagcacttc ggcctctccc    1140
tgtactggaa tcaggtccag ggcccccaa aaccccggtg cacaaaaac ctgactggac    1200 cgcagatcat taccttgaac cacacagacc tggttccctg cctctgtatt caggtgtggc    1260
ctctggaacc tgactccgtt aggacgaaca tctgcccctt cagggaggac ccccgcgcac    1320
accagaacct ctggcaagcc gcccgactgc gactgctgac cctgcagagc tggctgctgg    1380
acgcaccgtg ctcgctgccc gcagaagcgg cactgtgctg gcgggctccg ggtggggacc    1440
cctgccagcc actggtccca ccgctttcct gggagaacgt cactgtggac aaggttctcg    1500
agttcccatt gctgaaaggc caccctaacc tctgtgttca ggtgaacagc tcggagaagc    1560
tgcagctgca ggagtgcttg tgggctgact ccctgggggcc tctcaaagac gatgtgctac    1620
tgttggagac acgaggcccc caggacaaca gatccctctg tgccttggaa cccagtggct    1680
```

```
gtacttcact acccagcaaa gcctccacga gggcagctcg ccttggagag tacttactac    1740
aagacctgca gtcaggccag tgtctgcagc tatgggacga tgacttggga gcgctatggg    1800
cctgccccat ggacaaatac atccacaagc gctgggccct cgtgtggctg gcctgcctac    1860
tctttgccgc tgcgctttcc ctcatcctcc ttctcaaaaa ggatcacgcg aaagggtggc    1920
tgaggctctt gaaacaggac gtccgctcgg gggcggccgc cagggccgc gcggctctgc     1980 tcctctactc agccgatgac tcgggtttcg agcgcctggt gggcgccctg cgtcggccc     2040 tgtgccagct gccgctgcgc gtggccgtag acctgtggag ccgtcgtgaa ctgagcgcgc    2100
aggggcccgt ggcttggttt cacgcgcagc ggcgccagac cctgcaggag gcggcgtgg     2160 tggtcttgct cttctctccc ggtgcggtgg cgctgtgcag cgagtggcta caggatgggg    2220
tgtccgggcc cggggcgcac ggccgcacg acgccttccg cgcctcgctc agctgcgtgc     2280
tgcccgactt cttgcagggc cgggcgcccg gcagctacgt gggggcctgc ttcgacaggc    2340
tgctccaccc ggacgccgta cccgcccttt ccgcaccgt gcccgtcttc acactgccct     2400
cccaactgcc agacttcctg ggggccctgc agcagcctcg cgccccgcgt tccgggcggc    2460
tccaagagag agcggagcaa gtgtcccggg cccttcagcc agccctggat agctacttcc    2520
atccccgggg gactcccgcg ccgggacgcg gggtgggacc aggggcggga cctggggcgg    2580
gggacgggac ttaaataaag gcagacgctg ttttctacc catgtggccc aaaaaaaaaa     2640 aaaaaaaaa aaaaaaaaa aaaaaaaaa aaaaaaaaa aaaaaaaaa a                  2691
```

<210> SEQ ID NO 18
<211> LENGTH: 791
<212> TYPE: PRT
<213> ORGANISM: Homo sapiens

<400> SEQUENCE: 18

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Val Ser Leu Glu Pro Trp Gly Asp Glu Glu Arg Leu Arg
        35                  40                  45

Val Gln Phe Leu Ala Gln Gln Ser Leu Ser Leu Ala Pro Val Thr Ala
    50                  55                  60

Ala Thr Ala Arg Thr Ala Leu Ser Gly Leu Ser Gly Ala Asp Gly Arg
65                  70                  75                  80

Arg Glu Glu Arg Gly Arg Gly Lys Ser Trp Val Cys Leu Ser Leu Gly
                85                  90                  95

Gly Ser Gly Asn Thr Glu Pro Gln Lys Lys Gly Leu Ser Cys Arg Leu
            100                 105                 110

Trp Asp Ser Asp Ile Leu Cys Leu Pro Gly Asp Ile Val Pro Ala Pro
        115                 120                 125

Gly Pro Val Leu Ala Pro Thr His Leu Gln Thr Glu Leu Val Leu Arg
    130                 135                 140

Cys Gln Lys Glu Thr Asp Cys Asp Leu Cys Leu Arg Val Ala Val His
145                 150                 155                 160

Leu Ala Val His Gly His Trp Glu Glu Pro Glu Asp Glu Glu Lys Phe
                165                 170                 175

Gly Gly Ala Ala Asp Ser Gly Val Glu Glu Pro Arg Asn Ala Ser Leu
            180                 185                 190

Gln Ala Gln Val Val Leu Ser Phe Gln Ala Tyr Pro Thr Ala Arg Cys
```

```
            195                 200                 205
Val Leu Leu Glu Val Gln Val Pro Ala Ala Leu Val Gln Phe Gly Gln
210                 215                 220

Ser Val Gly Ser Val Val Tyr Asp Cys Phe Glu Ala Ala Leu Gly Ser
225                 230                 235                 240

Glu Val Arg Ile Trp Ser Tyr Thr Gln Pro Arg Tyr Glu Lys Glu Leu
                    245                 250                 255

Asn His Thr Gln Gln Leu Pro Asp Cys Arg Gly Leu Glu Val Trp Asn
                260                 265                 270

Ser Ile Pro Ser Cys Trp Ala Leu Pro Trp Leu Asn Val Ser Ala Asp
            275                 280                 285

Gly Asp Asn Val His Leu Val Leu Asn Val Ser Glu Glu Gln His Phe
290                 295                 300

Gly Leu Ser Leu Tyr Trp Asn Gln Val Gln Gly Pro Pro Lys Pro Arg
305                 310                 315                 320

Trp His Lys Asn Leu Thr Gly Pro Gln Ile Ile Thr Leu Asn His Thr
                    325                 330                 335

Asp Leu Val Pro Cys Leu Cys Ile Gln Val Trp Pro Leu Glu Pro Asp
                340                 345                 350

Ser Val Arg Thr Asn Ile Cys Pro Phe Arg Glu Asp Pro Arg Ala His
            355                 360                 365

Gln Asn Leu Trp Gln Ala Ala Arg Leu Arg Leu Thr Leu Gln Ser
370                 375                 380

Trp Leu Leu Asp Ala Pro Cys Ser Leu Pro Ala Glu Ala Ala Leu Cys
385                 390                 395                 400

Trp Arg Ala Pro Gly Gly Asp Pro Cys Gln Pro Leu Val Pro Pro Leu
                    405                 410                 415

Ser Trp Glu Asn Val Thr Val Asp Lys Val Leu Glu Phe Pro Leu Leu
                420                 425                 430

Lys Gly His Pro Asn Leu Cys Val Gln Val Asn Ser Ser Glu Lys Leu
            435                 440                 445

Gln Leu Gln Glu Cys Leu Trp Ala Asp Ser Leu Gly Pro Leu Lys Asp
450                 455                 460

Asp Val Leu Leu Leu Glu Thr Arg Gly Pro Gln Asp Asn Arg Ser Leu
465                 470                 475                 480

Cys Ala Leu Glu Pro Ser Gly Cys Thr Ser Leu Pro Ser Lys Ala Ser
                    485                 490                 495

Thr Arg Ala Ala Arg Leu Gly Glu Tyr Leu Leu Gln Asp Leu Gln Ser
                500                 505                 510

Gly Gln Cys Leu Gln Leu Trp Asp Asp Leu Gly Ala Leu Trp Ala
            515                 520                 525

Cys Pro Met Asp Lys Tyr Ile His Lys Arg Trp Ala Leu Val Trp Leu
530                 535                 540

Ala Cys Leu Leu Phe Ala Ala Ala Leu Ser Leu Ile Leu Leu Leu Lys
545                 550                 555                 560

Lys Asp His Ala Lys Gly Trp Leu Arg Leu Leu Lys Gln Asp Val Arg
                    565                 570                 575

Ser Gly Ala Ala Ala Arg Gly Arg Ala Ala Leu Leu Tyr Ser Ala
                580                 585                 590

Asp Asp Ser Gly Phe Glu Arg Leu Val Gly Ala Leu Ala Ser Ala Leu
            595                 600                 605

Cys Gln Leu Pro Leu Arg Val Ala Val Asp Leu Trp Ser Arg Arg Glu
610                 615                 620
```

Leu Ser Ala Gln Gly Pro Val Ala Trp Phe His Ala Gln Arg Arg Gln
625                 630                 635                 640

Thr Leu Gln Glu Gly Val Val Val Leu Leu Phe Ser Pro Gly Ala
            645                 650                 655

Val Ala Leu Cys Ser Glu Trp Leu Gln Asp Gly Val Ser Gly Pro Gly
        660                 665                 670

Ala His Gly Pro His Asp Ala Phe Arg Ala Ser Leu Ser Cys Val Leu
    675                 680                 685

Pro Asp Phe Leu Gln Gly Arg Ala Pro Gly Ser Tyr Val Gly Ala Cys
690                 695                 700

Phe Asp Arg Leu Leu His Pro Asp Ala Val Pro Ala Leu Phe Arg Thr
705                 710                 715                 720

Val Pro Val Phe Thr Leu Pro Ser Gln Leu Pro Asp Phe Leu Gly Ala
            725                 730                 735

Leu Gln Gln Pro Arg Ala Pro Arg Ser Gly Arg Leu Gln Glu Arg Ala
        740                 745                 750

Glu Gln Val Ser Arg Ala Leu Gln Pro Ala Leu Asp Ser Tyr Phe His
    755                 760                 765

Pro Pro Gly Thr Pro Ala Pro Gly Arg Gly Val Gly Pro Gly Ala Gly
770                 775                 780

Pro Gly Ala Gly Asp Gly Thr
785                 790

<210> SEQ ID NO 19
<211> LENGTH: 2478
<212> TYPE: DNA
<213> ORGANISM: Homo sapiens

<400> SEQUENCE: 19
aaaacgaaag cactccgtgc tggaagtagg aggagagtca ggactcccag gacagagagt    60
gcacaaacta cccagcacag cccctccgc cccctctgga ggctgaagag ggattccagc    120
ccctgccacc cacagacacg ggctgactgg ggtgtctgcc cccttgggg gggggcagca    180
cagggcctca ggcctgggtg ccacctggca cctagaagat gcctgtgccc tggttcttgc    240
tgtccttggc actgggccga agcccagtgg tcctttctct ggagaggctt gtggggcctc    300
aggacgctac ccactgctct ccgggcctct cctgccgcct ctgggacagt gacatactct    360
gcctgcctgg ggacatcgtg cctgctccgg gccccgtgct ggcgcctacg cacctgcaga    420
cagagctggt gctgaggtgc agaaggaga ccgactgtga cctctgtctg cgtgtggctg    480
tccacttggc cgtgcatggg cactgggaag agcctgaaga tgaggaaaag tttggaggag    540
cagctgactc aggggtggag gagcctagga atgcctctct ccaggcccaa gtcgtgctct    600
ccttccaggc ctaccctact gcccgctgcg tcctgctgga ggtgcaagtg cctgctgccc    660
ttgtgcagtt tggtcagtct gtgggctctg tggtatatga ctgcttcgag gctgccctag    720
ggagtgaggt acgaatctgg tcctatactc agcccaggta cgagaaggaa ctcaaccaca    780
cacagcagct gcctgactgc aggggctcg aagtctggaa cagcatcccg agctgctggg    840
ccctgccctg gctcaacgtg tcagcagatg gtgacaacgt gcatctggtt ctgaatgtct    900
ctgaggagca gcacttcggc ctctccctgt actggaatca ggtccagggc ccccaaaac    960
cccggtggca caaaaacctg actggaccgc agatcattac cttgaaccac acagacctgg    1020
ttccctgcct ctgtattcag gtgtggcctc tggaacctga ctccgttagg acgaacatct    1080
gcccccttcag ggaggacccc cgcgcacacc agaacctctg gcaagccgcc cgactgcgac    1140

```
tgctgaccct gcagagctgg ctgctggacg caccgtgctc gctgcccgca gaagcggcac    1200
tgtgctggcg ggctccgggt ggggacccct gccagccact ggtcccaccg ctttcctggg    1260
agaacgtcac tgtggacaag gttctcgagt tcccattgct gaaaggccac cctaacctct    1320
gtgttcaggt gaacagctcg gagaagctgc agctgcagga gtgcttgtgg ctgactccc    1380 tggggcctct caaagacgat gtgctactgt tggagacacg aggcccccag gacaacagat    1440
ccctctgtgc cttggaaccc agtggctgta cttcactacc cagcaaagcc tccacgaggg    1500
cagctcgcct tggagagtac ttactacaag acctgcagtc aggccagtgt ctgcagctat    1560
gggacgatga cttgggagcg ctatgggcct gccccatgga caaatacatc cacaagcgct    1620
gggccctcgt gtggctggcc tgcctactct ttgccgctgc gctttccctc atcctccttc    1680
tcaaaaagga tcacgcgaaa gggtggctga ggctcttgaa acaggacgtc cgctcggggg    1740
cggccgccag gggccgcgcg gctctgctcc tctactcagc cgatgactcg ggtttcgagc    1800
gcctggtggg cgccctggcg tcggcccgtg ccagctgcc gctgcgcgtg ccgtagacc    1860 tgtggagccg tcgtgaactg agcgcgcagg ggcccgtggc ttggtttcac gcgcagcggc    1920
gccagaccct gcaggagggc ggcgtggtgg tcttgctctt ctctcccggt gcggtggcgc    1980
tgtgcagcga gtggctacag gatggggtgt ccgggcccgg ggcgcacggc ccgcacgacg    2040
ccttccgcgc ctcgctcagc tgcgtgctgc ccgacttctt gcaggccgg gcgcccggca    2100 gctacgtggg ggcctgcttc gacaggctgc tccacccgga cgccgtaccc gccctttcc    2160 gcaccgtgcc cgtcttcaca ctgccctccc aactgccaga cttcctgggg gccctgcagc    2220
agcctcgcgc cccgcgttcc gggcggctcc aagagagagc ggagcaagtg tcccgggccc    2280
ttcagccagc cctggatagc tacttccatc ccccggggac tcccgcgccg ggacgcgggg    2340
tgggaccagg ggcgggacct ggggcggggg acgggactta aataaaggca gacgctgttt    2400
ttctacccat gtggcccaaa aaaaaaaaaa aaaaaaaaaa aaaaaaaaaa aaaaaaaaaa    2460
aaaaaaaaaa aaaaaaaa                                                  2478
```

<210> SEQ ID NO 20
<211> LENGTH: 720
<212> TYPE: PRT
<213> ORGANISM: Homo sapiens

<400> SEQUENCE: 20

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125
```

```
Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
370                 375                 380

Ala Asp Ser Leu Gly Pro Leu Lys Asp Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
        435                 440                 445

Asp Asp Asp Leu Gly Ala Leu Trp Ala Cys Pro Met Asp Lys Tyr Ile
450                 455                 460

His Lys Arg Trp Ala Leu Val Trp Leu Ala Cys Leu Leu Phe Ala Ala
465                 470                 475                 480

Ala Leu Ser Leu Ile Leu Leu Leu Lys Lys Asp His Ala Lys Gly Trp
                485                 490                 495

Leu Arg Leu Leu Lys Gln Asp Val Arg Ser Gly Ala Ala Ala Arg Gly
            500                 505                 510

Arg Ala Ala Leu Leu Leu Tyr Ser Ala Asp Asp Ser Gly Phe Glu Arg
        515                 520                 525

Leu Val Gly Ala Leu Ala Ser Ala Leu Cys Gln Leu Pro Leu Arg Val
530                 535                 540

Ala Val Asp Leu Trp Ser Arg Arg Glu Leu Ser Ala Gln Gly Pro Val
```

```
                545                 550                 555                 560
            Ala Trp Phe His Ala Gln Arg Arg Gln Thr Leu Gln Glu Gly Val
                            565                 570                 575

Val Val Leu Leu Phe Ser Pro Gly Ala Val Ala Leu Cys Ser Glu Trp
                        580                 585                 590

Leu Gln Asp Gly Val Ser Gly Pro Gly Ala His Gly Pro His Asp Ala
                        595                 600                 605

Phe Arg Ala Ser Leu Ser Cys Val Leu Pro Asp Phe Leu Gln Gly Arg
                    610                 615                 620

Ala Pro Gly Ser Tyr Val Gly Ala Cys Phe Asp Arg Leu Leu His Pro
            625                 630                 635                 640

Asp Ala Val Pro Ala Leu Phe Arg Thr Val Pro Val Phe Thr Leu Pro
                                645                 650                 655

Ser Gln Leu Pro Asp Phe Leu Gly Ala Leu Gln Gln Pro Arg Ala Pro
                            660                 665                 670

Arg Ser Gly Arg Leu Gln Glu Arg Ala Glu Gln Val Ser Arg Ala Leu
                        675                 680                 685

Gln Pro Ala Leu Asp Ser Tyr Phe His Pro Gly Thr Pro Ala Pro
                    690                 695                 700

Gly Arg Gly Val Gly Pro Gly Ala Gly Pro Gly Ala Gly Asp Gly Thr
            705                 710                 715                 720

<210> SEQ ID NO 21
<211> LENGTH: 2433
<212> TYPE: DNA
<213> ORGANISM: Homo sapiens

<400> SEQUENCE: 21
aaaacgaaag cactccgtgc tggaagtagg aggagagtca ggactcccag gacagagagt    60
gcacaaacta cccagcacag ccccctccgc ccctctggaa ggctgaagag ggattccagc   120
ccctgccacc cacagacacg ggctgactgg ggtgtctgcc cccttgggg gggggcagca   180
cagggcctca ggcctgggtg ccacctggca cctagaagat gcctgtgccc tggttcttgc   240
tgtccttggc actgggccga agcccagtgg tcctttctct ggagaggctt gtgggcctc   300
aggacgctac ccactgctct ccgggcctct cctgccgcct ctgggacagt gacatactct   360
gcctgcctgg ggacatcgtg cctgctccgg gcccgtgct ggcgcctacg cacctgcaga   420
cagagctggt gctgaggtgc agaaggaga ccgactgtga cctctgtctg cgtgtggctg   480
tccacttggc cgtgcatggg cactgggaag agcctgaaga tgaggaaaag tttggaggag   540
cagctgactc agggggtggag gagcctagga atgcctctct ccaggcccaa gtcgtgctct   600
ccttccaggc ctaccctact gcccgctgcg tcctgctgga ggtgcaagtg cctgctgccc   660
tgtgcagtt tggtcagtct gtgggctctg tggtatatga ctgcttcgag gctgccctag   720
ggagtgaggt acgaatctgg tcctatactc agcccaggta cgagaaggaa ctcaaccaca   780
cacagcagct gcctgccctg ccctggctca acgtgtcagc agatggtgac aacgtgcatc   840
tggttctgaa tgtctctgag gagcagcact tcggcctctc cctgtactgg aatcaggtcc   900
agggcccccc aaaccccgg tggcacaaaa acctgactgg accgcagatc attaccttga   960
accacacaga cctggttccc tgcctctgta ttcaggtgtg gcctctggaa cctgactccg  1020
ttaggacgaa catctgcccc ttcagggagg accccgcgc acaccagaac ctctggcaag  1080
ccgcccgact gcgactgctg accctgcaga gctggctgct ggacgcaccg tgctcgctgc  1140
ccgcagaagc ggcactgtgc tggcgggctc cgggtgggga cccctgccag ccactggtcc  1200
```

-continued

```
caccgctttc ctgggagaac gtcactgtgg acaaggttct cgagttccca ttgctgaaag      1260
gccaccctaa cctctgtgtt caggtgaaca gctcggagaa gctgcagctg caggagtgct      1320
tgtgggctga ctccctgggg cctctcaaag acgatgtgct actgttggag acacgaggcc      1380
cccaggacaa cagatccctc tgtgccttgg aacccagtgg ctgtacttca ctacccagca      1440
aagcctccac gagggcagct cgccttggag agtacttact acaagacctg cagtcaggcc      1500
agtgtctgca gctatgggac gatgacttgg gagcgctatg ggcctgcccc atggacaaat      1560
acatccacaa gcgctgggcc ctcgtgtggc tggcctgcct actctttgcc gctgcgcttt      1620
ccctcatcct ccttctcaaa aaggatcacg cgaaagggtg gctgaggctc ttgaaacagg      1680
acgtccgctc ggggcggcc gccaggggcc gcgcggctct gctcctctac tcagccgatg      1740
actcgggttt cgagcgcctg gtgggcgccc tggcgtcggc cctgtgccag ctgccgctgc      1800
gcgtggccgt agacctgtgg agccgtcgtg aactgagcgc gcaggggccc gtggcttggt      1860
ttcacgcgca gcggcgccag accctgcagg agggcggcgt ggtggtcttg ctcttctctc      1920
ccggtgcggt ggcgctgtgc agcgagtggc tacaggatgg ggtgtccggg cccggggcgc      1980
acggcccgca cgacgccttc cgcgcctcgc tcagctgcgt gctgcccgac ttcttgcagg      2040
gccgggcgcc cggcagctac gtgggggcct gcttcgacag gctgctccac ccggacgccg      2100
tacccgcccc tttccgcacc gtgcccgtct tcacactgcc ctcccaactg ccagacttcc      2160
tgggggccct gcagcagcct cgcgccccgc gttccgggcg gctccaagag agagcggagc      2220
aagtgtcccg ggcccttcag ccagccctgg atagctactt ccatccccg gggactcccg      2280 cgccgggacg cggggtggga ccaggggcgg gacctggggc ggggggacggg acttaaataa      2340 aggcagacgc tgttttctcta cccatgtggc ccaaaaaaaa aaaaaaaaaa aaaaaaaaaa      2400
aaaaaaaaaa aaaaaaaaaa aaaaaaaaaa aaa                                   2433
```

<210> SEQ ID NO 22
<211> LENGTH: 705
<212> TYPE: PRT
<213> ORGANISM: Homo sapiens

<400> SEQUENCE: 22

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
                20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
        50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
```

-continued

```
             145                 150                 155                 160
        Asp Cys Phe Glu Ala Ala Leu Gly Ser Glu Val Arg Ile Trp Ser Tyr
                            165                 170                 175
        Thr Gln Pro Arg Tyr Glu Lys Glu Leu Asn His Thr Gln Gln Leu Pro
                            180                 185                 190
        Ala Leu Pro Trp Leu Asn Val Ser Ala Asp Gly Asp Asn Val His Leu
                            195                 200                 205
        Val Leu Asn Val Ser Glu Glu Gln His Phe Gly Leu Ser Leu Tyr Trp
        210                 215                 220
        Asn Gln Val Gln Gly Pro Pro Lys Pro Arg Trp His Lys Asn Leu Thr
        225                 230                 235                 240
        Gly Pro Gln Ile Ile Thr Leu Asn His Thr Asp Leu Val Pro Cys Leu
                            245                 250                 255
        Cys Ile Gln Val Trp Pro Leu Glu Pro Asp Ser Val Arg Thr Asn Ile
                            260                 265                 270
        Cys Pro Phe Arg Glu Asp Pro Arg Ala His Gln Asn Leu Trp Gln Ala
                            275                 280                 285
        Ala Arg Leu Arg Leu Leu Thr Leu Gln Ser Trp Leu Leu Asp Ala Pro
                            290                 295                 300
        Cys Ser Leu Pro Ala Glu Ala Ala Leu Cys Trp Arg Ala Pro Gly Gly
        305                 310                 315                 320
        Asp Pro Cys Gln Pro Leu Val Pro Pro Leu Ser Trp Glu Asn Val Thr
                            325                 330                 335
        Val Asp Lys Val Leu Glu Phe Pro Leu Leu Lys Gly His Pro Asn Leu
                            340                 345                 350
        Cys Val Gln Val Asn Ser Ser Glu Lys Leu Gln Leu Gln Glu Cys Leu
                            355                 360                 365
        Trp Ala Asp Ser Leu Gly Pro Leu Lys Asp Asp Val Leu Leu Leu Glu
                            370                 375                 380
        Thr Arg Gly Pro Gln Asp Asn Arg Ser Leu Cys Ala Leu Glu Pro Ser
        385                 390                 395                 400
        Gly Cys Thr Ser Leu Pro Ser Lys Ala Ser Thr Arg Ala Ala Arg Leu
                            405                 410                 415
        Gly Glu Tyr Leu Leu Gln Asp Leu Gln Ser Gly Gln Cys Leu Gln Leu
                            420                 425                 430
        Trp Asp Asp Asp Leu Gly Ala Leu Trp Ala Cys Pro Met Asp Lys Tyr
                            435                 440                 445
        Ile His Lys Arg Trp Ala Leu Val Trp Leu Ala Cys Leu Leu Phe Ala
                            450                 455                 460
        Ala Ala Leu Ser Leu Ile Leu Leu Leu Lys Lys Asp His Ala Lys Gly
        465                 470                 475                 480
        Trp Leu Arg Leu Leu Lys Gln Asp Val Arg Ser Gly Ala Ala Ala Arg
                            485                 490                 495
        Gly Arg Ala Ala Leu Leu Leu Tyr Ser Ala Asp Asp Ser Gly Phe Glu
                            500                 505                 510
        Arg Leu Val Gly Ala Leu Ala Ser Ala Leu Cys Gln Leu Pro Leu Arg
                            515                 520                 525
        Val Ala Val Asp Leu Trp Ser Arg Arg Glu Leu Ser Ala Gln Gly Pro
        530                 535                 540
        Val Ala Trp Phe His Ala Gln Arg Arg Gln Thr Leu Gln Glu Gly Gly
        545                 550                 555                 560
        Val Val Val Leu Leu Phe Ser Pro Gly Ala Val Ala Leu Cys Ser Glu
                            565                 570                 575
```

```
Trp Leu Gln Asp Gly Val Ser Gly Pro Gly Ala His Gly Pro His Asp
            580                 585                 590
Ala Phe Arg Ala Ser Leu Ser Cys Val Leu Pro Asp Phe Leu Gln Gly
        595                 600                 605
Arg Ala Pro Gly Ser Tyr Val Gly Ala Cys Phe Asp Arg Leu Leu His
    610                 615                 620
Pro Asp Ala Val Pro Ala Leu Phe Arg Thr Val Pro Val Phe Thr Leu
625                 630                 635                 640
Pro Ser Gln Leu Pro Asp Phe Leu Gly Ala Leu Gln Gln Pro Arg Ala
                645                 650                 655
Pro Arg Ser Gly Arg Leu Gln Glu Arg Ala Glu Gln Val Ser Arg Ala
            660                 665                 670
Leu Gln Pro Ala Leu Asp Ser Tyr Phe His Pro Pro Gly Thr Pro Ala
        675                 680                 685
Pro Gly Arg Gly Val Gly Pro Gly Ala Gly Pro Gly Ala Gly Asp Gly
    690                 695                 700
Thr
705

<210> SEQ ID NO 23
<211> LENGTH: 8720
<212> TYPE: DNA
<213> ORGANISM: Homo sapiens

<400> SEQUENCE: 23
gcggccgccg cggccaccgc ccactcgggg ctggccagcg gcgggcggcc ggggcgcaga      60
gaacggcctg gctgggcgag cgcacggcca tggccccgtg gctgcagctc tgctccgtct     120
tctttacggt caacgcctgc ctcaacggct cgcagctggc tgtggccgct ggcgggtccg     180
gccgcgcgcg gggcgccgac acctgtggct ggaggggagt ggggccagcc agcagaaaca     240
gtgggctgta caacatcacc ttcaaatatg acaattgtac cacctacttg aatccagtgg     300
ggaagcatgt gattgctgac gcccagaata tcaccatcag ccagtatgct tgccatgacc     360
aagtggcagt caccattctt tggtccccag gggccctcgg catcgaattc ctgaaaggat     420 tcgggtaat actggaggag ctgaagtcgg agggaagaca gtgccaacaa ctgattctaa     480
aggatccgaa gcagctcaac agtagcttca aaagaactgg aatggaatct caacctttcc     540
tgaatatgaa atttgaaacg gattatttcg taaaggttgt ccctttcct tccattaaaa     600 acgaaagcaa ttaccaccct ttcttcttta gaacccgagc ctgtgacctg ttgttacagc     660
cggacaatct agcttgtaaa cccttctgga agcctcggaa cctgaacatc agccagcatg     720
gctcggacat gcaggtgtcc ttcgaccatg caccgcacaa cttcggcttc cgtttcttct     780
atcttcacta caagctcaag cacgaaggac ctttcaagcg aaagacctgt aagcaggagc     840
aaactacaga gacgaccagc tgcctccttc aaaatgtttc tccaggggat tatataattg     900
agctggtgga tgacactaac acaacaagaa aagtgatgca ttatgcctta aagccagtgc     960
actccccgtg ggccgggccc atcagagccg tggccatcac agtgccactg gtagtcatat    1020
cggcattcgc gacgctcttc actgtgatgt gccgcaagaa gcaacaagaa atatatatt    1080 cacatttaga tgaagagagc tctgagtctt ccacatacac tgcagcactc ccaagagaga    1140
ggctccggcc gcggccgaag gtctttctct gctattccag taaagatggc cagaatcaca    1200
tgaatgtcgt ccagtgtttc gcctacttcc tccaggactt ctgtggctgt gaggtggctc    1260
tggacctgtg ggaagacttc agcctctgta gagaagggca gagagaatgg gtcatccaga    1320
```

```
agatccacga gtcccagttc atcattgtgg tttgttccaa aggtatgaag tactttgtgg   1380
acaagaagaa ctacaaacac aaaggaggtg gccgaggctc ggggaaagga gagctcttcc   1440
tggtggcggt gtcagccatt gccgaaaagc tccgccaggc caagcagagt tcgtccgcgg   1500
cgctcagcaa gtttatcgcc gtctactttg attattcctg cgagggagac gtccccggta   1560
tcctagacct gagtaccaag tacagactca tggacaatct tcctcagctc tgttcccact   1620
tgcactcccg agaccacggc ctccaggagc cggggcagca cacgcgacag ggcagcagaa   1680
ggaactactt ccggagcaag tcaggccggt ccctatacgt cgccatttgc aacatgcacc   1740
agtttattga cgaggagccc gactggttcg aaaagcagtt cgttcccttc catcctcctc   1800
cactgcgcta ccgggagcca gtcttggaga aatttgattc gggcttggtt ttaaatgatg   1860
tcatgtgcaa accagggcct gagagtgact tctgcctaaa ggtagaggcg gctgttcttg   1920
gggcaaccgg accagccgac tcccagcacg agagtcagca tggggcctg gaccaagacg   1980 gggaggcccg gcctgccctt gacggtagcc ccgccctgca cccctgctg cacacggtga   2040 aagccggcag cccctcggac atgccgcggg actcaggcat ctatgactcg tctgtgccct   2100
catccgagct gtctctgcca ctgatggaag actctcgac ggaccagaca gaaacgtctt   2160
ccctgacgga gagcgtgtcc tcctcttcag gcctgggtga ggaggaacct cctgcccttc   2220
cttccaagct cctctcttct gggtcatgca aagcagatct tggttgccgc agctacactg   2280
atgaactcca cgcggtcgcc cctttgtaac aaaacgaaag agtctaagca ttgccacttt   2340
agctgctgcc tccctctgat tccccagctc atctccctgg ttgcatggcc cacttggagc   2400
tgaggtctca tacaaggata tttggagtga atgctggcc agtacttgtt ctcccttgcc   2460 ccaaccctt accggatatc ttgacaaact ctccaatttt ctaaaatgat atggagctct   2520
gaaaggcatg tccataaggt ctgacaacag cttgccaaat ttggttagtc cttggatcag   2580
agcctgttgt gggaggtagg gaggaaatat gtaaagaaaa acaggaagat acctgcacta   2640
atcattcaga cttcattgag ctctgcaaac tttgcctgtt tgctattggc taccttgatt   2700
tgaaatgctt tgtgaaaaaa ggcacttta acatcatagc cacagaaatc aagtgccagt   2760
ctatctggaa tccatgttgt attgcagata atgttctcat ttattttga tgtagaattt   2820 acattgccat gggtgttaaa taagctttga gtcaaaagtc aagaaagtga ctgaatatac   2880
agtcaccttt tatgaaatga gtctctgtgt tactgggtgg catgactgat tgaggtgaag   2940
ctcacggggc caggctgacc gtcttgaccg ttccacttga gataggttgg tcatcgtgca   3000
gaaggcccca ggacctcagc acacacagcc tcctcttggt ctgagtaggc atcatgtggg   3060
ggccagatct gcctgctgtt tccatggggtt acatttactg tgctgtatct cagatgttgg   3120
tgtctggaag tttattctta agagactgct acccagctgg tctgtattat ggaagttgc   3180 agttcgtgct ttggttggcc ttctggtcta aagctgtgtc ctgaatatta gggatcacaa   3240
ttcactgaaa tacagcagtg tgtggagtg atggccagt aatctgctga actggttttg   3300
actaatgaca aacctctttt taagatggta gaatggaggt gatagtcaca aaagtaaatg   3360
ttccattttt atgaatgact ttctacagag tttctatttc taaagaaaaa acaattgttc   3420
acatcccatc tgatgattag catgtgtgta atgaatgctg tcttggtctc ccctgtggaa   3480
acccttctcc ctgtgcctta gagcaggtgt gtacatctct cactacctttt ctcatgggtg   3540 ctgttagatt ttggcacccg ttttctcagc attcagccca gggaatgtgg ttttcacttc   3600
ttcgtcagat aagaccaaca tgaagggta tgttgagaaa catcctgagg caaggtggga   3660
```

-continued

```
ggtgggatgg ggcaggactt tcccttccaa gcacatgcat ggcaggtggg gaaaggggg    3720
cttgcacccc tgctggaaag aaaaggtttg tgtatatttc tgatgcaaat gtcatactca    3780
ctgctctgta aaggcagctg gcagcttttt gggaaaagaa cgtgctcgtc tgttctctgg    3840
catcaagttt cttgcagctg ctctgaggga gagacagtga gctgcaagac tgcctcccca    3900
taacaacagg caactcagag aagagtcatt ttatgttgtt cctatggaat ctggaatgag    3960
tgcagagctc ctaccacac atgactgccc cgccatttca tcctaggcat tctgtgaagg      4020
agattggtta gtccaaactt gctaacatac gaaaattcac ttggaacatg atgagagatt    4080
tcttattgag gccaagagat gtttcctgtc cagaggaaac cattaggagt cgcttttagg    4140
gtattcagct ttgttcatga aataaggcat ctctgagaaa gtggcccag ggagagaatg     4200
gaggactggg aggagaagca ttaactgagc tccaagggtg tgtgggcaga gagcttgcta    4260
tgtgaactca ctccttaaga aaatggaaga gaaaagaga gtgctagtta aaaaatcggg     4320
atgttttagt ttggatttag ggttttgata cttatgttga aatactaatg tttctgatca    4380
ataaaatcaa actcttaata taccgagtaa tgaaaccata gtgtgattgc ctcagaataa    4440
attgagaagt ccaacttcct agttttgttt aattagtttc acttttttcta ctctccccag   4500
tatgctagaa atgggaatcg ttgccctgca gattacggca aaacatctgt tttaagcaaa    4560
gctgcatttt ttgactcaga aattgtccca gacggtggat ataagatgaa attcagaaaa    4620
acgttctgcc aagtcacagg cttttagata ttatggaaac aagaaatgga aaacaggatg    4680
atctccatga gaggccttga tcctgagagt aaaaggcttg tgtagatagg ttagacaacg    4740
tcctctagaa aagagaccag ggataagtcc aggtttccag gaaaaccaag aagcctgcgg    4800
gtagctgaag gtagagtgct agttgttcat cttaacttac caatgagcta cagaaaggac    4860
ttagcatctg atgtcatcag ctttgccagg agagtgatca aggaggttaa agctcaggta    4920
aaggtgtgcc ttctcagaga ttggctacaa gcaacagaga ccacctcaac agagaccacc    4980
tcaacagact cagcccagcc atacaaggtg ccaaagctcc tccagagggc tgtcttgggc    5040
cttttgaggca attgatctcc agaaagagtc agaagtcatt ccagtccagg cccaggtatt    5100
cagatggtga cccagccaga taatagtatc ttgagcaaat aatagtatct tgagtgcaaa    5160
taagcaggaa gactgtcctt caaaaaatgt ggggttacat gattttcaga gcctttttt     5220
cagagttgag catcttttct tttaaaagaa ataaggggca agaggaccaa ttttattcct    5280
tgaggaaaaa tgacacaccc ttctcccaaa agaaagaaaa ctctctggcc ccccaacttc    5340
aacactaatt tggctccctg aagaagagag aaaatattat ttctgtcttt attgaagaga    5400
aatgggcaat gccaatgtga aggttactag tcttttttat tttctattgg tgaagactac    5460
tactgctctt atttagcaga tcttataacct tcagtggtca ccagtatagc aggtgaggta   5520
taaggaaaac agcagtgtga tgataaatgg taattaatat actttgtctg tgtcagcaat    5580
agggaatggt ggggactgtg gcaaactgaa gcgcccctgt tccacccaca gtgggtaatt    5640
ttccagtcga ctgtggccat gaagtacttc ctgatcttcc cattttttcaa gaaaagctga   5700
caatctggat ttttatatga aaaattctga ttttaaaaaa tattggcaac taagttaaaa    5760
ttcaagtgaa tttagaccca gcagaagaca tggatggacc tgatttggtc cactgactac    5820
cagtttgtta acctgtgctt tataagattt gaaggaaagg cattcatggt aattacagac    5880
ggtgccacca gaaaatgctc ttgctaaatg cagccagtag ttagattgct tctttctcca    5940
gtctcccccg caaagaaatt tgacgtgatt ctgaatgcac tggacatgtc ttgattgcgt    6000
ctttacattt cacagtgtct taaaagaaag gcaagccagt tgttaatttc agaatcagat    6060
```

```
ttatgctctc tcaatttaaa aaatgctggg aacaatttca ttttttttt tttgagatgg   6120
agtcttgctc tgttgcccag gctggagtgc agtggcgtga tctcggctca ctgcaagctc   6180
cacctcccgg gttcacgcca ttctcctgcc tcagcctcct gagtagctgg gactacaggc   6240
gcccaccacc acgcctggct aattttttg tattttagt agagacgggg tttcactgtg     6300
ttagccagga tgatctcgat ctcctgacct ggtgatccgc ttgcctcggc ctcccaaagt   6360
gctgggatta caggcgtgag ccactgcgcc cggcctaaca atttcattta aactccacaa   6420
cctaaagggc tttgtttata gttttagctc ttggcataat ttttttcagg tggtgtgcaa   6480
ttctgagcat aggccaagac atgattagga aagcaggcag ttgtagagag taaggcaagg   6540
aacctcctag cgtccattag agccaggtat ttgcattatc ttccgtttta agtggtctgt   6600
gaattgactg tgttttggag gtgtgaaaca gtatacagag aaaagctttt cctgatactg   6660
agatatcagt taggagtcca aatggggtgt tgggtcatcc ttgccatatc acctcctttc   6720
caggctcaga gtgaaaatag acaaaaggaa atctgactgc aagccagtgg ctttgattcc   6780
agtttcagag tttagggact aggagagagt ttagattatc tagcatattc tccccctggt   6840
gtcagacagg gctgtgcctg aattattcca gacatatggc tgtagatggt attctttatt   6900
ttataagaag gagattctgt aacctaccct gctgatcaga tagttctttg tatgtcttag   6960
agaaattcaa gccagcttcc ttttgttcgg cttgtagtgg agaaagaaca gctggtcacc   7020
ttccatgtat tcaaaaacca cagtgaagtc atcccctgg tgtttttatt tcagtgataa     7080
ataattccac ccacttaaac cattcttcat ggctcttgtt ttccaggggc ctaataattt   7140
tcactgctgt aatgtttctc agcttcacac ttagtttagt tgcccaaaca atgttggtgc   7200
cttactcaca ttggtgcctt gtgaagacga ggctcaggat gggattatg gggaaattct     7260
tgcacaccca gctcctctta ccacttaaaa atataatggc actttcacaa aatgatatgt   7320
cacctatatt cattgagaat tatttgactg ccacattttt cccctgatga tagtcatcta   7380
tcataacttg tgtttgtttt cctcctgaga tcaaacactt ggtgcttatt cctgatgtat   7440
actctgagac cagctcttac cttctgagtg gcagctaccc ctccctccca attttagatc   7500
ctatttttac acatctctat agatatcacc tttatttcat gactcacaat attaaatggt   7560
acagacttca gtttaaccac tggtgtggta acagcagtag ttgctaagta ccaccttccc   7620
attgctgttt gagggctaat ttgcaaagac atttgaatct cccagtgaag atgtctgggg   7680
aattttggcc agttgtcttc cctcttgccc ttttgttctt taaaattcag cttggaccat   7740
agacacctcc aggatcttgt ttatgttctg ctctcaattg accaagcact gcgttttgca   7800
caatcagaag tctcacaaaa gcaaacagtt atgactgcat atctgatgtt tatatcctat   7860
aaaatttcag gaagattcag agtcaatctt ctatttgtac atgatgtaga caaaattagc   7920
tgctccaatt gttagacaaa aaattgccat tggattacac taatgtgctc atctgttgtt   7980
ttaaaagttt ggtatcaggc ggggcacggt ggctcacgcc tgtaatccca gcattttggg   8040
aggccaaggt gggcggatca cctgaggtcc agagttcaag accagcctga ccaacatggt   8100
gaaaccctgt ctctactaaa aatacaaaat taatcaggcg tggttgtgtg tgcctgtaat   8160
cccagctact cgagaggctg aggcaggaga atcgcttgaa tccgggaggc agaggttgca   8220
gtgagctgag atcacgccat tgcactctag cctgggcaac aagagcgaaa ctccgtctca   8280
acaacaacaa caaaaagttt ggtatgtttc tctcaagaaa aaagcatggt gagtccagac   8340
agcagcaaaa gcttttgtga aaaccaattg tgttcatcta gatagtaagt aactcctatt   8400
```

-continued

```
tttactgtta atttttaaaa agagaatttt tccctgtgga aactccctgt tagtacgtcc    8460 tagggagaa agcctgtgga atatggtggt tattgatggc gttgcctttg tttcatcttt    8520
gagtttgccc tttgtgggat ctagtgggat aatgagcact gacagaactc ttaacagcgt    8580
gctgtatttt tgacattgaa aatgttaatg acttgatttg tacataactc tgtaactagg    8640
tgaaagtaga tcacagctga catttacaaa atgtttttgt accttagaat ttctgcatta    8700
aataaaatgt tttgttttaa                                               8720
```

<210> SEQ ID NO 24
<211> LENGTH: 739
<212> TYPE: PRT
<213> ORGANISM: Homo sapiens

<400> SEQUENCE: 24

```
Met Ala Pro Trp Leu Gln Leu Cys Ser Val Phe Phe Thr Val Asn Ala
1               5                   10                  15

Cys Leu Asn Gly Ser Gln Leu Ala Val Ala Ala Gly Gly Ser Gly Arg
            20                  25                  30

Ala Arg Gly Ala Asp Thr Cys Gly Trp Arg Val Gly Pro Ala Ser
        35                  40                  45

Arg Asn Ser Gly Leu Tyr Asn Ile Thr Phe Lys Tyr Asp Asn Cys Thr
    50                  55                  60

Thr Tyr Leu Asn Pro Val Gly Lys His Val Ile Ala Asp Ala Gln Asn
65                  70                  75                  80

Ile Thr Ile Ser Gln Tyr Ala Cys His Asp Gln Val Ala Val Thr Ile
                85                  90                  95

Leu Trp Ser Pro Gly Ala Leu Gly Ile Glu Phe Leu Lys Gly Phe Arg
            100                 105                 110

Val Ile Leu Glu Glu Leu Lys Ser Glu Gly Arg Gln Cys Gln Gln Leu
        115                 120                 125

Ile Leu Lys Asp Pro Lys Gln Leu Asn Ser Ser Phe Lys Arg Thr Gly
    130                 135                 140

Met Glu Ser Gln Pro Phe Leu Asn Met Lys Phe Glu Thr Asp Tyr Phe
145                 150                 155                 160

Val Lys Val Val Pro Phe Pro Ser Ile Lys Asn Glu Ser Asn Tyr His
                165                 170                 175

Pro Phe Phe Arg Thr Arg Ala Cys Asp Leu Leu Gln Pro Asp
            180                 185                 190

Asn Leu Ala Cys Lys Pro Phe Trp Lys Pro Arg Asn Leu Asn Ile Ser
        195                 200                 205

Gln His Gly Ser Asp Met Gln Val Ser Phe Asp His Ala Pro His Asn
    210                 215                 220

Phe Gly Phe Arg Phe Phe Tyr Leu His Tyr Lys Leu Lys His Glu Gly
225                 230                 235                 240

Pro Phe Lys Arg Lys Thr Cys Lys Gln Glu Gln Thr Thr Glu Thr Thr
                245                 250                 255

Ser Cys Leu Leu Gln Asn Val Ser Pro Gly Asp Tyr Ile Ile Glu Leu
            260                 265                 270

Val Asp Asp Thr Asn Thr Thr Arg Lys Val Met His Tyr Ala Leu Lys
        275                 280                 285

Pro Val His Ser Pro Trp Ala Gly Pro Ile Arg Ala Val Ala Ile Thr
    290                 295                 300

Val Pro Leu Val Val Ile Ser Ala Phe Ala Thr Leu Phe Thr Val Met
305                 310                 315                 320
```

```
Cys Arg Lys Lys Gln Gln Glu Asn Ile Tyr Ser His Leu Asp Glu Glu
                325                 330                 335

Ser Ser Glu Ser Ser Thr Tyr Thr Ala Ala Leu Pro Arg Glu Arg Leu
            340                 345                 350

Arg Pro Arg Pro Lys Val Phe Leu Cys Tyr Ser Ser Lys Asp Gly Gln
                355                 360                 365

Asn His Met Asn Val Val Gln Cys Phe Ala Tyr Phe Leu Gln Asp Phe
        370                 375                 380

Cys Gly Cys Glu Val Ala Leu Asp Leu Trp Glu Asp Phe Ser Leu Cys
385                 390                 395                 400

Arg Glu Gly Gln Arg Glu Trp Val Ile Gln Lys Ile His Glu Ser Gln
                405                 410                 415

Phe Ile Ile Val Val Cys Ser Lys Gly Met Lys Tyr Phe Val Asp Lys
                420                 425                 430

Lys Asn Tyr Lys His Lys Gly Gly Arg Gly Ser Gly Lys Gly Glu
        435                 440                 445

Leu Phe Leu Val Ala Val Ser Ala Ile Ala Glu Lys Leu Arg Gln Ala
    450                 455                 460

Lys Gln Ser Ser Ser Ala Ala Leu Ser Lys Phe Ile Ala Val Tyr Phe
465                 470                 475                 480

Asp Tyr Ser Cys Glu Gly Asp Val Pro Gly Ile Leu Asp Leu Ser Thr
                485                 490                 495

Lys Tyr Arg Leu Met Asp Asn Leu Pro Gln Leu Cys Ser His Leu His
                500                 505                 510

Ser Arg Asp His Gly Leu Gln Glu Pro Gly Gln His Thr Arg Gln Gly
                515                 520                 525

Ser Arg Arg Asn Tyr Phe Arg Ser Lys Ser Gly Arg Ser Leu Tyr Val
        530                 535                 540

Ala Ile Cys Asn Met His Gln Phe Ile Asp Glu Pro Asp Trp Phe
545                 550                 555                 560

Glu Lys Gln Phe Val Pro Phe His Pro Pro Leu Arg Tyr Arg Glu
                565                 570                 575

Pro Val Leu Glu Lys Phe Asp Ser Gly Leu Val Leu Asn Asp Val Met
                580                 585                 590

Cys Lys Pro Gly Pro Glu Ser Asp Phe Cys Leu Lys Val Glu Ala Ala
            595                 600                 605

Val Leu Gly Ala Thr Gly Pro Ala Asp Ser Gln His Glu Ser Gln His
        610                 615                 620

Gly Gly Leu Asp Gln Asp Gly Glu Ala Arg Pro Ala Leu Asp Gly Ser
625                 630                 635                 640

Ala Ala Leu Gln Pro Leu Leu His Thr Val Lys Ala Gly Ser Pro Ser
                645                 650                 655

Asp Met Pro Arg Asp Ser Gly Ile Tyr Asp Ser Ser Val Pro Ser Ser
            660                 665                 670

Glu Leu Ser Leu Pro Leu Met Glu Gly Leu Ser Thr Asp Gln Thr Glu
            675                 680                 685

Thr Ser Ser Leu Thr Glu Ser Val Ser Ser Ser Gly Leu Gly Glu
    690                 695                 700

Glu Glu Pro Pro Ala Leu Pro Ser Lys Leu Leu Ser Ser Gly Ser Cys
705                 710                 715                 720

Lys Ala Asp Leu Gly Cys Arg Ser Tyr Thr Asp Glu Leu His Ala Val
                725                 730                 735
```

Ala Pro Leu

<210> SEQ ID NO 25
<211> LENGTH: 8742
<212> TYPE: DNA
<213> ORGANISM: Homo sapiens

<400> SEQUENCE: 25

| | | | | | |
|---|---|---|---|---|---|
| atccgctctt | cttttcctcc | gggaaaagaa | acgggaagtg | gccgtgggcc | ggtgaattcc | 60 |
| gtgtagtggc | caagctttgt | tccaaagagg | gggaggtggt | gacagtctct | tgcccactga | 120 |
| agcgtgccag | acagagtgct | aggcatgggg | gcagaggtga | atcagatgac | agccacctct | 180 |
| caccacgagg | agtggctgaa | agtgtgactg | gactacaggc | aatcctggcc | ttggcaggga | 240 |
| gtggggccag | ccagcagaaa | cagtgggctg | tacaacatca | ccttcaaata | tgacaattgt | 300 |
| accacctact | tgaatccagt | ggggaagcat | gtgattgctg | acgccagaa | tatcaccatc | 360 |
| agccagtatg | cttgccatga | ccaagtggca | gtcaccattc | tttggtcccc | aggggccctc | 420 |
| ggcatcgaat | tcctgaaagg | atttcgggta | atactggagg | agctgaagtc | ggagggaaga | 480 |
| cagtgccaac | aactgattct | aaaggatccg | aagcagctca | acagtagctt | caaagaact | 540 |
| ggaatggaat | ctcaaccttt | cctgaatatg | aaatttgaaa | cggattattt | cgtaaaggtt | 600 |
| gtccctttc | cttccattaa | aaacgaaagc | aattaccacc | cttcttctt | tagaacccga | 660 |
| gcctgtgacc | tgttgttaca | gccggacaat | ctagcttgta | aacccttctg | gaagcctcgg | 720 |
| aacctgaaca | tcagccagca | tggctcggac | atgcaggtgt | ccttcgacca | tgcaccgcac | 780 |
| aacttcggct | tccgtttctt | ctatcttcac | tacaagctca | agcacgaagg | accttttcaag | 840 |
| cgaaagacct | gtaagcagga | gcaaactaca | gagacgacca | gctgcctcct | tcaaaatgtt | 900 |
| tctccagggg | attatataat | tgagctggtg | gatgacacta | acacaacaag | aaaagtgatg | 960 |
| cattatgcct | taaagccagt | gcactccccg | tgggccgggc | ccatcagagc | cgtggccatc | 1020 |
| acagtgccac | tggtagtcat | atcggcattc | gcgacgctct | tcactgtgat | gtgccgcaag | 1080 |
| aagcaacaag | aaaatatata | ttcacattta | gatgaagaga | gctctgagtc | ttccacatac | 1140 |
| actgcagcac | tcccaagaga | gaggctccgg | ccgcggccga | aggtctttct | ctgctattcc | 1200 |
| agtaaagatg | gccagaatca | catgaatgtc | gtccagtgtt | tcgcctactt | cctccaggac | 1260 |
| ttctgtggct | gtgaggtggc | tctggacctg | tgggaagact | tcagcctctg | tagagaaggg | 1320 |
| cagagagaat | gggtcatcca | gaagatccac | gagtcccagt | tcatcattgt | ggtttgttcc | 1380 |
| aaaggtatga | agtactttgt | ggacaagaag | aactacaaac | acaaaggagg | tggccgaggc | 1440 |
| tcggggaaag | gagagctctt | cctggtggcg | gtgtcagcca | ttgccgaaaa | gctccgccag | 1500 |
| gccaagcaga | gttcgtccgc | ggcgctcagc | aagtttatcg | ccgtctactt | tgattattcc | 1560 |
| tgcgagggag | acgtccccgg | tatcctagac | ctgagtacca | agtacagact | catggacaat | 1620 |
| cttcctcagc | tctgttccca | cttgcactcc | cgagaccacg | gcctccagga | gccggggcag | 1680 |
| cacacgcgac | agggcagcag | aaggaactac | ttccggagca | agtcaggccg | gtccctatac | 1740 |
| gtcgccattt | gcaacatgca | ccagtttatt | gacgaggagc | ccgactggtt | cgaaaagcag | 1800 |
| ttcgttccct | tccatcctcc | tccactgcgc | taccggagc | cagtcttgga | gaaatttgat | 1860 |
| tcgggcttgg | ttttaaatga | tgtcatgtgc | aaaccagggc | ctgagagtga | cttctgccta | 1920 |
| aaggtagagg | cggctgttct | tggggcaacc | ggaccagccg | actcccagca | cgagagtcag | 1980 |
| catgggggcc | tggaccaaga | cggggaggcc | cggcctgccc | ttgacggtag | cgccgccctg | 2040 |
| caaccccctgc | tgcacacggt | gaaagccggc | agccctcgg | acatgccgcg | ggactcaggc | 2100 |

```
atctatgact cgtctgtgcc ctcatccgag ctgtctctgc cactgatgga aggactctcg    2160
acggaccaga cagaaacgtc ttccctgacg gagagcgtgt cctcctcttc aggcctgggt    2220
gaggaggaac ctcctgccct tccttccaag ctcctctctt ctgggtcatg caaagcagat    2280
cttggttgcc gcagctacac tgatgaactc cacgcggtcg cccctttgta acaaaacgaa    2340
agagtctaag cattgccact ttagctgctg cctccctctg attccccagc tcatctccct    2400
ggttgcatgg cccacttgga gctgaggtct catacaagga tatttggagt gaaatgctgg    2460
ccagtacttg ttctcccttg ccccaaccct ttaccggata tcttgacaaa ctctccaatt    2520
ttctaaaatg atatggagct ctgaaaggca tgtccataag gtctgacaac agcttgccaa    2580
atttggttag tccttggatc agagcctgtt gtgggaggta gggaggaaat atgtaaagaa    2640
aaacaggaag atacctgcac taatcattca gacttcattg agctctgcaa actttgcctg    2700
tttgctattg ctaccttga tttgaaatgc tttgtgaaaa aaggcacttt taacatcata    2760
gccacagaaa tcaagtgcca gtctatctgg aatccatgtt gtattgcaga taatgttctc    2820 attattttt gatgtagaat ttacattgcc atgggtgtta aataagcttt gagtcaaaag    2880
tcaagaaagt gactgaatat acagtcacct tttatgaaat gagtctctgt gttactgggt    2940
ggcatgactg attgaggtga agctcacggg gccaggctga ccgtcttgac cgttccactt    3000
gagataggtt ggtcatcgtg cagaaggccc caggacctca gcacacacag cctcctcttg    3060
gtctgagtag gcatcatgtg ggggccagat ctgcctgctg ttttccatggg ttacatttac    3120 tgtgctgtat ctcagatgtt ggtgtctgga agtttattct aaagactg ctacccagct    3180 ggtctgtatt attggaagtt gcagttcgtg ctttggttgg ccttctggtc taaagctgtg    3240
tcctgaatat tagggatcac aattcactga aatacagcag tgtgtggagg tgatggccag    3300
ttaatctgct gaactggttt tgactaatga caaacctctt tttaagatgg tagaatggag    3360
gtgatagtca caaagtaaa tgttccattt ttatgaatga cttctacag agtttctatt    3420 tctaaagaaa aaacaattgt tcacatccca tctgatgatt agcatgtgtg taatgaatgc    3480
tgtcttggtc tcccctgtgg aaaccttct ccctgtgcct tagagcaggt gtgtacatct    3540
ctcactacct ttctcatggg tgctgttaga ttttggcacc cgtttctca gcattcagcc    3600 cagggaatgt ggttttcact tcttcgtcag ataagaccaa catgaagggg tatgttgaga    3660
aacatcctga ggcaaggtgg gaggtgggat ggggcaggac tttcccttcc aagcacatgc    3720
atggcaggtg gggaaagggg ggcttgcacc cctgctggaa agaaaaggtt tgtgtatatt    3780
tctgatgcaa atgtccatact cactgctctg taaaggcagc tggcagcttt ttgggaaaag    3840
aacgtgctcg tctgttctct ggcatcaagt ttcttgcagc tgctctgagg gagagacagt    3900
gagctgcaag actgcctccc cataacaaca ggcaactcag agaagagtca ttttatgttg    3960
ttcctatgga atctggaatg agtgcagagc tcctacccac acatgactgc cccgccattt    4020
catcctaggc attctgtgaa ggagattggt tagtccaaac ttgctaacat acgaaaattc    4080
acttggaaca tgatgagaga tttcttattg aggccaagag atgtttcctg tcccagagga    4140
accattagga gtcgctttta gggtattcag ctttgttcat gaaataaggc atctctgaga    4200
aagtggcccc agggagagaa tggaggactg ggaggagaag cattaactga gctccaaggg    4260
tgtgtgggca gagagcttgc tatgtgaact cactccttaa gaaaatggaa gagaaaaaga    4320
gagtgctagt taaaaaatcg ggatgttta gtttggattt agggttttga tacttatgtt    4380
gaaatactaa tgtttctgat caataaaatc aaactcttaa tataccgagt aatgaaacca    4440
```

```
tagtgtgatt gcctcagaat aaattgagaa gtccaacttc ctagttttgt ttaattagtt    4500
tcactttttc tactctcccc agtatgctag aaatgggaat cgttgccctg cagattacgg    4560
caaaacatct gttttaagca aagctgcatt ttttgactca gaaattgtcc cagacggtgg    4620
atataagatg aaattcagaa aaacgttctg ccaagtcaca ggcttttaga tattatggaa    4680
acaagaaatg gaaaacagga tgatctccat gagaggcctt gatcctgaga gtaaaaggct    4740
tgtgtagata ggttagacaa cgtcctctag aaaagagacc agggataagt ccaggtttcc    4800
aggaaaacca agaagcctgc gggtagctga aggtagagtg ctagttgttc atcttaactt    4860
accaatgagc tacagaaagg acttagcatc tgatgtcatc agctttgcca ggagagtgat    4920
caaggaggtt aaagctcagg taaggtgtg ccttctcaga gattggctac aagcaacaga    4980
gaccacctca acagagacca cctcaacaga ctcagcccag ccatacaagg tgccaaagct    5040
cctccagagg gctgtcttgg gcctttgagg caattgatct ccagaaagag tcagaagtca    5100
ttccagtcca ggcccaggta ttcagatggt gacccagcca gataatagta tcttgagcaa    5160
ataatagtat cttgagtgca aataagcagg aagactgtcc ttcaaaaaat gtggggttac    5220
atgattttca gagccttttt ttcagagttg agcatctttt cttttaaaag aaataagggg    5280
caagaggacc aattttattc cttgaggaaa aatgacacac ccttctccca aaagaaagaa    5340
aactctctgg ccccccaact tcaacactaa tttggctccc tgaagaagag agaaaatatt    5400
atttctgtct ttattgaaga gaaatgggca atgccaatgt gaaggttact agtctttttt    5460
attttctatt ggtgaagact actactgctc ttatttagca gatcttatac cttcagtggt    5520
caccagtata gcaggtgagg tataaggaaa acagcagtgt gatgataaat ggtaattaat    5580
atactttgtc tgtgtcagca atagggaatg gtggggactg tggcaaactg aagcgcccct    5640
gttccaccca cagtgggtaa ttttccagtc gactgtggcc atgaagtact tcctgatctt    5700
cccattttc aagaaaagct gacaatctgg attttatat gaaaaattct gattttaaaa    5760
aatattggca actaagttaa aattcaagtg aatttagacc cagcagaaga catggatgga    5820
cctgatttgg tccactgact accagtttgt taacctgtgc tttataagat ttgaaggaaa    5880
ggcattcatg gtaattacag acggtgccac cagaaaatgc tcttgctaaa tgcagccagt    5940
agttagattg cttctttctc cagtctcccc cgcaaagaaa tttgacgtga ttctgaatgc    6000
actggacatg tcttgattgc gtcttacat ttcacagtgt cttaaaagaa aggcaagcca    6060
gttgttaatt tcagaatcag atttatgctc tctcaattta aaaaatgctg ggaacaattt    6120
catttttttt tttttgagat ggagtcttgc tctgttgccc aggctggagt gcagtggcgt    6180
gatctcggct cactgcaagc tccacctccc gggttcacgc cattctcctg cctcagcctc    6240
ctgagtagct gggactacag gcgcccacca ccacgcctgg ctaatttttt tgtattttta    6300
gtagagacgg ggtttcactg tgttagccag gatgatctcg atctcctgac ctggtgatcc    6360
gcttgcctcg gcctcccaaa gtgctgggat tacaggcgtg agccactgcg cccggcctaa    6420
caatttcatt taaactccac aacctaaagg gctttgttta tagttttagc tcttggcata    6480
atttttttca ggtggtgtgc aattctgagc ataggccaag acatgattag gaaagcaggc    6540
agttgtagag agtaaggcaa ggaacctcct agcgtccatt agagccaggt atttgcatta    6600
tcttccgttt taagtggtct gtgaattgac tgtgttttgg aggtgtgaaa cagtatacag    6660
agaaaagctt ttcctgatac tgagatatca gttaggagtc caaatggggt gttgggtcat    6720
ccttgccata tcacctcctt tccaggctca gagtgaaaat agacaaaagg aaatctgact    6780
gcaagccagt ggctttgatt ccagtttcag agtttaggga ctaggagaga gtttagatta    6840
```

```
tctagcatat tctcccctg gtgtcagaca gggctgtgcc tgaattattc cagacatatg      6900
gctgtagatg gtattcttta ttttataaga aggagattct gtaacctacc ctgctgatca      6960
gatagttctt tgtatgtctt agagaaattc aagccagctt cctttgttc ggcttgtagt       7020
ggagaaagaa cagctggtca ccttccatgt attcaaaaac cacagtgaag tcatccccct      7080
ggtgttttta tttcagtgat aaataattcc acccacttaa accattcttc atggctcttg      7140
ttttccaggg gcctaataat tttcactgct gtaatgtttc tcagcttcac acttagttta      7200
gttgcccaaa caatgttggt gccttactca cattggtgcc ttgtgaagac gaggctcagg      7260
atggggatta tggggaaatt cttgcacacc cagctcctct taccacttaa aaatataatg      7320
gcactttcac aaaatgatat gtcacctata ttcattgaga attatttgac tgccacattt      7380
ttcccctgat gatagtcatc tatcataact tgtgtttgtt ttcctcctga gatcaaacac      7440
ttggtgctta ttcctgatgt atactctgag accagctctt accttctgag tggcagctac      7500
ccctccctcc caattttaga tcctatttt acacatctct atagatatca cctttatttc       7560
atgactcaca atattaaatg gtacagactt cagtttaacc actggtgtgg taacagcagt      7620
agttgctaag taccaccttc ccattgctgt tgagggcta atttgcaaag acatttgaat       7680
ctcccagtga agatgtctgg ggaattttgg ccagttgtct tccctcttgc ccttttgttc      7740
tttaaaattc agcttggacc atagacacct ccaggatctt gtttatgttc tgctctcaat      7800
tgaccaagca ctgcgttttg cacaatcaga agtctcacaa aagcaaacag ttatgactgc      7860
atatctgatg tttatatcct ataaaatttc aggaagattc agagtcaatc ttctatttgt      7920
acatgatgta gacaaaatta gctgctccaa ttgttagaca aaaaattgcc attggattac      7980
actaatgtgc tcatctgttg tttttaaagt ttggtatcag gcggggcacg gtggctcacg      8040
cctgtaatcc cagcattttg ggaggccaag gtgggcggat cacctgaggt ccagagttca      8100
agaccagcct gaccaacatg gtgaaaccct gtctctacta aaaatacaaa attaatcagg      8160
cgtggttgtg tgtgcctgta atcccagcta ctcgagaggc tgaggcagga gaatcgcttg      8220
aatccgggag gcagaggttg cagtgagctg agatcacgcc attgcactct agcctgggca      8280
acaagagcga aactccgtct caacaacaac aacaaaaagt tggtatgtt tctctcaaga       8340
aaaaagcatg gtgagtccag acagcagcaa aagcttttgt gaaaaccaat tgtgttcatc      8400
tagatagtaa gtaactccta tttttactgt taattttta aaagagaatt tttccctgtg       8460
gaaactccct gttagtacgt cctaggggag aaagcctgtg gaatatggtg gttattgatg      8520
gcgttgcctt tgtttcatct ttgagtttgc cctttgtggg atctagtggg ataatgagca      8580
ctgacagaac tcttaacagc gtgctgtatt tttgacattg aaaatgttaa tgacttgatt      8640
tgtacataac tctgtaacta ggtgaaagta gatcacagct gacatttaca aaatgttttt      8700
gtaccttaga atttctgcat taaataaaat gttttgtttt aa                         8742
```

<210> SEQ ID NO 26
<211> LENGTH: 707
<212> TYPE: PRT
<213> ORGANISM: Homo sapiens

<400> SEQUENCE: 26

Met Asp Tyr Arg Gln Ser Trp Pro Trp Gln Gly Val Gly Pro Ala Ser
1               5                   10                  15

Arg Asn Ser Gly Leu Tyr Asn Ile Thr Phe Lys Tyr Asp Asn Cys Thr
            20                  25                  30

```
Thr Tyr Leu Asn Pro Val Gly Lys His Val Ile Ala Asp Ala Gln Asn
            35                  40                  45
Ile Thr Ile Ser Gln Tyr Ala Cys His Asp Gln Val Ala Val Thr Ile
 50                  55                  60
Leu Trp Ser Pro Gly Ala Leu Gly Ile Glu Phe Leu Lys Gly Phe Arg
 65                  70                  75                  80
Val Ile Leu Glu Glu Leu Lys Ser Glu Gly Arg Gln Cys Gln Gln Leu
                 85                  90                  95
Ile Leu Lys Asp Pro Lys Gln Leu Asn Ser Ser Phe Lys Arg Thr Gly
                100                 105                 110
Met Glu Ser Gln Pro Phe Leu Asn Met Lys Phe Glu Thr Asp Tyr Phe
            115                 120                 125
Val Lys Val Val Pro Phe Pro Ser Ile Lys Asn Glu Ser Asn Tyr His
            130                 135                 140
Pro Phe Phe Phe Arg Thr Arg Ala Cys Asp Leu Leu Leu Gln Pro Asp
145                 150                 155                 160
Asn Leu Ala Cys Lys Pro Phe Trp Lys Pro Arg Asn Leu Asn Ile Ser
                165                 170                 175
Gln His Gly Ser Asp Met Gln Val Ser Phe Asp His Ala Pro His Asn
            180                 185                 190
Phe Gly Phe Arg Phe Phe Tyr Leu His Tyr Lys Leu Lys His Glu Gly
            195                 200                 205
Pro Phe Lys Arg Lys Thr Cys Lys Gln Glu Gln Thr Thr Glu Thr Thr
            210                 215                 220
Ser Cys Leu Leu Gln Asn Val Ser Pro Gly Asp Tyr Ile Ile Glu Leu
225                 230                 235                 240
Val Asp Asp Thr Asn Thr Thr Arg Lys Val Met His Tyr Ala Leu Lys
                245                 250                 255
Pro Val His Ser Pro Trp Ala Gly Pro Ile Arg Ala Val Ala Ile Thr
            260                 265                 270
Val Pro Leu Val Val Ile Ser Ala Phe Ala Thr Leu Phe Thr Val Met
            275                 280                 285
Cys Arg Lys Lys Gln Gln Glu Asn Ile Tyr Ser His Leu Asp Glu Glu
            290                 295                 300
Ser Ser Glu Ser Ser Thr Tyr Thr Ala Ala Leu Pro Arg Glu Arg Leu
305                 310                 315                 320
Arg Pro Arg Pro Lys Val Phe Leu Cys Tyr Ser Ser Lys Asp Gly Gln
                325                 330                 335
Asn His Met Asn Val Val Gln Cys Phe Ala Tyr Phe Leu Gln Asp Phe
            340                 345                 350
Cys Gly Cys Glu Val Ala Leu Asp Leu Trp Glu Asp Phe Ser Leu Cys
            355                 360                 365
Arg Glu Gly Gln Arg Glu Trp Val Ile Gln Lys Ile His Glu Ser Gln
            370                 375                 380
Phe Ile Ile Val Val Cys Ser Lys Gly Met Lys Tyr Phe Val Asp Lys
385                 390                 395                 400
Lys Asn Tyr Lys His Lys Gly Gly Arg Gly Ser Gly Lys Gly Glu
                405                 410                 415
Leu Phe Leu Val Ala Val Ser Ala Ile Ala Glu Lys Leu Arg Gln Ala
            420                 425                 430
Lys Gln Ser Ser Ser Ala Ala Leu Ser Lys Phe Ile Ala Val Tyr Phe
            435                 440                 445
Asp Tyr Ser Cys Glu Gly Asp Val Pro Gly Ile Leu Asp Leu Ser Thr
```

```
                450                 455                 460
Lys Tyr Arg Leu Met Asp Asn Leu Pro Gln Leu Cys Ser His Leu His
465                 470                 475                 480

Ser Arg Asp His Gly Leu Gln Glu Pro Gly Gln His Thr Arg Gln Gly
                485                 490                 495

Ser Arg Arg Asn Tyr Phe Arg Ser Lys Ser Gly Arg Ser Leu Tyr Val
                500                 505                 510

Ala Ile Cys Asn Met His Gln Phe Ile Asp Glu Pro Asp Trp Phe
            515                 520                 525

Glu Lys Gln Phe Val Pro Phe His Pro Pro Leu Arg Tyr Arg Glu
530                 535                 540

Pro Val Leu Glu Lys Phe Asp Ser Gly Leu Val Leu Asn Asp Val Met
545                 550                 555                 560

Cys Lys Pro Gly Pro Glu Ser Asp Phe Cys Leu Lys Val Glu Ala Ala
                565                 570                 575

Val Leu Gly Ala Thr Gly Pro Ala Asp Ser Gln His Glu Ser Gln His
            580                 585                 590

Gly Gly Leu Asp Gln Asp Gly Glu Ala Arg Pro Ala Leu Asp Gly Ser
            595                 600                 605

Ala Ala Leu Gln Pro Leu Leu His Thr Val Lys Ala Gly Ser Pro Ser
610                 615                 620

Asp Met Pro Arg Asp Ser Gly Ile Tyr Asp Ser Ser Val Pro Ser Ser
625                 630                 635                 640

Glu Leu Ser Leu Pro Leu Met Glu Gly Leu Ser Thr Asp Gln Thr Glu
                645                 650                 655

Thr Ser Ser Leu Thr Glu Ser Val Ser Ser Ser Gly Leu Gly Glu
            660                 665                 670

Glu Glu Pro Pro Ala Leu Pro Ser Lys Leu Leu Ser Ser Gly Ser Cys
                675                 680                 685

Lys Ala Asp Leu Gly Cys Arg Ser Tyr Thr Asp Glu Leu His Ala Val
            690                 695                 700

Ala Pro Leu
705

<210> SEQ ID NO 27
<211> LENGTH: 2717
<212> TYPE: DNA
<213> ORGANISM: Homo sapiens

<400> SEQUENCE: 27
cgagggctcc tgctggtact gtgttcgctg ctgcacagca aggccctgcc acccaccttc      60
aggccatgca gccatgttcc gggagcccta attgcacaga agcccatggg gagctccaga     120
ctggcagccc tgctcctgcc tctcctcctc atagtcatcg acctctctga ctctgctggg     180
attggctttc gccacctgcc ccactggaac acccgctgtc ctctggcctc ccacacggat     240
gacagtttca ctggaagttc tgcctatatc ccttgccgca cctggtgggc cctcttctcc     300
acaaagcctt ggtgtgtgcg agtctggcac tgttcccgct gtttgtgcca gcatctgctg     360
tcaggtggct caggtcttca cggggcctc ttccacctcc tggtgcagaa atccaaaaag     420
tcttccacat tcaagttcta taggagacac aagatgccag cacctgctca gaggaagctg     480
ctgcctcgtc gtcacctgtc tgagaagagc catcacattt ccatcccctc cccagacatc     540
tcccacaagg gacttcgctc taaaaggacc caaccttcgg atccagagac atgggaaagt     600
cttcccagat ggactcaca aaggcatgga ggacccgagt tctcctttga tttgctgcct     660
```

```
gaggcccggg ctattcgggt gaccatatct tcaggccctg aggtcagcgt gcgtctttgt    720
caccagtggg cactggagtg tgaagagctg agcagtccct atgatgtcca gaaaattgtg    780
tctgggggcc acactgtaga gctgccttat gaattccttc tgccctgtct gtgcatagag    840
gcatcctacc tgcaagagga cactgtgagg cgcaaaaaat gtcccttcca gagctggcca    900
gaagcctatg gctcggactt ctggaagtca gtgcacttca ctgactacag ccagcacact    960
cagatggtca tggccctgac actccgctgc ccactgaagc tggaagctgc cctctgccag   1020
aggcacgact ggcatacccT ttgcaaagac ctcccgaatg ccacagctcg agagtcagat   1080
gggtggtatg ttttggagaa ggtggacctg cacccccagc tctgcttcaa gttctctttt   1140
ggaaacagca gccatgttga atgccccac cagactgggt ctctcacatc ctggaatgta   1200
agcatggata cccaagccca gcagctgatt cttcacttct cctcaagaat gcatgccacc   1260
ttcagtgctg cctggagcct cccaggcttg gggcaggaca cttTggtgcc ccccgtgtac   1320
actgtcagcc aggcccgggg ctcaagccca gtgtcactag acctcatcat tcccttcctg   1380
aggccagggt gctgtgtcct ggtgtggcgg tcagatgtcc agtttgcctg gaagcacctc   1440
ttgtgtccgg atgtctctta cagacacctg ggctcttga tcctggcact gctgccctc    1500 ctcaccctac tgggtgttgt tctggccctc acctgccggc gcccacagtc aggcccgggc   1560
ccagcgcggc cagtgctcct cctgcacgcg cggactcgg aggcgcagcg cgcctggtg    1620 ggagcgctgg ctgaactgct acgggcagcg ctgggcggcg ggcgcgacgt gatcgtggac   1680
ctgtgggagg ggaggcacgt ggcgcgcgtg ggcccgctgc cgtggctctg gcggcgcgg    1740 acgcgcgtag cgcgggagca gggcactgtg ctgctgctgt ggagcggcgc cgaccttcgc   1800
ccggtcagcg gccccgaccc ccgcgccgcg ccctgctcg ccctgctcca cgctgccccg    1860
cgcccgctgc tgctgctcgc ttacttcagt cgcctctgcg ccaagggcga catcccccg    1920 ccgctgcgcg ccctgccgcg ctaccgcctg ctgcgcgacc tgccgcgtct gctgcgggcg   1980
ctggacgcgc ggccttttcgc agaggccacc agctggggcc gccttgggc gcggcagcgc   2040 aggcagagcc gcctagagct gtgcagccgg ctcgaacgag aggccgcccg acttgcagac   2100
ctaggttgag cagagctcca ccgcagtccc gggtgtctgc ggccgcaacg caacggacac   2160
tggctggaac cccggaatga gccttcgacc ctgaaatcct tggggtgcct cgaggacgac   2220
tggccgaaaa gccgcattcc ctgcctcaca ggccggaagt cccagcccag tccccgcgcg   2280
cgtccctctt cctcctcata ctttcccttg actgagagct cctctaaccc ctgttctgat   2340
gggggagggc ggtcttccca cttcctctcc agaactccag aaagagcagt gtgcttatgc   2400
ttcagtccag gctggagagg ttggggccgg ggtagggagg caggagccat gtcagttctg   2460
aaggagggtg aggcggtggg ggattgcagg gggcggctga gagaaaacct ccttgggggc   2520
cagggattcc ctttcccact ctgaggctct ggccagaggg agagaggact ctggacctag   2580
gaaaagaggc ttttggctcc aggtggtcag gacagtgggg gttggggtg gggtgggtgg    2640 gtgctggcgg tggggaccaa gatccggaaa gatgaataaa gacaaacatg acaaactaag   2700
aaaaaaaaaa aaaaaaa                                                   2717
```

<210> SEQ ID NO 28
<211> LENGTH: 666
<212> TYPE: PRT
<213> ORGANISM: Homo sapiens

<400> SEQUENCE: 28

```
Met Gly Ser Ser Arg Leu Ala Ala Leu Leu Pro Leu Leu Leu Ile
 1               5                  10                  15

Val Ile Asp Leu Ser Asp Ser Ala Gly Ile Gly Phe Arg His Leu Pro
             20                  25                  30

His Trp Asn Thr Arg Cys Pro Leu Ala Ser His Thr Asp Asp Ser Phe
             35                  40                  45

Thr Gly Ser Ser Ala Tyr Ile Pro Cys Arg Thr Trp Trp Ala Leu Phe
    50                  55                  60

Ser Thr Lys Pro Trp Cys Val Arg Val Trp His Cys Ser Arg Cys Leu
65                  70                  75                  80

Cys Gln His Leu Leu Ser Gly Ser Gly Leu Gln Arg Gly Leu Phe
                85                  90                  95

His Leu Leu Val Gln Lys Ser Lys Ser Ser Thr Phe Lys Phe Tyr
            100                 105                 110

Arg Arg His Lys Met Pro Ala Pro Ala Gln Arg Lys Leu Leu Pro Arg
            115                 120                 125

Arg His Leu Ser Glu Lys Ser His His Ile Ser Ile Pro Ser Pro Asp
            130                 135                 140

Ile Ser His Lys Gly Leu Arg Ser Lys Arg Thr Gln Pro Ser Asp Pro
145                 150                 155                 160

Glu Thr Trp Glu Ser Leu Pro Arg Leu Asp Ser Gln Arg His Gly Gly
                165                 170                 175

Pro Glu Phe Ser Phe Asp Leu Leu Pro Glu Ala Arg Ala Ile Arg Val
                180                 185                 190

Thr Ile Ser Ser Gly Pro Glu Val Ser Val Arg Leu Cys His Gln Trp
            195                 200                 205

Ala Leu Glu Cys Glu Glu Leu Ser Ser Pro Tyr Asp Val Gln Lys Ile
            210                 215                 220

Val Ser Gly Gly His Thr Val Glu Leu Pro Tyr Glu Phe Leu Leu Pro
225                 230                 235                 240

Cys Leu Cys Ile Glu Ala Ser Tyr Leu Gln Glu Asp Thr Val Arg Arg
                245                 250                 255

Lys Lys Cys Pro Phe Gln Ser Trp Pro Glu Ala Tyr Gly Ser Asp Phe
            260                 265                 270

Trp Lys Ser Val His Phe Thr Asp Tyr Ser Gln His Thr Gln Met Val
        275                 280                 285

Met Ala Leu Thr Leu Arg Cys Pro Leu Lys Leu Glu Ala Ala Leu Cys
    290                 295                 300

Gln Arg His Asp Trp His Thr Leu Cys Lys Asp Leu Pro Asn Ala Thr
305                 310                 315                 320

Ala Arg Glu Ser Asp Gly Trp Tyr Val Leu Glu Lys Val Asp Leu His
                325                 330                 335

Pro Gln Leu Cys Phe Lys Phe Ser Phe Gly Asn Ser Ser His Val Glu
            340                 345                 350

Cys Pro His Gln Thr Gly Ser Leu Thr Ser Trp Asn Val Ser Met Asp
            355                 360                 365

Thr Gln Ala Gln Gln Leu Ile Leu His Phe Ser Ser Arg Met His Ala
    370                 375                 380

Thr Phe Ser Ala Ala Trp Ser Leu Pro Gly Leu Gly Gln Asp Thr Leu
385                 390                 395                 400

Val Pro Pro Val Tyr Thr Val Ser Gln Ala Arg Gly Ser Ser Pro Val
                405                 410                 415

Ser Leu Asp Leu Ile Ile Pro Phe Leu Arg Pro Gly Cys Cys Val Leu
```

```
                420              425              430
Val Trp Arg Ser Asp Val Gln Phe Ala Trp Lys His Leu Leu Cys Pro
            435              440              445

Asp Val Ser Tyr Arg His Leu Gly Leu Leu Ile Leu Ala Leu Leu Ala
        450              455              460

Leu Leu Thr Leu Leu Gly Val Val Leu Ala Leu Thr Cys Arg Arg Pro
465              470              475              480

Gln Ser Gly Pro Gly Pro Ala Arg Pro Val Leu Leu Leu His Ala Ala
                485              490              495

Asp Ser Glu Ala Gln Arg Arg Leu Val Gly Ala Leu Ala Glu Leu Leu
            500              505              510

Arg Ala Ala Leu Gly Gly Gly Arg Asp Val Ile Val Asp Leu Trp Glu
        515              520              525

Gly Arg His Val Ala Arg Val Gly Pro Leu Pro Trp Leu Trp Ala Ala
    530              535              540

Arg Thr Arg Val Ala Arg Glu Gln Gly Thr Val Leu Leu Leu Trp Ser
545              550              555              560

Gly Ala Asp Leu Arg Pro Ser Gly Pro Asp Pro Arg Ala Ala Pro Leu
                565              570              575

Leu Ala Leu Leu His Ala Ala Pro Arg Pro Leu Leu Leu Leu Ala Tyr
            580              585              590

Phe Ser Arg Leu Cys Ala Lys Gly Asp Ile Pro Pro Pro Leu Arg Ala
        595              600              605

Leu Pro Arg Tyr Arg Leu Leu Arg Asp Leu Pro Arg Leu Leu Arg Ala
    610              615              620

Leu Asp Ala Arg Pro Phe Ala Glu Ala Thr Ser Trp Gly Arg Leu Gly
625              630              635              640

Ala Arg Gln Arg Gln Ser Arg Leu Glu Leu Cys Ser Arg Leu Glu
                645              650              655

Arg Glu Ala Ala Arg Leu Ala Asp Leu Gly
            660              665

<210> SEQ ID NO 29
<211> LENGTH: 2581
<212> TYPE: DNA
<213> ORGANISM: Homo sapiens

<400> SEQUENCE: 29
cgagggctcc tgctggtact gtgttcgctg ctgcacagca aggccctgcc acccaccttc      60
aggccatgca gccatgttcc gggagcccta attgcacaga gcccatggga gagctccaga     120
ctggcagccc tgctcctgcc tctcctcctc atagtcatcg acctctctga ctctgctggg     180
attggctttc gccacctgcc ccactggaac acccgctgtc ctctggcctc ccacacggtc     240
ttcaacgggg cctcttccac ctcctggtgc agaaatccaa aaagtcttcc acattcaagt     300
tctataggag acacaagatg ccagcacctg ctcagaggaa gctgctgcct cgtcgtcacc     360
tgtctgagaa gagccatcac atttccatcc cctccccaga catctcccac aagggacttc     420
gctctaaaag gacccaacct tcggatccag agacatggga agtcttccc agattggact      480 cacaaaggca tggaggaccc gagttctcct ttgatttgct gcctgaggcc cgggctattc     540
gggtgaccat atcttcaggc ctgaggtca gcgtgcgtct tgtcaccag tgggcactgg        600 agtgtgaaga gctgagcagt ccctatgatg tccagaaaat tgtgtctggg ggccacactg     660
tagagctgcc ttatgaattc cttctgccct gtctgtgcat agaggcatcc tacctgcaag     720
```

```
aggacactgt gaggcgcaaa aaatgtccct tccagagctg gccagaagcc tatggctcgg    780
acttctggaa gtcagtgcac ttcactgact acagccagca cactcagatg gtcatggccc    840
tgacactccg ctgcccactg aagctggaag ctgccctctg ccagaggcac gactggcata    900
cccttttgcaa agacctcccg aatgccacag ctcgagagtc agatgggtgg tatgttttgg    960
agaaggtgga cctgcacccc cagctctgct tcaagttctc ttttggaaac agcagccatg   1020
ttgaatgccc ccaccagact gggtctctca tcctggaa tgtaagcatg gatacccaag     1080
cccagcagct gattcttcac ttctcctcaa gaatgcatgc accttcagt gctgcctgga    1140
gcctcccagg cttggggcag gacactttgg tgcccccgt gtacactgtc agccaggccc    1200
ggggctcaag cccagtgtca ctagacctca tcattcccctt cctgaggcca gggtgctgtg   1260
tcctggtgtg gcggtcagat gtccagtttg cctggaagca cctcttgtgt ccggatgtct   1320
cttacagaca cctggggctc ttgatcctgg cactgctggc cctcctcacc ctactgggtg   1380
ttgttctggc cctcacctgc cggcgcccac agtcaggccc gggcccagcg cggccagtgc   1440
tcctcctgca cgcggcggac tcggaggcgc agcggcgcct ggtgggagcg ctggctgaac   1500
tgctacgggc agcgctgggc ggcgggcgcg acgtgatcgt ggacctgtgg gaggggaggc   1560
acgtggcgcg cgtgggcccg ctgccgtggc tctgggcggc gcggacgcgc gtagcgcggg   1620
agcagggcac tgtgctgctg ctgtggagcg gcgccgacct tcgcccggtc agcggccccg   1680
accccccgcg cgcgcccctg ctcgcccctgc tccacgctgc cccgcgcccg ctgctgctgc   1740
tcgcttactt cagtcgcctc tgcgccaagg gcgacatccc ccgccgctg cgcgccctgc    1800
cgcgctaccg cctgctgcgc gacctgccgc gtctgctgcg ggcgctggac gcgcggcctt   1860
tcgcagaggc caccagctgg ggccgccttg ggcgcggca gcgcaggcag agccgcctag    1920
agctgtgcag ccggctcgaa cgagaggccg cccgacttgc agacctaggt tgagcagagc   1980
tccaccgcag tcccgggtgt ctgcggccgc aacgcaacgg acactggctg aacccccgga   2040
atgagccttc gaccctgaaa tccttggggt gcctcgagga cgactggccg aaaagccgca   2100
ttccctgcct cacaggccgg aagtcccagc ccagtccccg cgcgcgtccc tcttcctcct   2160
catactttcc cttgactgag agctcctcta accccctgttc tgatggggga gggcggtctt   2220
cccacttcct ctccagaact ccagaaagag cagtgtgctt atgcttcagt ccaggctgga   2280
gaggttgggg ccggggtagg gaggcaggag ccatgtcagt tctgaaggag ggtgaggcgg   2340
tgggggattg caggggggcgg ctgagagaaa acctccttgg gggccaggga ttccctttcc   2400
cactctgagg ctctggccag agggagagag gactctggac ctaggaaaag aggcttttgg   2460
ctccaggtgg tcaggacagt gggggttggg ggtggggtgg gtgggtgctg gcggtgggga   2520
ccaagatccg gaaagatgaa taaagacaaa catgacaaac taagaaaaaa aaaaaaaaa    2580
a                                                                   2581

<210> SEQ ID NO 30
<211> LENGTH: 551
<212> TYPE: PRT
<213> ORGANISM: Homo sapiens

<400> SEQUENCE: 30

Met Pro Ala Pro Ala Gln Arg Lys Leu Leu Pro Arg Arg His Leu Ser
1               5                   10                  15

Glu Lys Ser His His Ile Ser Ile Pro Ser Pro Asp Ile Ser His Lys
            20                  25                  30

Gly Leu Arg Ser Lys Arg Thr Gln Pro Ser Asp Pro Glu Thr Trp Glu
```

-continued

```
                35                  40                  45
Ser Leu Pro Arg Leu Asp Ser Gln Arg His Gly Gly Pro Glu Phe Ser
 50                  55                  60

Phe Asp Leu Leu Pro Glu Ala Arg Ala Ile Arg Val Thr Ile Ser Ser
 65                  70                  75                  80

Gly Pro Glu Val Ser Val Arg Leu Cys His Gln Trp Ala Leu Glu Cys
                 85                  90                  95

Glu Glu Leu Ser Ser Pro Tyr Asp Val Gln Lys Ile Val Ser Gly Gly
            100                 105                 110

His Thr Val Glu Leu Pro Tyr Glu Phe Leu Leu Pro Cys Leu Cys Ile
        115                 120                 125

Glu Ala Ser Tyr Leu Gln Glu Asp Thr Val Arg Arg Lys Lys Cys Pro
    130                 135                 140

Phe Gln Ser Trp Pro Glu Ala Tyr Gly Ser Asp Phe Trp Lys Ser Val
145                 150                 155                 160

His Phe Thr Asp Tyr Ser Gln His Thr Gln Met Val Met Ala Leu Thr
                165                 170                 175

Leu Arg Cys Pro Leu Lys Leu Glu Ala Ala Leu Cys Gln Arg His Asp
            180                 185                 190

Trp His Thr Leu Cys Lys Asp Leu Pro Asn Ala Thr Ala Arg Glu Ser
        195                 200                 205

Asp Gly Trp Tyr Val Leu Glu Lys Val Asp Leu His Pro Gln Leu Cys
    210                 215                 220

Phe Lys Phe Ser Phe Gly Asn Ser Ser His Val Glu Cys Pro His Gln
225                 230                 235                 240

Thr Gly Ser Leu Thr Ser Trp Asn Val Ser Met Asp Thr Gln Ala Gln
                245                 250                 255

Gln Leu Ile Leu His Phe Ser Ser Arg Met His Ala Thr Phe Ser Ala
            260                 265                 270

Ala Trp Ser Leu Pro Gly Leu Gly Gln Asp Thr Leu Val Pro Pro Val
        275                 280                 285

Tyr Thr Val Ser Gln Ala Arg Gly Ser Ser Pro Val Ser Leu Asp Leu
    290                 295                 300

Ile Ile Pro Phe Leu Arg Pro Gly Cys Cys Val Leu Val Trp Arg Ser
305                 310                 315                 320

Asp Val Gln Phe Ala Trp Lys His Leu Leu Cys Pro Asp Val Ser Tyr
                325                 330                 335

Arg His Leu Gly Leu Leu Ile Leu Ala Leu Ala Leu Leu Thr Leu
            340                 345                 350

Leu Gly Val Val Leu Ala Leu Thr Cys Arg Arg Pro Gln Ser Gly Pro
        355                 360                 365

Gly Pro Ala Arg Pro Val Leu Leu His Ala Ala Asp Ser Glu Ala
    370                 375                 380

Gln Arg Arg Leu Val Gly Ala Leu Ala Glu Leu Leu Arg Ala Ala Leu
385                 390                 395                 400

Gly Gly Gly Arg Asp Val Ile Val Asp Leu Trp Glu Gly Arg His Val
                405                 410                 415

Ala Arg Val Gly Pro Leu Pro Trp Leu Trp Ala Ala Arg Thr Arg Val
            420                 425                 430

Ala Arg Glu Gln Gly Thr Val Leu Leu Leu Trp Ser Gly Ala Asp Leu
        435                 440                 445

Arg Pro Val Ser Gly Pro Asp Pro Arg Ala Ala Pro Leu Leu Ala Leu
    450                 455                 460
```

```
Leu His Ala Ala Pro Arg Pro Leu Leu Leu Ala Tyr Phe Ser Arg
465                 470                 475                 480

Leu Cys Ala Lys Gly Asp Ile Pro Pro Leu Arg Ala Leu Pro Arg
            485                 490                 495

Tyr Arg Leu Leu Arg Asp Leu Pro Arg Leu Leu Arg Ala Leu Asp Ala
        500                 505                 510

Arg Pro Phe Ala Glu Ala Thr Ser Trp Gly Arg Leu Gly Ala Arg Gln
        515                 520                 525

Arg Arg Gln Ser Arg Leu Glu Leu Cys Ser Arg Leu Glu Arg Glu Ala
        530                 535                 540

Ala Arg Leu Ala Asp Leu Gly
545                 550

<210> SEQ ID NO 31
<211> LENGTH: 2729
<212> TYPE: DNA
<213> ORGANISM: Homo sapiens

<400> SEQUENCE: 31
```

| | | | | | |
|---|---|---|---|---|---|
| ggtgcgtccc | ccaacctgat | gctagcccct | ttcctgttac | ttctcaccca | cagcaggagc | 60 |
| cccttgtctt | tcaggccatg | cagccatgtt | ccgggagccc | taattgcaca | gaagcccatg | 120 |
| gggagctcca | gactggcagc | cctgctcctg | cctctcctcc | tcatagtcat | cgacctctct | 180 |
| gactctgctg | ggattggctt | tcgccacctg | ccccactgga | acacccgctg | tcctctggcc | 240 |
| tcccacacgg | atgacagttt | cactggaagt | tctgcctata | tcccttgccg | cacctggtgg | 300 |
| gccctcttct | ccacaaagcc | ttggtgtgtg | cgagtctggc | actgttcccg | ctgtttgtgc | 360 |
| cagcatctgc | tgtcaggtgg | ctcaggtctt | aacggggcc | tcttccacct | cctggtgcag | 420 |
| aaatccaaaa | agtcttccac | attcaagttc | tataggagac | acaagatgcc | agcacctgct | 480 |
| cagaggaagc | tgctgcctcg | tcgtcacctg | tctgagaaga | gccatcacat | tccatcccc | 540 |
| tccccagaca | tctcccacaa | gggacttcgc | tctaaaagga | cccaaccttc | ggatccagag | 600 |
| acatgggaaa | gtcttcccag | attggactca | caaaggcatg | gaggacccga | gttctccttt | 660 |
| gatttgctgc | ctgaggcccg | ggctattcgg | gtgaccatat | cttcaggccc | tgaggtcagc | 720 |
| gtgcgtcttt | gtcaccagtg | ggcactggag | tgtgaagagc | tgagcagtcc | ctatgatgtc | 780 |
| cagaaaattg | tgtctggggg | ccacactgta | gagctgcctt | atgaattcct | tctgccctgt | 840 |
| ctgtgcatag | aggcatccta | cctgcaagag | gacactgtga | ggcgcaaaaa | atgtcccttc | 900 |
| cagagctggc | cagaagccta | tggctcggac | ttctggaagt | cagtgcactt | cactgactac | 960 |
| agccagcaca | ctcagatggt | catggccctg | acactccgct | gcccactgaa | gctggaagct | 1020 |
| gccctctgcc | agaggcacga | ctggcatacc | ctttgcaaag | acctcccgaa | tgccacagct | 1080 |
| cgagagtcag | atgggtggta | tgttttggag | aaggtggacc | tgcaccccca | gctctgcttc | 1140 |
| aagttctctt | ttggaaacag | cagccatgtt | gaatgccccc | accagactgg | gtctctcaca | 1200 |
| tcctggaatg | taagcatgga | tacccaagcc | cagcagctga | ttcttcactt | ctcctcaaga | 1260 |
| atgcatgcca | ccttcagtgc | tgcctggagc | ctcccaggct | tggggcagga | cactttggtg | 1320 |
| cccccgtgt | acactgtcag | ccaggccgg | ggctcaagcc | cagtgtcact | agacctcatc | 1380 |
| attcccttcc | tgaggccagg | gtgctgtgtc | ctggtgtggc | ggtcagatgt | ccagtttgcc | 1440 |
| tggaagcacc | tcttgtgtcc | ggatgtctct | tacagacacc | tggggctctt | gatcctggca | 1500 |
| ctgctggccc | tcctcacccct | actgggtgtt | gttctggccc | tcacctgccg | gcgcccacag | 1560 |

-continued

```
tcaggcccgg gcccagcgcg gccagtgctc ctcctgcacg cggcggactc ggaggcgcag    1620
cggcgcctgg tgggagcgct ggctgaactg ctacgggcag cgctgggcgg cgggcgcgac    1680
gtgatcgtgg acctgtggga ggggaggcac gtggcgcgcg tgggcccgct gccgtggctc    1740
tgggcggcgc ggacgcgcgt agcgcgggag cagggcactg tgctgctgct gtggagcggc    1800
gccgaccttc gcccggtcag cggccccgac ccccgcgccg cgccctgct cgccctgctc    1860 cacgctgccc cgcgcccgct gctgctgctc gcttacttca gtcgcctctg cgccaagggc    1920
gacatccccc gccgctgcg cgccctgccg cgctaccgcc tgctgcgcga cctgccgcgt    1980
ctgctgcggg cgctggacgc gcggcctttc gcagaggcca ccagctgggg ccgccttggg    2040
gcgcggcagc gcaggcagag ccgcctagag ctgtgcagcc ggctcgaacg agaggccgcc    2100
cgacttgcag acctaggttg agcagagctc caccgcagtc ccgggtgtct gcggccgcaa    2160
cgcaacggac actggctgga accccggaat gagccttcga ccctgaaatc cttggggtgc    2220
ctcgaggacg actggccgaa aagccgcatt ccctgcctca caggccggaa gtcccagccc    2280
agtccccgcg cgcgtccctc ttcctcctca tactttccct tgactgagag ctcctctaac    2340
ccctgttctg atgggggagg gcggtcttcc cacttcctct ccagaactcc agaaagagca    2400
gtgtgcttat gcttcagtcc aggctggaga ggttggggcc ggggtaggga ggcaggagcc    2460
atgtcagttc tgaaggaggg tgaggcggtg ggggattgca gggggcggct gagagaaaac    2520
ctccttgggg gccagggatt ccctttccca ctctgaggct ctggccagag ggagagagga    2580
ctctggacct aggaaaagag gcttttggct ccaggtggtc aggacagtgg gggttggggg    2640
tggggtgggt gggtgctggc ggtggggacc aagatccgga aagatgaata aagacaaaca    2700
tgacaaacta agaaaaaaaa aaaaaaaaa                                      2729
```

<210> SEQ ID NO 32
<211> LENGTH: 667
<212> TYPE: PRT
<213> ORGANISM: Homo sapiens

<400> SEQUENCE: 32

```
Met Gly Ser Ser Arg Leu Ala Ala Leu Leu Pro Leu Leu Leu Ile
1               5                   10                  15

Val Ile Asp Leu Ser Asp Ser Ala Gly Ile Gly Phe Arg His Leu Pro
            20                  25                  30

His Trp Asn Thr Arg Cys Pro Leu Ala Ser His Thr Asp Asp Ser Phe
        35                  40                  45

Thr Gly Ser Ser Ala Tyr Ile Pro Cys Arg Thr Trp Trp Ala Leu Phe
    50                  55                  60

Ser Thr Lys Pro Trp Cys Val Arg Val Trp His Cys Ser Arg Cys Leu
65                  70                  75                  80

Cys Gln His Leu Leu Ser Gly Gly Ser Gly Leu Gln Arg Gly Leu Phe
                85                  90                  95

His Leu Leu Val Gln Lys Ser Lys Lys Ser Ser Thr Phe Lys Phe Tyr
            100                 105                 110

Arg Arg His Lys Met Pro Ala Pro Ala Gln Arg Lys Leu Leu Pro Arg
        115                 120                 125

Arg His Leu Ser Glu Lys His His Ile Ser Ile Pro Ser Pro Asp
    130                 135                 140

Ile Ser His Lys Gly Leu Arg Ser Lys Arg Thr Gln Pro Ser Asp Pro
145                 150                 155                 160

Glu Thr Trp Glu Ser Leu Pro Arg Leu Asp Ser Gln Arg His Gly Gly
```

```
            165                 170                 175
Pro Glu Phe Ser Phe Asp Leu Leu Pro Glu Ala Arg Ala Ile Arg Val
                180                 185                 190

Thr Ile Ser Ser Gly Pro Glu Val Ser Val Arg Leu Cys His Gln Trp
            195                 200                 205

Ala Leu Glu Cys Glu Glu Leu Ser Ser Pro Tyr Asp Val Gln Lys Ile
210                 215                 220

Val Ser Gly Gly His Thr Val Glu Leu Pro Tyr Glu Phe Leu Leu Pro
225                 230                 235                 240

Cys Leu Cys Ile Glu Ala Ser Tyr Leu Gln Glu Asp Thr Val Arg Arg
                245                 250                 255

Lys Lys Cys Pro Phe Gln Ser Trp Pro Glu Ala Tyr Gly Ser Asp Phe
                260                 265                 270

Trp Lys Ser Val His Phe Thr Asp Tyr Ser Gln His Thr Gln Met Val
                275                 280                 285

Met Ala Leu Thr Leu Arg Cys Pro Leu Lys Leu Glu Ala Ala Leu Cys
            290                 295                 300

Gln Arg His Asp Trp His Thr Leu Cys Lys Asp Leu Pro Asn Ala Thr
305                 310                 315                 320

Ala Arg Glu Ser Asp Gly Trp Tyr Val Leu Glu Lys Val Asp Leu His
                325                 330                 335

Pro Gln Leu Cys Phe Lys Phe Ser Phe Gly Asn Ser Ser His Val Glu
                340                 345                 350

Cys Pro His Gln Thr Gly Ser Leu Thr Ser Trp Asn Val Ser Met Asp
                355                 360                 365

Thr Gln Ala Gln Gln Leu Ile Leu His Phe Ser Ser Arg Met His Ala
            370                 375                 380

Thr Phe Ser Ala Ala Trp Ser Leu Pro Gly Leu Gly Gln Asp Thr Leu
385                 390                 395                 400

Val Pro Pro Val Tyr Thr Val Ser Gln Ala Arg Gly Ser Ser Pro Val
                405                 410                 415

Ser Leu Asp Leu Ile Ile Pro Phe Leu Arg Pro Gly Cys Cys Val Leu
                420                 425                 430

Val Trp Arg Ser Asp Val Gln Phe Ala Trp Lys His Leu Leu Cys Pro
            435                 440                 445

Asp Val Ser Tyr Arg His Leu Gly Leu Leu Ile Leu Ala Leu Leu Ala
            450                 455                 460

Leu Leu Thr Leu Leu Gly Val Val Leu Ala Leu Thr Cys Arg Arg Pro
465                 470                 475                 480

Gln Ser Gly Pro Gly Pro Ala Arg Pro Val Leu Leu Leu His Ala Ala
                485                 490                 495

Asp Ser Glu Ala Gln Arg Arg Leu Val Gly Ala Leu Ala Glu Leu Leu
            500                 505                 510

Arg Ala Ala Leu Gly Gly Gly Arg Asp Val Ile Val Asp Leu Trp Glu
            515                 520                 525

Gly Arg His Val Ala Arg Val Gly Pro Leu Pro Trp Leu Trp Ala Ala
            530                 535                 540

Arg Thr Arg Val Ala Arg Glu Gln Gly Thr Val Leu Leu Leu Trp Ser
545                 550                 555                 560

Gly Ala Asp Leu Arg Pro Val Ser Gly Pro Asp Pro Arg Ala Ala Pro
                565                 570                 575

Leu Leu Ala Leu Leu His Ala Ala Pro Arg Pro Leu Leu Leu Leu Ala
                580                 585                 590
```

-continued

```
Tyr Phe Ser Arg Leu Cys Ala Lys Gly Asp Ile Pro Pro Pro Leu Arg
        595                 600                 605

Ala Leu Pro Arg Tyr Arg Leu Leu Arg Asp Leu Pro Arg Leu Leu Arg
    610                 615                 620

Ala Leu Asp Ala Arg Pro Phe Ala Glu Ala Thr Ser Trp Gly Arg Leu
625                 630                 635                 640

Gly Ala Arg Gln Arg Arg Gln Ser Arg Leu Glu Leu Cys Ser Arg Leu
                645                 650                 655

Glu Arg Glu Ala Ala Arg Leu Ala Asp Leu Gly
            660                 665

<210> SEQ ID NO 33
<211> LENGTH: 18
<212> TYPE: RNA
<213> ORGANISM: Homo sapiens

<400> SEQUENCE: 33
uggcucaguu cggaacag                                             18

<210> SEQ ID NO 34
<211> LENGTH: 22
<212> TYPE: RNA
<213> ORGANISM: Homo sapiens

<400> SEQUENCE: 34
cuccugacuc cagguccugu gu                                        22

<210> SEQ ID NO 35
<211> LENGTH: 21
<212> TYPE: RNA
<213> ORGANISM: Homo sapiens

<400> SEQUENCE: 35
ugagguagua guuuguacag u                                         21
```